US012729209B2

(12) United States Patent
Luesch et al.

(10) Patent No.: US 12,729,209 B2
(45) Date of Patent: Sep. 8, 2026

(54) MACROCYCLIC COMPOUNDS AND METHODS OF TREATMENT

(71) Applicants: University of Florida Research Foundation, Incorporated, Gainesville, FL (US); Smithsonian Institution, Washington, DC (US)

(72) Inventors: Hendrik Luesch, Gainesville, FL (US); Valerie J. Paul, Fort Pierce, FL (US); Susan Matthew, Gainesville, FL (US); Qi-Yin Chen, Gainesville, FL (US); Ranjala Ratnayake, Gainesville, FL (US)

(73) Assignees: University of Florida Research Foundation, Incorporated, Gainesville, FL (US); Smithsonian Institution, Washington, DC (US)

( * ) Notice: Subject to any disclaimer, the term of this patent is extended or adjusted under 35 U.S.C. 154(b) by 579 days.

(21) Appl. No.: 18/030,747

(22) PCT Filed: Oct. 6, 2021

(86) PCT No.: PCT/US2021/053777
§ 371 (c)(1),
(2) Date: Apr. 6, 2023

(87) PCT Pub. No.: WO2022/076563
PCT Pub. Date: Apr. 14, 2022

(65) Prior Publication Data

US 2024/0002396 A1 Jan. 4, 2024

Related U.S. Application Data

(60) Provisional application No. 63/088,806, filed on Oct. 7, 2020.

(51) Int. Cl.
*C07D 498/04* (2006.01)

(52) U.S. Cl.
CPC .................................. *C07D 498/04* (2013.01)

(58) Field of Classification Search
None
See application file for complete search history.

(56) References Cited

U.S. PATENT DOCUMENTS

| | | |
|---|---|---|
| 2014/0200319 A1 | 7/2014 | Tian et al. |
| 2019/0194166 A1 | 6/2019 | Adams et al. |
| 2020/0121607 A1 | 4/2020 | Karanikolopoulos et al. |

FOREIGN PATENT DOCUMENTS

| | | |
|---|---|---|
| WO | WO 2022/076563 A1 | 4/2022 |
| WO | WO 2025/085756 A1 | 4/2025 |

OTHER PUBLICATIONS

Weiss et al., Cryptophycins: cytotoxic cyclodepsipeptides with potential for tumor targeting. Journal of Peptide Science, 2017, 23, p. 514-531 (abstract only).*

Prota et al., The Novel Microtubule-Destabilizing Drug BAL27862 Binds to the Colchicine Site of Tubulin with Distinct Effects on Microtubule Organization. Journal of Molecular Biology, 2014, 426, p. 1848-1860.*

Horig, H., Pullman, W. From bench to clinic and back: Perspective on the 1st IQPC Translational Research conference. Journal of Translational Medicine. Dec. 2004, 2, 44.*

Schafer, S., Kolkhof, P. Failure is an option: learning from unsuccessful proof-of-concept trials. Drug Discovery Today. Nov. 2008, 13, 913-916.*

International Search Report and Written Opinion for Application No. PCT/US2021/053777, mailed Jan. 18, 2022.

International Preliminary Report on Patentability for Application No. PCT/US2021/053777, mailed Apr. 20, 2023.

Bertrand, Inside HDAC with HDAC inhibitors. Eur J Med Chem. Jun. 2010;45(6):2095-116. doi: 10.1016/j.ejmech.2010.02.030. Epub Feb. 14, 2010.

Matthew et al., Gatorbulin-1, a distinct cyclodepsipeptide chemotype, targets a seventh tubulin pharmacological site. Proc Natl Acad Sci U S A. Mar. 2, 2021;118(9):e2021847118. doi: 10.1073/pnas.2021847118.

Vigushin et al., Histone deacetylase inhibitors in cancer treatment. Anticancer Drugs. Jan. 2002;13(1):1-13. doi: 10.1097/00001813-200201000-00001.

Bai et al., Binding of dolastatin 10 to tubulin at a distinct site for peptide antimitotic agents near the exchangeable nucleotide and vinca alkaloid sites. J Biol Chem. Oct. 5, 1990;265(28):17141-9.

Bousquet et al., Multidimensional Screening Platform for Simultaneously Targeting Oncogenic KRAS and Hypoxia-Inducible Factors Pathways in Colorectal Cancer. ACS Chem Biol. May 20, 2016;11(5):1322-31. doi: 10.1021/acschembio.5b00860. Epub Mar. 3, 2016. Author manuscript, 22 pages.

Chen et al., Probing a distinct druggable tubulin binding site with gatorbulins 1-7, their metabolic and physicochemical properties, and pharmacological consequences. Bioorg Med Chem. Oct. 21, 2023;95:117506. doi: 10.1016/j.bmc.2023.117506. Supporting information included, 135 pages total.

Cruz-Monserrate et al., Dolastatin 15 binds in the vinca domain of tubulin as demonstrated by Hummel-Dreyer chromatography. Eur J Biochem. Sep. 2003;270(18):3822-8. doi: 10.1046/j.1432-1033.2003.03776.x.

Doodhi et al., Termination of Protofilament Elongation by Eribulin Induces Lattice Defects that Promote Microtubule Catastrophes. Curr Biol. Jul. 11, 2016;26(13):1713-1721. doi: 10.1016/j.cub.2016.04.053. Epub Jun. 16, 2016.

Engene et al., *Caldora penicillata* gen. nov., comb. nov. (cyanobacteria), a pantropical marine species with biomedical relevance. J Phycol. Aug. 2015;51(4):670-81. doi: 10.1111/jpy.12309. Author manuscript, 21 pages.

Guzmán-Martinez et al., An Operationally Simple and Efficient Synthesis of Orthogonally Protected L-threo-beta-Hydroxyasparagine. Synlett. Jun. 1, 2007;2007(10):1513-1516. doi: 10.1055/s-2007-982544. Author manuscript, 7 pages.

(Continued)

*Primary Examiner* — Po-Chih Chen
(74) *Attorney, Agent, or Firm* — Wolf, Greenfield & Sacks, P.C.

(57) ABSTRACT

The instant invention describes macrocyclic compounds having antiproliferation activity, and methods of treating disorders such as cancer, tumors and cell proliferation related disorders.

20 Claims, 28 Drawing Sheets

(56) References Cited

OTHER PUBLICATIONS

Kim et al., Evaluation of class I HDAC isoform selectivity of largazole analogues. Bioorg Med Chem Lett. Aug. 15, 2014;24(16):3728-31. doi: 10.1016/j.bmcl.2014.07.006. Epub Jul. 9, 2014. Author manuscript, 13 pages.
Luesch et al., Targeting and extending the eukaryotic druggable genome with natural products. Nat Prod Rep. Jun. 24, 2020;37(6):744-746. doi: 10.1039/d0np90021d. Author manuscript, 5 pages.
Mabjeesh et al., 2ME2 inhibits tumor growth and angiogenesis by disrupting microtubules and dysregulating HIF. Cancer Cell. Apr. 2003;3(4):363-75. doi: 10.1016/s1535-6108(03)00077-1.
Matthew et al., Intramolecular modulation of serine protease inhibitor activity in a marine cyanobacterium with antifeedant properties. Mar Drugs. Jun. 4, 2010;8(6):1803-16. doi: 10.3390/md8061803.
Matthew et al., Largamides A-C, tiglic acid-containing cyclodepsipeptides with elastase-inhibitory activity from the marine cyanobacterium *Lyngbya confervoides*. Planta Med. Apr. 2009;75(5):528-33. doi: 10.1055/s-0029-1185332. Epub Feb. 12, 2009. Author manuscript, 13 pages.
Matthew et al., Pompanopeptins A and B, new cyclic peptides from the marine cyanobacterium *Lyngbya confervoides*. Tetrahedron. Apr. 2008;64(18):4081-9.
Matthew et al., Tiglicamides A-C, cyclodepsipeptides from the marine cyanobacterium *Lyngbya confervoides*. Phytochemistry. Dec. 2009;70(17-18):2058-63. doi: 10.1016/j.phytochem.2009.09.010. Epub Oct. 6, 2009. Author manuscript, 12 pages.
Menchon et al., A fluorescence anisotropy assay to discover and characterize ligands targeting the maytansine site of tubulin. Nat Commun. May 29, 2018;9(1):2106. doi: 10.1038/s41467-018-04535-8.
Parker et al., An Emerging Role for Tubulin Isotypes in Modulating Cancer Biology and Chemotherapy Resistance. Int J Mol Sci. Jul. 4, 2017;18(7):1434. doi: 10.3390/ijms18071434.
Prota et al., A new tubulin-binding site and pharmacophore for microtubule-destabilizing anticancer drugs. Proc Natl Acad Sci U S A. Sep. 23, 2014;111(38):13817-21. doi: 10.1073/pnas.1408124111. Epub Aug. 11, 2014.
Prota et al., Structural basis of tubulin tyrosination by tubulin tyrosine ligase. J Cell Biol. Feb. 4, 2013;200(3):259-70. doi: 10.1083/jcb.201211017. Epub Jan. 28, 2013.
Ratnayake et al., Dolastatin 15 from a Marine Cyanobacterium Suppresses HIF-1α Mediated Cancer Cell Viability and Vascularization. Chembiochem. Aug. 17, 2020;21(16):2356-2366. doi: 10.1002/cbic.202000180. Epub May 12, 2020. Author manuscript, 23 pages.
Risinger et al., Targeting and extending the eukaryotic druggable genome with natural products: cytoskeletal targets of natural products. Nat Prod Rep. May 1, 2020;37(5):634-652. doi: 10.1039/c9np00053d. Epub Nov. 25, 2019. Author manuscript, 28 pages.
Risinger et al., The Taccalonolides: Microtubule Stabilizers That Circumvent Clinically Relevant Taxane Resistance Mechanisms. Cancer Res. 2008;68(21):8881-8.
Salvador-Reyes et al., Targeted natural products discovery from marine cyanobacteria using combined phylogenetic and mass spectrometric evaluation. J Nat Prod. Mar. 27, 2015;78(3):486-92. doi: 10.1021/np500931q. Epub Jan. 30, 2015.
Schwartz, Antivascular actions of microtubule-binding drugs. Clin Cancer Res. Apr. 15, 2009;15(8):2594-601. doi: 10.1158/1078-0432.CCR-08-2710. Epub Apr. 7, 2009.
Sendai et al., Synthesis of Carumonam (AMA-1080) and a Related Compound Starting from (2R, 3R)-Epoxysuccinic Acid. Chem Pharm Bull. 1985;33(9):3798-810.
Sharp et al., Phylogenetic and chemical diversity of three chemotypes of bloom-forming *Lyngbya* species (Cyanobacteria: Oscillatoriales) from reefs of southeastern Florida. Appl Environ Microbiol. May 2009;75(9):2879-88. doi: 10.1128/AEM.02656-08. Epub Mar. 6, 2009.
Shustov et al., Stereoselective synthesis of multiply substituted [1,2]oxazinan-3-ones via ring-closing metathesis. Can. J. Chem. 2005;83:93-103.
Smith III et al., Design, synthesis, and biological evaluation of EF- and ABEF-analogues of (+)-spongistatin 1. Org Lett. Apr. 16, 2010;12(8):1792-5. doi: 10.1021/ol100418n. Author manuscript, 11 pages.
Steele et al., Diverted Total Synthesis of Promysalin Analogs Demonstrates That an Iron-Binding Motif Is Responsible for Its Narrow-Spectrum Antibacterial Activity. J Am Chem Soc. May 11, 2016;138(18):5833-6. doi: 10.1021/jacs.6b03373. Epub Apr. 28, 2016. Author manuscript, 10 pages.
Supporting information for Matthew et al., Gatorbulin-1, a distinct cyclodepsipeptide chemotype, targets a seventh tubulin pharmacological site. Proc Natl Acad Sci U S A. Mar. 2, 2021;118(9):e2021847118. doi: 10.1073/pnas.2021847118. 89 pages.
Tan et al., Marine Cyanobacteria: A Source of Lead Compounds and their Clinically-Relevant Molecular Targets. Molecules. May 8, 2020;25(9):2197. doi: 10.3390/molecules25092197.
Wang et al., Structures of a diverse set of colchicine binding site inhibitors in complex with tubulin provide a rationale for drug discovery. FEBS J. Jan. 2016;283(1):102-11. doi: 10.1111/febs.13555. Epub Nov. 4, 2015.
Weinert et al., Serial millisecond crystallography for routine room-temperature structure determination at synchrotrons. Nat Commun. Sep. 14, 2017;8(1):542. doi: 10.1038/s41467-017-00630-4.

* cited by examiner

Table 1. NMR spectral data for GB1 (1) both conformers (1:1) in DMF-$d_7$ (500 MHz)

| | | conformer 1 | | | | | | conformer 2 | | |
|---|---|---|---|---|---|---|---|---|---|---|
| unit | C/H no. | $\delta_H$ (*J* in Hz) | $\delta_C$, mult[a] | $\delta_N$ | COSY | $^1H-^{13}C$ HMBC | $^1H-^{15}N$ HMBC | $\delta_H$ (*J* in Hz) | $\delta_C$, mult[a] | $\delta_N$ |
| DhAla | 1 | | 165.9, qC | | | | | | 166.8, qC | |
| | 2 | | 136.3, qC | | | | | | 136.2, qC | |
| | 3a | 6.46, s | 101.8, $CH_2$ | | H-3b | 1, 2 | | 6.22, s | 103.0, $CH_2$ | |
| | 3b | 5.22, s | | | H-3a | 1 | | 5.11, s | | |
| | NH | 8.28, s | | −258.2 | | 1, 1 (Ala) | H-3a, H-3b | 8.60, s | | −258.2 |
| N-OH-Ala | 1 | | 170.5, qC | | | | | | 170.2, qC | |
| | 2 | 4.29, q (6) | 64.7, CH | | $H_3$-3, NH | 1, 3 | | 4.71, br q (6) | 66.0, CH | |
| | 3 | 1.54, d (6) | 13.8, $CH_3$ | | H-2 | 1, 2 | | 1.42, d (6) | 15.6, $CH_3$ | |
| | N-OH | 11.35, br s | | −202.6 | | | H-2, $H_3$-3 | 10.58, br | | −205.1 |
| 3-OH-*N*-Me-Asn | 1 | | 170.4, qC | | | | | | 169.4, qC | |
| | 2 | 5.51, br d (9.5) | 58.0 (br), CH | | H-3, | 1, 2 | | 5.85 | not observed | |
| | 3 | 4.51, dd (9.5, 4.5) | 68.8, CH | | H-2, 3-OH | 1, 2, 4 | | 4.65, br dd (6, 6) | 69.7, CH | |
| | 3-OH | 6.03, br d | | | H-3 | | | 5.06, br | | |
| | 4 | | 175.1, qC | | | | | | 174.8 | |
| | *N*-Me | 3.09, s | 34.0, $CH_3$ | −273.8 | | 2, 1 (Lac) | *N*-Me | 3.14, s | 34.5 (br), $CH_3$ | −271.7 |
| | 4-NHa | 7.26, s | | −280.5 | 4-NHb | | | 7.39, s | | −279.6 |
| | 4-NHb | 7.09, s | | | 4-NHa | 3 | | 7.21, s | | |
| Lac | 1 | | 169.9, qC | | | | | | 169.7, qC | |
| | 2 | 5.47, q (7.0) | 72.9, CH | | $H_3$-3 | 1, 3, 1 (MePro) | | 5.39, q (7.0) | 72.1, CH | |
| | 3 | 1.42, d (7.0) | 17.6, $CH_3$ | | H-2 | 1, 2 | | 1.41, d (7.0) | 17.5, $CH_3$ | |
| 4-Me-Pro | 1 | | 170.8, qC | | | | | | 170.4, qC | |
| | 2 | 4.42, t (7.0) | 62.6, CH | | H-3a, H-3b | 1, 3 | | 4.94, dd (9, 8) | 63.8, CH | |
| | 3a (*proS*) | 2.58, m | 37.0, $CH_2$ | | H-2, H-3b, H-4 | 1, 2, 4, 5, 6 | | 2.53, m | 40.8, $CH_2$ | |
| | 3b (*proR*) | 1.58, m | | | H-2, H-3a, H-4 | 1, 2, 4, 5, 6 | | 1.65, m | | |
| | 4 | 2.53, m | 34.7, CH | | H-3a, H-3b, H-5a, H-5b, $H_3$-6 | 3, 5, 6 | | 2.38, m | 32.4, CH | |
| | 5a (*proR*) | 4.31, dd (−10.0, 6.0) | 56.9, $CH_2$ | | H-4, H-5b | 2, 3, 4, 6 | | 3.71, dd (−11.0, 7.0) | 55.8, $CH_2$ | |
| | 5b (*proS*) | 3.25, dd (−10.0, 8.5) | | | H-4, H-5a | 3, 6 | | 3.11, dd (−11.0, 11) | | |
| | 6 | 1.12, d (7.0) | 18.0, $CH_3$ | | H-4 | 3, 4, 5 | | 1.11, d (7.0) | 16.9, $CH_3$ | |

FIG. 1

Table 2. NMR spectral data for GB2 (2) both conformers (1:1) in DMF-$d_7$ (600 MHz)

| | | conformer 1 | | | | | conformer 2 | |
|---|---|---|---|---|---|---|---|---|
| unit | C/H no. | $\delta_H$ ($J$ in Hz) | $\delta_C$, mult[a] | COSY | HMBC | NOESY | $\delta_H$ ($J$ in Hz) | $\delta_C$, mult[a] |
| DhAla | 1 | | 166.5, qC | | | | | 165.6, qC |
| | 2 | | 136.7, qC | | | | | 136.6, qC |
| | 3a | 6.15, s | 102.1, $CH_2$ | H-3b | 1, 2 | H-3b, NH, H-2 (MePro) | 6.22, s | 101.7, $CH_2$ |
| | 3b | 5.03, s | | H-3a | 1, 2 | H-3a, NH, for conf. 1 only: H-2 (MePro), for conf. 2 only: H-5a (MePro) | 5.11, s | |
| | NH | 8.79, s | | | 1, 1 (Ala) | H-3a, H-3b, H-2 (Ala) | 8.60, s | |
| Ala | 1 | | 172.8, qC | | | | | 171.5, qC |
| | 2 | 4.17, qd (6.4, 4.5) | 51.5, CH | $H_3$-3, NH | 1, 3, 1 (Asn) | $H_3$-3, NH, NH (DhAla) | 4.42, qd (7.2, 7.1) | 49.6, CH |
| | 3 | 1.41, d (6.4) | 16.6, $CH_3$ | H-2 | 2 | H-2, NH, H-2 (Asn) | 1.42, d (7.1) | 18.2, $CH_3$ |
| | NH | 8.21, d (4.5) | | H-2 | 2, 1 (Asn) | H-2, $H_3$-3 | 8.38, d (7.2) | |
| N-Me-3-OH-Asn | 1 | | 169.6, qC | | | | | 169.5, qC |
| | 2 | 3.68, d (9.4) | 68.5, CH | H-3, | 1, 2, 4 | H-3, 3-OH, H-4, NHa, H-4NHb, NMe, NH (Ala) | 3.99, dd (10.3, 7.7) | 66.9, CH |
| | 3 | 4.88, br | 67.8, CH | H-2, 3-OH | | H-2, NMe, $H_3$-3 (Ala), NH (Ala) | 4.77, br | 68.3, CH |
| | 3-OH | 6.41, br | | H-3 | | H-2 | 6.48, br | |
| | 4 | | 173.9, qC | | | | | nd |
| | NMe | 3.20, s | 38.6, $CH_3$ | | 2, 1 (Lac) | H-2, NH (Ala), H-2 (Lac), $H_3$-3 (Lac) | 3.18, s | 37.4, $CH_3$ |
| | 4-NHa | 7.70, s | | 4-NHb | 3 | H-2 | 7.55, s | |
| | 4-NHb | 7.24, s | | 4-NHa | 3 | H-2 | 7.23, s | |
| Lac | 1 | | 171.4, qC | | | | | 170.6, qC |
| | 2 | 5.42, q (6.7) | 67.2, CH | $H_3$-3 | 1, 3, 1 (MePro) | $H_3$-3, NMe (Asn) | 5.02, q (6.5) | 66.8, CH |
| | 3 | 1.39, d (6.7) | 15.3, $CH_3$ | H-2 | 1, 2 | H-2, NMe (Asn) | 1.38, d (6.5) | 16.5, $CH_3$ |
| 4-Me-Pro | 1 | | 170.8, qC | | | | | 170.5, qC |
| | 2 | 4.78, dd (7.8, 7.8) | 61.4, CH | H-3a, H-3b | 1, 5 | H-3a, H-3b, H-4, H-5a, for conformer 1 only: H-3b (DhAla) | 4.28, dd (7.8, 7.8) | 61.2, CH |
| | 3a (proS) | 2.63, ddd (−12.2, 8.9, 7.8) | 37.4, $CH_2$ | H-2, H-3b, H-4 | 1, 2, 4, 5, 6 | H-2, H-3b, H-4, $H_3$-6 | 2.53, ddd (−11.5, 8.4, 7.8, ) | 35.7, $CH_2$ |
| | 3b (proR) | 1.71, ddd (−12.2, 7.8, 4.5) | | H-2, H-3a, H-4 | 1, 2, 4, 5, 6 | H-2, H-3a, H-4, H-5b, $H_3$-6 | 1.54, ddd (−11.5; 7.8, 4) | |
| | 4 | 2.34, ddqdd (10.8, 8.9, 7.8, 6, 4.5) | 31.1, CH | H-3a, H-3b, H-5a, H-5b, $H_3$-6 | 2, 3, 5, 6 | H-2, H-3a, H-3b, $H_3$-6 | 2.51, ddqdd (9.6, 8.4, 7.5, 6, 4) | 33.5, CH |
| | 5a (proR) | 3.89, dd (−10.4, 7.8) | 53.6, $CH_2$ | H-4, H-5b | 2, 3, 4, 6 | H-2, H-4, H-5b, $H_3$-6, for conf. 2 only: H-3 (DhAla) | 4.23, dd (−9.2, 7.5) | 55.6, $CH_2$ |
| | 5b (proS) | 3.04, dd (−10.4, 10.8) | | H-4, H-5a | 2, 3, 4, 6, for conf. 2 only: 1 (DhAla) | H-3b, H-4, H-5a, $H_3$-6 | 3.24, dd (−9.2, 9.6) | |
| | 6 | 1.12, d (6) | 16.7, $CH_3$ | H-4 | 3, 4, 5 | H-3a, H-3b, H-4, H-5a, H-5b | 1.10, d (6) | 16.7, $CH_3$ |

FIG. 2

Table 1. NMR data for gatorbulin-1 (GB1, 1 ) for both conformers (1:1) in DMF-$d_7$ at 600 MHz ($^1$H) and 150 MHz ($^{13}$C)

| | | conformer 1 | | | | | | conformer 2 | | |
|---|---|---|---|---|---|---|---|---|---|---|
| unit | C/H no. | $\delta_H$ ($J$ in Hz) | $\delta_C$, mult | $\delta_N$ | COSY | $^1$H–$^{13}$C HMBC | $^1$H–$^{15}$N HMBC | $\delta_H$ ($J$ in Hz) | $\delta_C$, mult | $\delta_N$ |
| DhAla | 1 | | 165.9, qC | | | | | | 166.8, qC | |
| | 2 | | 136.3, qC | | | | | | 136.2, qC | |
| | 3a | 6.46, s | 101.8, $CH_2$ | | H-3b | 1, 2 | | 6.22, s | 103.0, $CH_2$ | |
| | 3b | 5.22, s | | | H-3[a] | 1 | | 5.11, s | | |
| | NH | 8.28, s | | –258.2 | | 1, 1 (Ala) | H-3a, H-3b | 8.60, s | | –258.2 |
| N-OH-Ala | 1 | | 170.5, qC | | | | | | 170.2, qC | |
| | 2 | 4.29, q (6) | 64.7, CH | | $H_3$-3, NH | 1, 3 | | 4.71, br q (6) | 60.0, CH | |
| | 3 | 1.54, d (6) | 13.8, $CH_3$ | | H-2 | 1, 2 | | 1.42, d (6) | 15.6, $CH_3$ | |
| | N-OH | 11.35, br s | | –202.6 | | | H-2, $H_3$-3 | 10.58, br | | –205.1 |
| *N*(α)-Me-β-OH-Asn | 1 | | 170.4, qC | | | | | | 169.4, qC | |
| | 2 | 5.51, br d (9.5) | 58.0 (br), CH | | H-3, | 1, 2 | | 5.85 | not observed | |
| | 3 | 4.51, dd (9.5, 4.5) | 68.8, CH | | H-2, 3-OH | 1, 2, 4 | | 4.65, br dd (6, 6) | 69.7, CH | |
| | 3-OH | 6.05, br d | | | H-3 | | | 5.06, br | | |
| | 4 | | 175.1, qC | | | | | | 174.8 | |
| | *N*-Me | 3.09, s | 34.0, $CH_3$ | –273.8 | | 2, 1 (Lac) | *N*-Me | 3.14, s | 34.5 (br), $CH_3$ | –271.7 |
| | 4-NHa | 7.26, s | | –280.5 | 4-NHb | | | 7.39, s | | –279.6 |
| | 4-NHb | 7.09, s | | | 4-NHa | 3 | | 7.21, s | | |
| Lac | 1 | | 169.9, qC | | | | | | 169.7, qC | |
| | 2 | 5.47, q (7.0) | 72.9, CH | | $H_3$-3 | 1, 3, 1 (MePro) | | 5.39, q (7.0) | 72.1, CH | |
| | 3 | 1.42, d (7.0) | 17.6, $CH_3$ | | H-2 | 1, 2 | | 1.41, d (7.0) | 17.3, $CH_3$ | |
| 4-Me-Pro | 1 | | 170.8, qC | | | | | | 170.4, qC | |
| | 2 | 4.42, t (7.0) | 62.6, CH | | H-3a, H-3b | 1, 3 | | 4.94, dd (9, 8) | 63.8, CH | |
| | 3a (*proS*) | 2.58, m | 37.0, $CH_2$ | | H-2, H-3b, H-4 | 1, 2, 4, 5, 6 | | 2.53, m | 40.8, $CH_2$ | |
| | 3b (*proR*) | 1.58, m | | | H-2, H-3a, H-4 | 1, 2, 4, 5, 6 | | 1.65, m | | |
| | 4 | 2.53, m | 34.7, CH | | H-3a, H-3b, H-5a, H-5b, $H_3$-6 | 3, 5, 6 | | 2.38, m | 32.4, CH | |
| | 5a (*proR*) | 4.31, dd (–10.0, 6.0) | 56.9, $CH_2$ | | H-4, H-5b | 2, 3, 4, 6 | | 3.71, dd (–11.0, 7.0) | 55.6, $CH_2$ | |
| | 5b (*proS*) | 3.25, dd (–10.0, 8.5) | | | H-4, H-5a | 3, 6 | | 3.11, dd (–11.0, 11) | | |
| | 6 | 1.12, d (7.0) | 18.0, $CH_3$ | | H-4 | 3, 4, 5 | | 1.11, d (7.0) | 16.9, $CH_3$ | |

FIG. 18

Gatorbulin-1 (1a): R = OH
Gatorbulin-2 (1b): R = H
$TiCl_3$

$^{15}N$ chemical shifts

DhAla
-258.2/-258.2 (NH)

N-OH-L-Ala
-202.6/-205.1 (NOH)

L-erythro-N(α)-
Me-β-OH-Asn
-273.8/-271.7(NMe)

L-erythro-N(α)-
Me-β-OH-Asn
-280.5/-279.6 ($NH_2$)

GB1 (1a)
2
3
4
5
6
7
8
9

MACROCYCLIC COMPOUNDS AND METHODS OF TREATMENT

CROSS REFERENCE TO RELATED APPLICATIONS

This application is a national stage filing under 35 U.S.C. 371 of International Patent Application Serial No. PCT/US2021/053777, filed Oct. 6, 2021, entitled "MACROCYCLIC COMPOUNDS AND METHODS OF TREATMENT", which claims priority to U.S. Provisional Application No. 63/088,806, filed Oct. 7, 2020. The entire contents of these applications are incorporated herein by reference in their entirety.

STATEMENT OF RIGHTS TO INVENTIONS MADE UNDER FEDERALLY SPONSORED RESEARCH

This invention was made with government support under Grant Nos. CA172310 and GM086210 awarded by the National Institutes of Health. The government has certain rights in the invention.

BACKGROUND

Microtubules are polarized polymers consisting of α/β-tubulin heterodimers involved in cellular structure, motility, proliferation, and intracellular trafficking[1]. Pharmacological targeting of tubulin dynamics at different sites has been a validated strategy for cancer therapy for decades and has mostly been linked to the antimitotic effects of these compounds, although increasing evidence has emerged for the importance of non-mitotic effects[1]. Natural products targeting tubulin in particular have yielded a wealth of chemically diverse agents and provided the basis for several FDA-approved drugs, both for cancer and other pathologies, and either alone or as antibody-drug conjugate (ADC), including paclitaxel, vincristine, maytansine, eribulin, and colchicine. Compounds can be classified based on their binding to one of the six known binding sites, and even though they are all targeting tubulin, they have shown distinct pharmacological effects. Therefore, there is a persistent interest in the identification of novel microtubule-targeting agents.

BRIEF SUMMARY OF THE INVENTION

Our investigation of marine cyanobacteria as a source of potential anticancer agents has previously yielded the modified peptides dolastatins 10 and 15 (H. Luesch, et al., *J. Nat. Prod.* 64, 907-910 (2001); L. A. Salvador-Reyes, et al., *J. Nat. Prod.* 78, 486-492 (2015); R. Ratnayake et al., *Chem Bio Chem.* 21, 2356-2366 (2020)), targeting the vinca site (R. Bai, et al., *J. Biol. Chem.* 265, 17141-17149 (1990); Z. Cruz-Monserrate, et al., *Eur. J. Biochem.* 270, 3822-3828 (2003)). Three ADCs with a dolastatin 10 analogue (monomethyl auristatin E, MMAE) as the cytotoxic payload are approved for the treatment of various lymphomas and refractory bladder cancer, while dolastatin 15-based ADCs have advanced to clinical trials (R. Ratnayake et al., *Chem Bio Chem.* 21, 2356-2366 (2020)). We identified both dolastatins 10 and 15 as indirect hypoxia-inducible factor (HIF) inhibitors based on differential cytotoxicity against a panel of isogenic HCT116 colorectal cancer cells (R. Ratnayake et al., *Chem Bio Chem.* 21, 2356-2366 (2020); M. S. Bousquet et al., *ACS Chem. Biol.* 11, 1322-1331 (2016)) which indicated that HIF inhibition is functionally relevant for the mechanisms of action of these compounds. HIF is activated in solid tumors, promotes metastasis, and targeted screening early in the drug discovery process could provide a rapid indication for requisite selectivity for cancer treatment (J. Pouysségur, et al. *Nature* 441, 437-443 (2006); G. L. Semenza, et al., *Nat. Rev. Cancer* 3, 721-732 (2003); H. Zhong et al., *Cancer Res.* 59, 5830-5835 (1999)). Using the same isogenic screening system, we now identified a new antiproliferative agent that also possessed preferential activity for oncogenic KRAS- and HIF-1α-containing HCT116 cells and is a microtubule-destabilizing cyclodepsipeptide. We named the compound gatorbulin-1 (GB1), in analogy to eribulin (Eisai Research Institute).

The invention is directed towards macrocyclic compounds (i.e., any delineated herein), methods of modulating proliferation activity, and methods of treating proliferation disease and disorders.

In one embodiment, the invention provides a compound according to Formula I (e.g., Compound 1 or 2, Gatorbulin-1 (GB1) and Gatorbulin-2 (GB2), respectively):

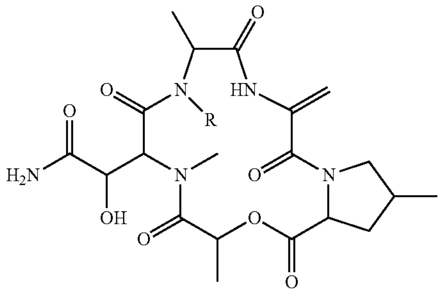

GB1 R = OH
GB2 R = H wherein:

each R is independently H or OH;

and pharmaceutically acceptable salts, solvates, or hydrates thereof.

In certain instances, the compounds of the invention are selected from the following of the formulae herein (including Formula I) having the structure:

TABLE A

| Cmpd. No. | R | Name |
|---|---|---|
| 1 or 1a | OH | GB1 |
| 2 or 1b | H | GB2 |

In another aspect, the invention provides a pharmaceutical composition comprising the compound of formula I and a pharmaceutically acceptable carrier.

In other aspects, the invention provides a method of modulating the proliferation activity in a subject, comprising contacting the subject with a compound of formula I, in an amount and under conditions sufficient to modulate proliferation activity.

In one aspect, the invention provides a method of treating a subject suffering from or susceptible to a proliferation related disorder or disease, comprising administering to the subject an effective amount of a compound or pharmaceutical composition of formula I.

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, an effective amount of a compound or pharmaceutical composition of formula I, such that said subject is treated for said disorder.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of formula I, such that cell proliferation in said subject is modulated (e.g., down regulated). In another aspect, the compounds delineated herein preferentially target cancer cells over nontransformed cells.

In a specific aspect, the invention provides a method of treating cancer, tumor growth, cancer of the colon, breast, bone, brain and others (e.g., osteosarcoma, neuroblastoma, colon adenocarcinoma), comprising administering to said subject in need thereof, an effective amount of a compound delineated herein (e.g., Formula I), and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries (i.e., ovarian cancer), vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). In some aspects, the invention provides a method of treating breast cancer. In some aspects, the invention provides a method of treating ovarian cancer.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

BRIEF DESCRIPTION OF THE DRAWINGS

The present invention is further described below with reference to the following non-limiting examples and with reference to the following figures, in which:

FIG. 1. depicts an exemplary NMR spectral data for GB1(1) both conformers (1:1) in DMF-$d_7$ (500 MHz) (Table 1).

FIG. 2. depicts an exemplary NMR spectral data for GB2 (2) both conformers (1:1) in DMF-$d_7$ (600 MHz) (Table 2).

FIG. 18 depicts exemplary NMR data for gatorbulin-1 (GB1, 1a) for both conformers (1:1) in DMF-$d_7$ at 600 MHz ($^1H$) and 150 MHz ($^{13}C$).

DETAILED DESCRIPTION

Definitions

Figure 3:
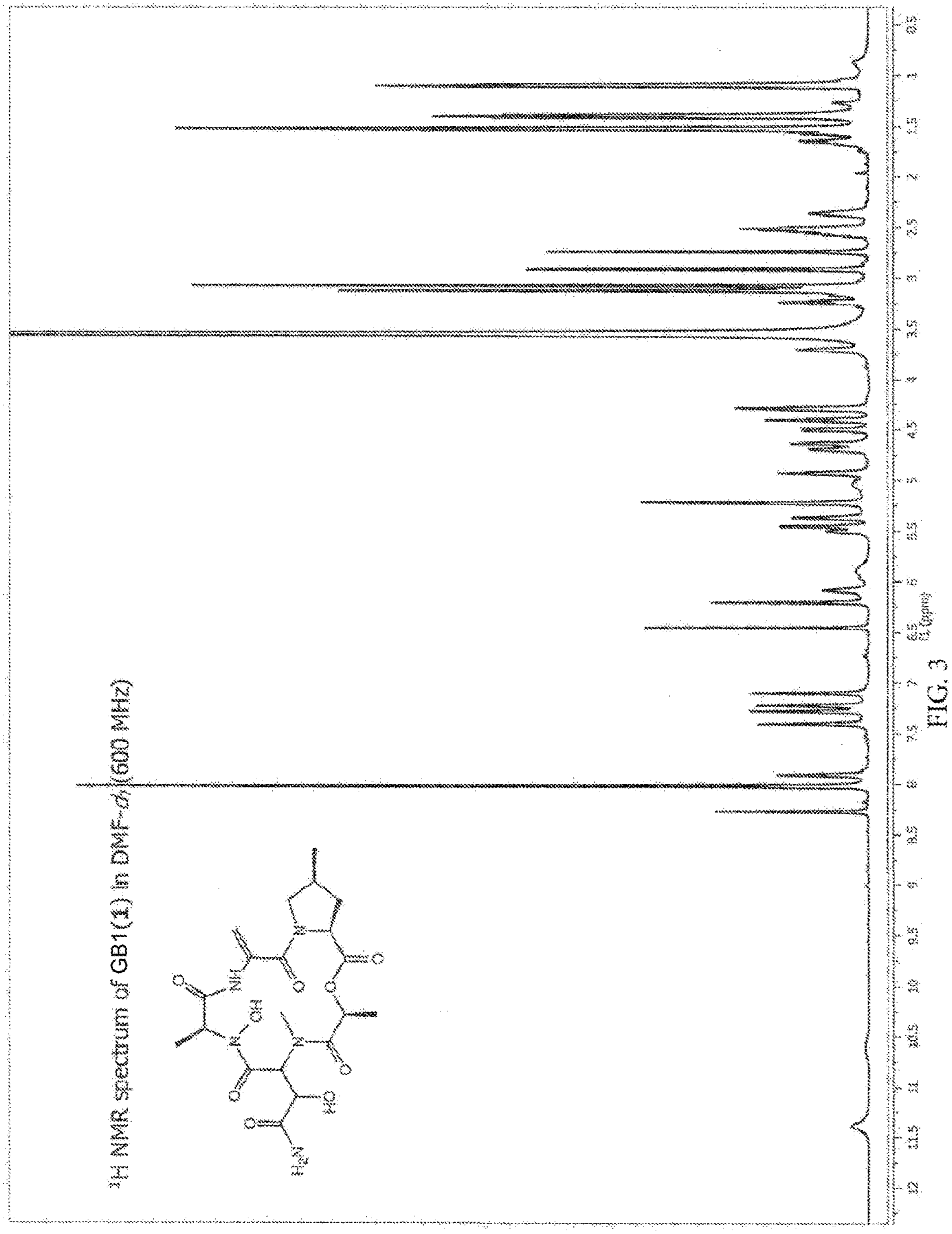
FIG. 3 depicts an exemplary $^1H$ NMR spectrum of GB1 (1) in DMF-$d_7$ (600 MHz).
Figure 4:
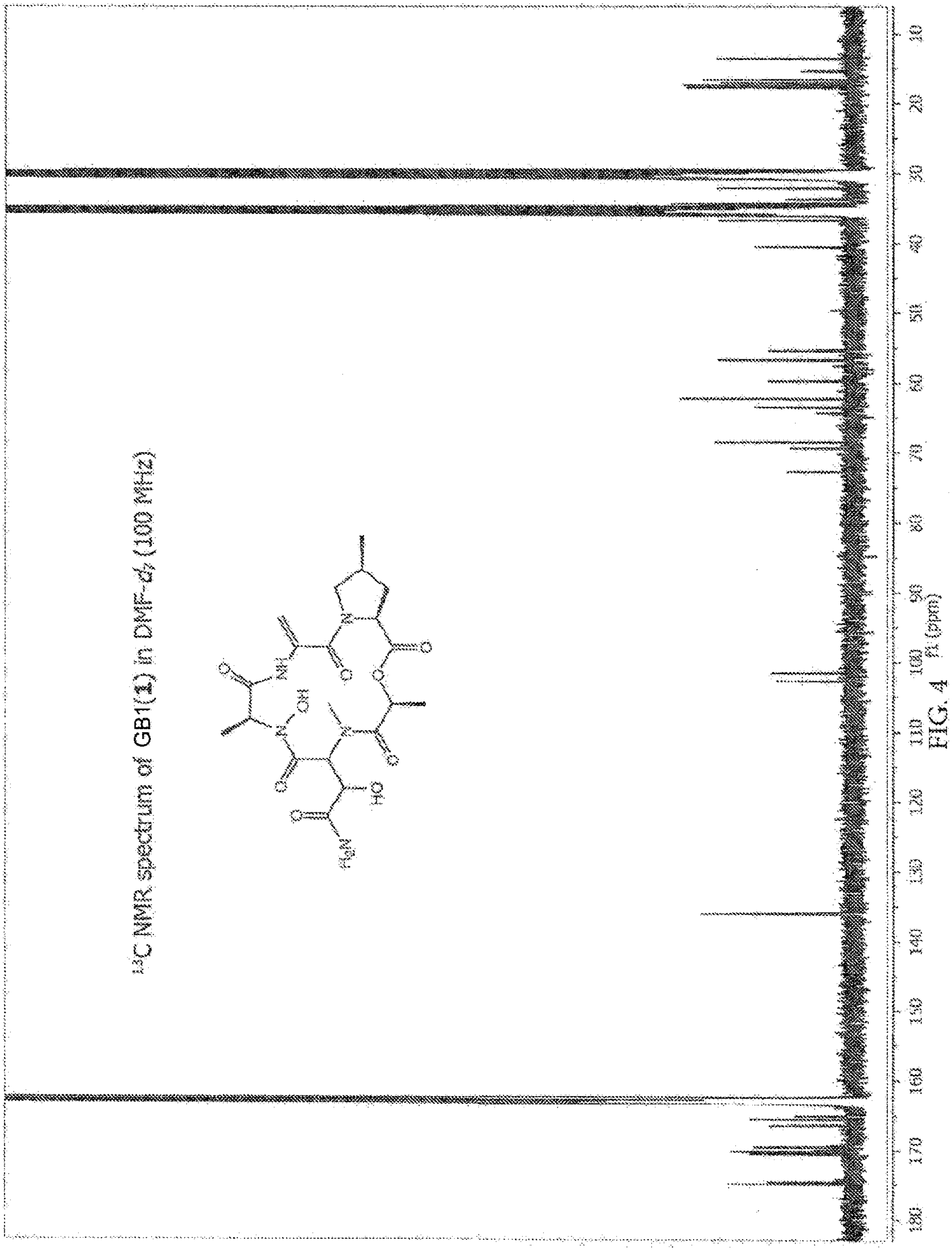
FIG. 4 depicts an exemplary $^{13}C$ NMR spectrum of spectrum of GB1 (1) in DMF-$d_7$ (100 MHz).
Figure 5:
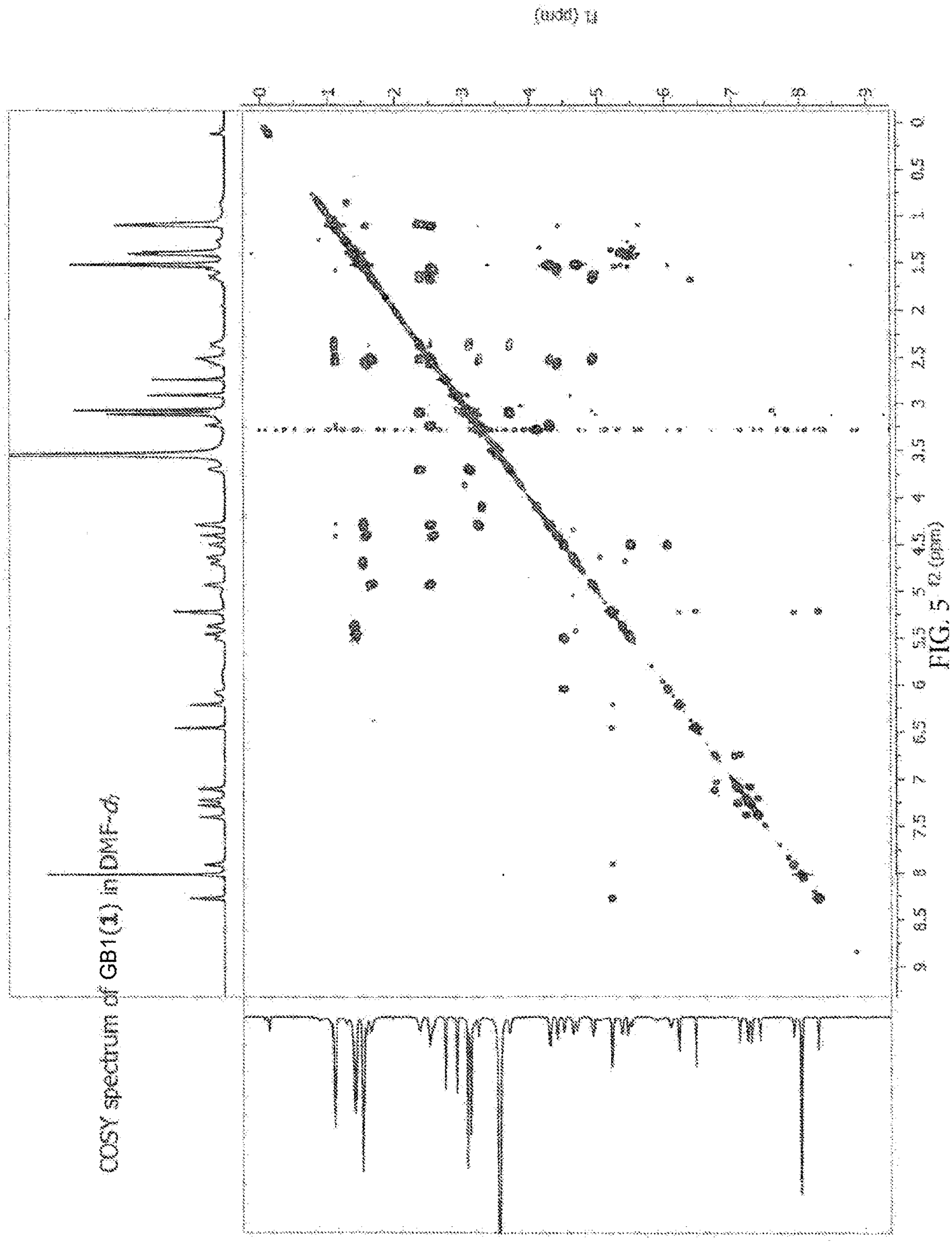
FIG. 5 depicts an exemplary COSY spectrum of GB1 (1) in DMF-$d_7$.
Figure 6:
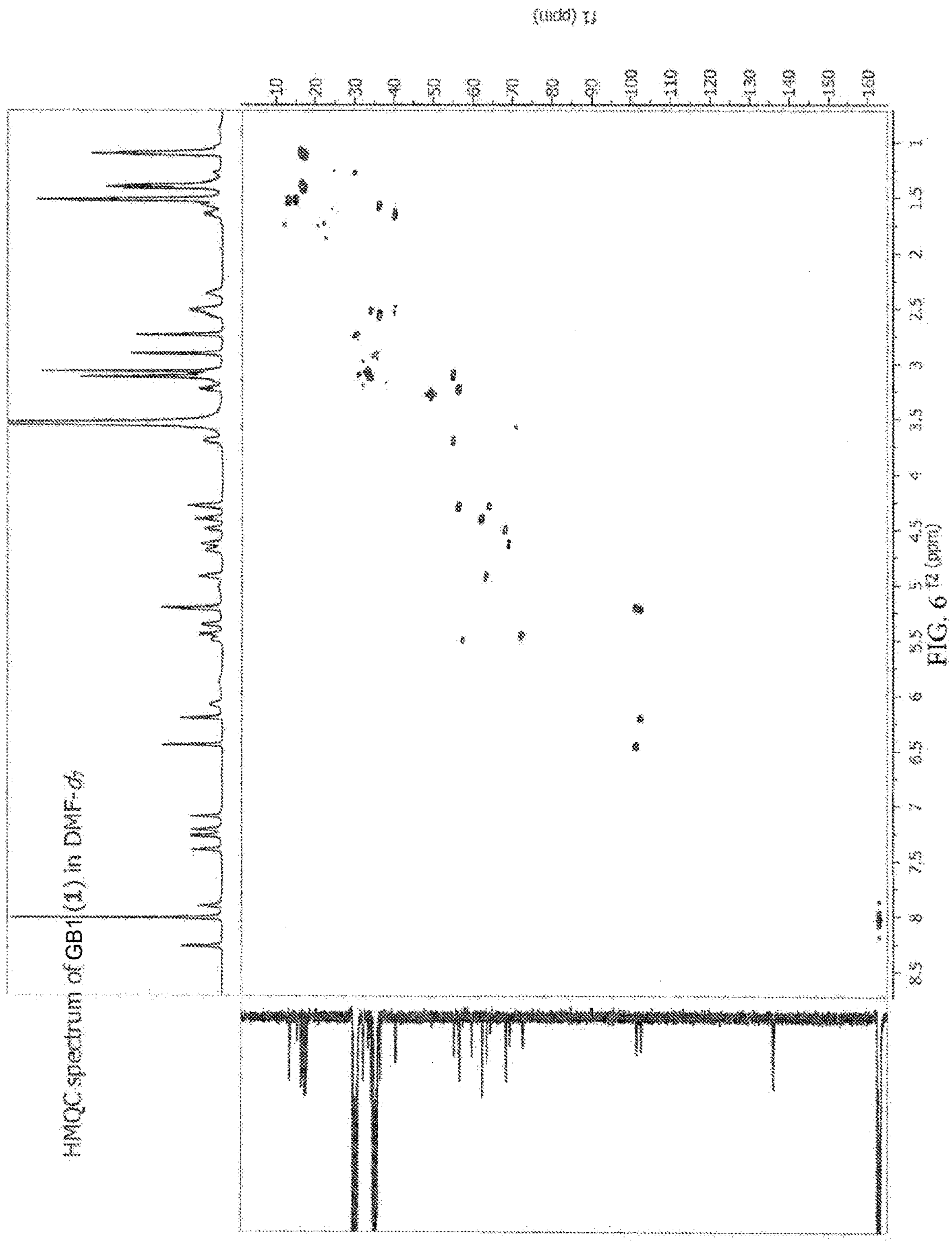
FIG. 6 depicts an exemplary HMQC spectrum of GB1 (1) in DMF-$d_7$.
Figure 7:
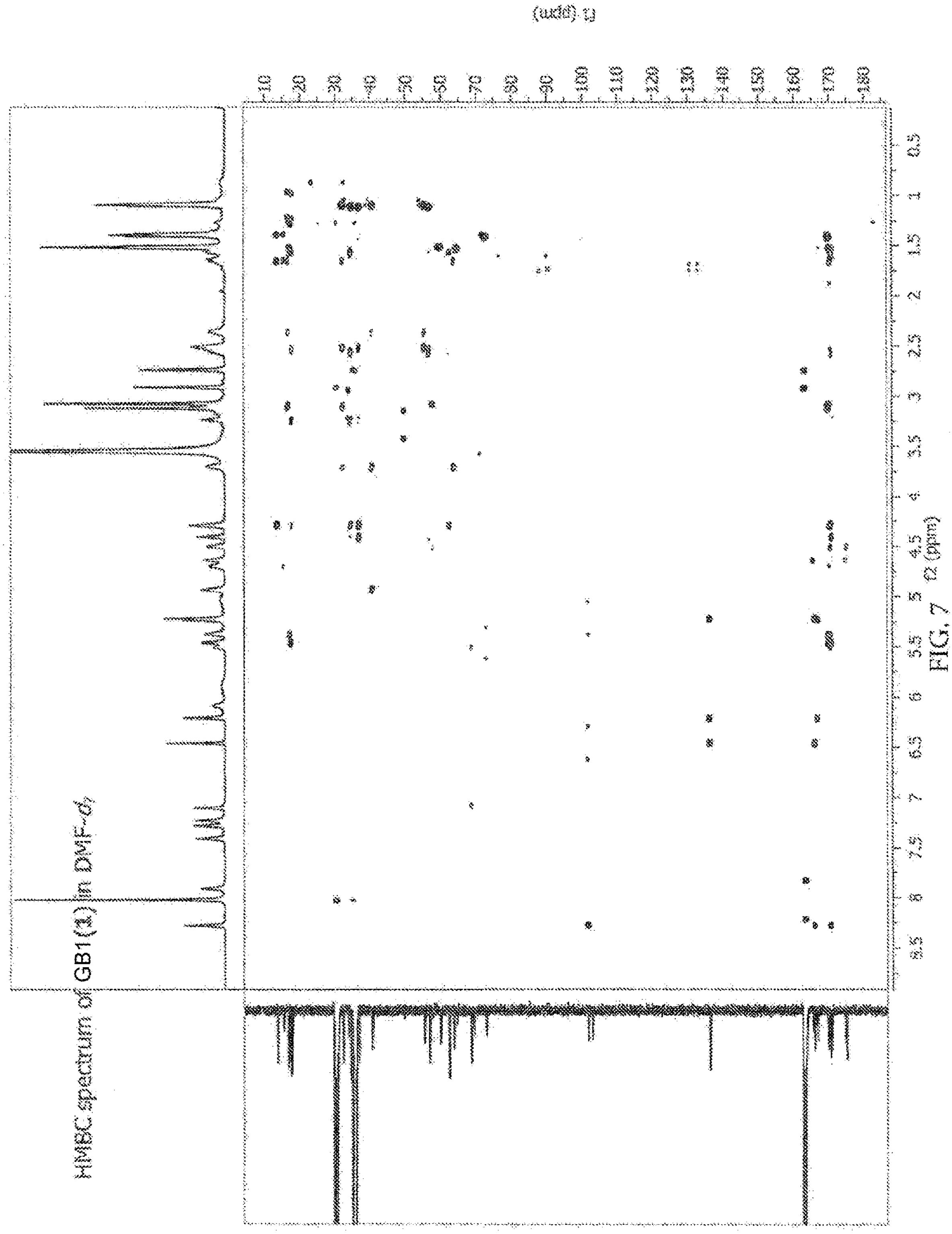
FIG. 7 depicts an exemplary HMBC spectrum of GB1 (1) in DMF-$d_7$.
Figure 8:
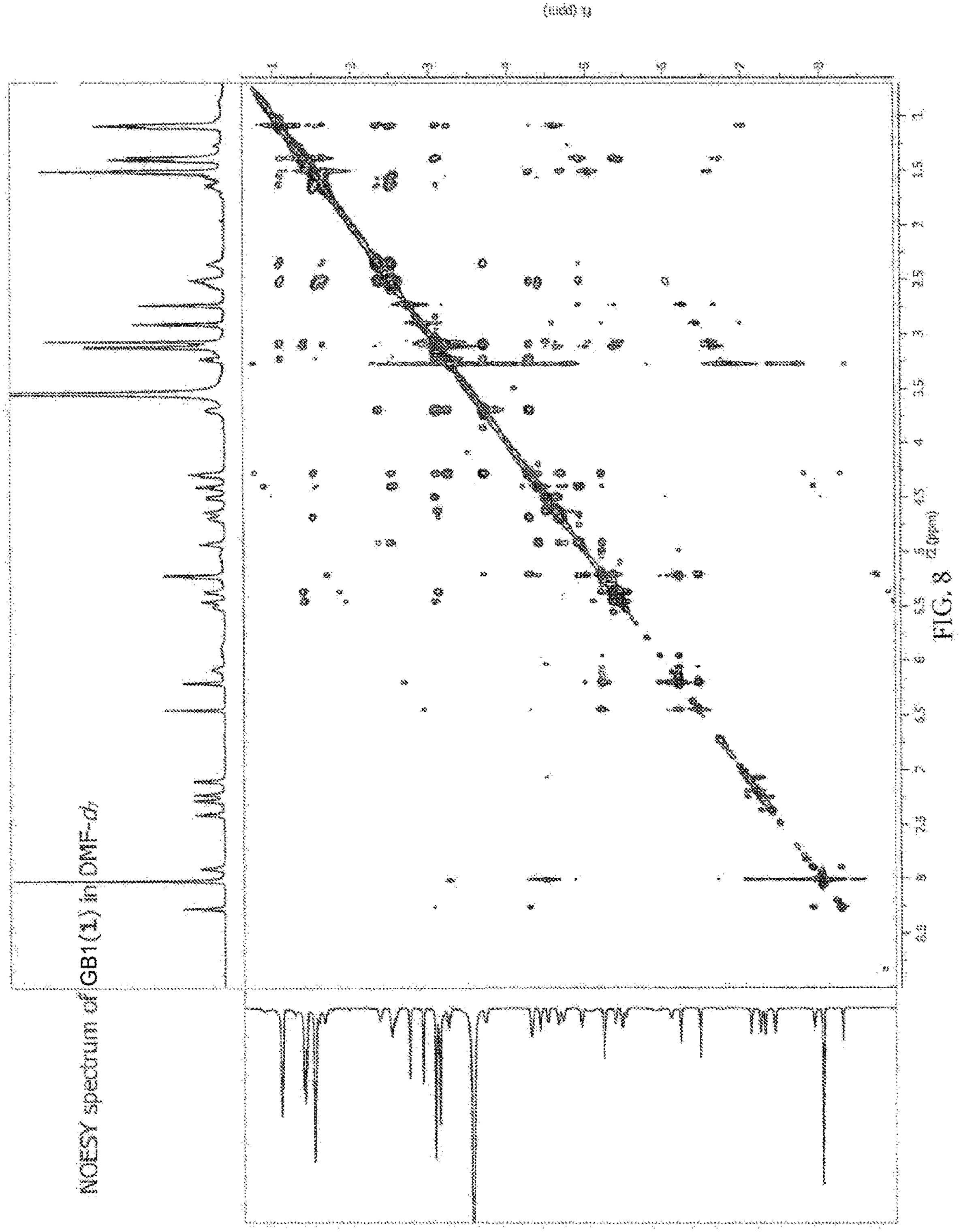
FIG. 8 depicts an exemplary NOESY spectrum of GB1 (1) in DMF-$d_7$.
Figure 9:
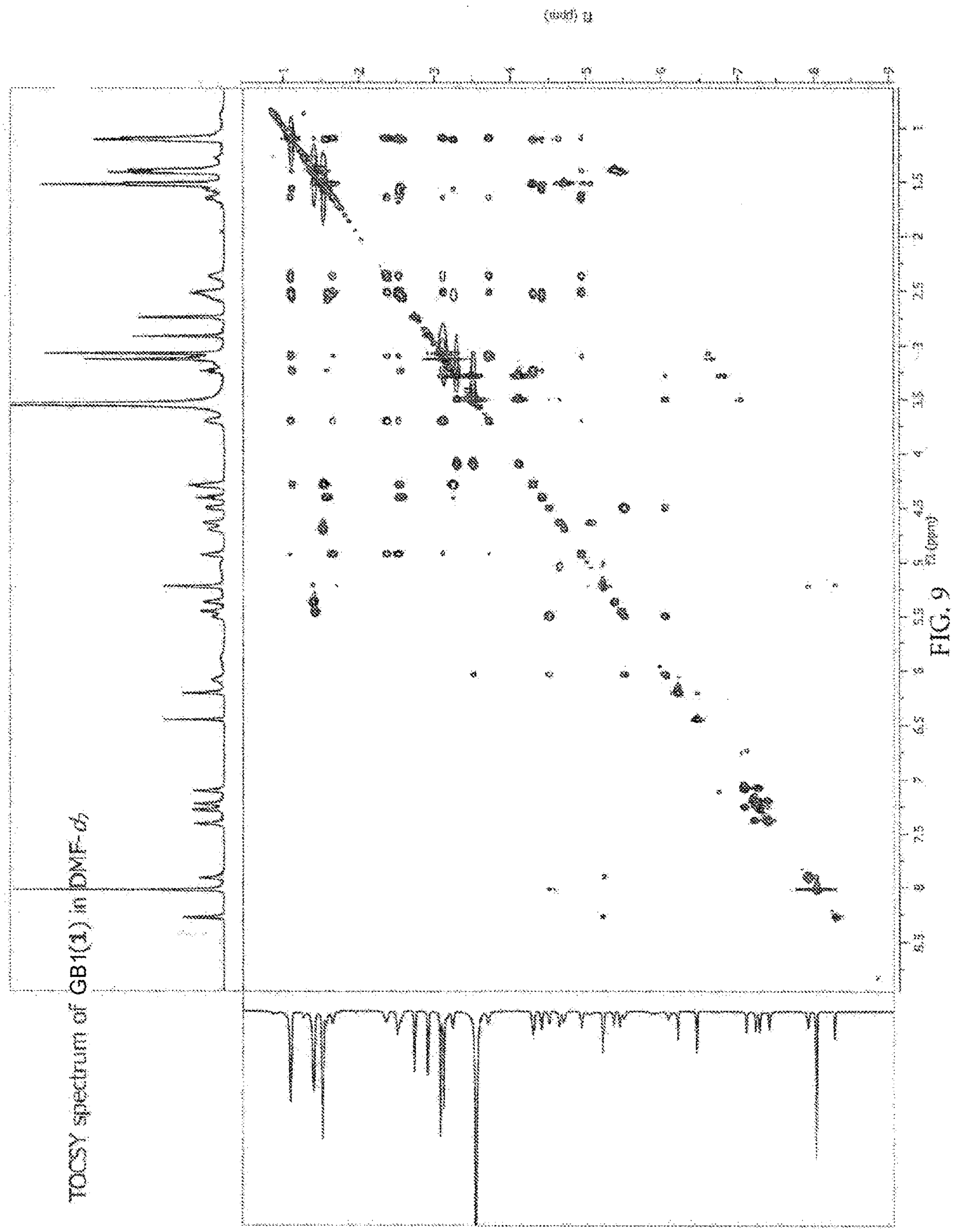
FIG. 9 depicts an exemplary TOCSY spectrum of GB1 (1) in DMF-$d_7$.
Figure 10:
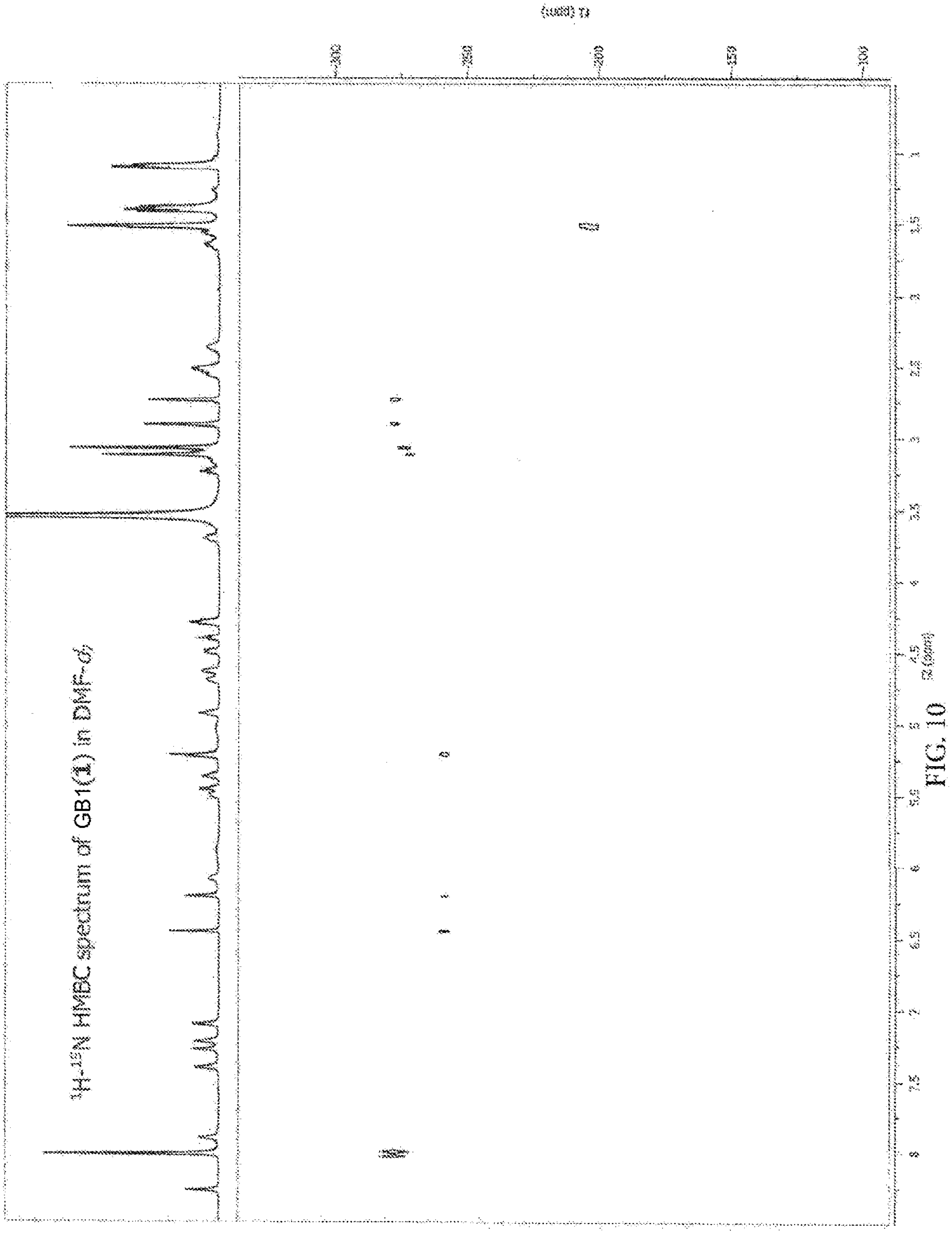
FIG. 10 depicts an exemplary $^1H$-$^{15}N$ HMBC spectrum of GB1 (1) in DMF-$d_7$.
Figure 11:
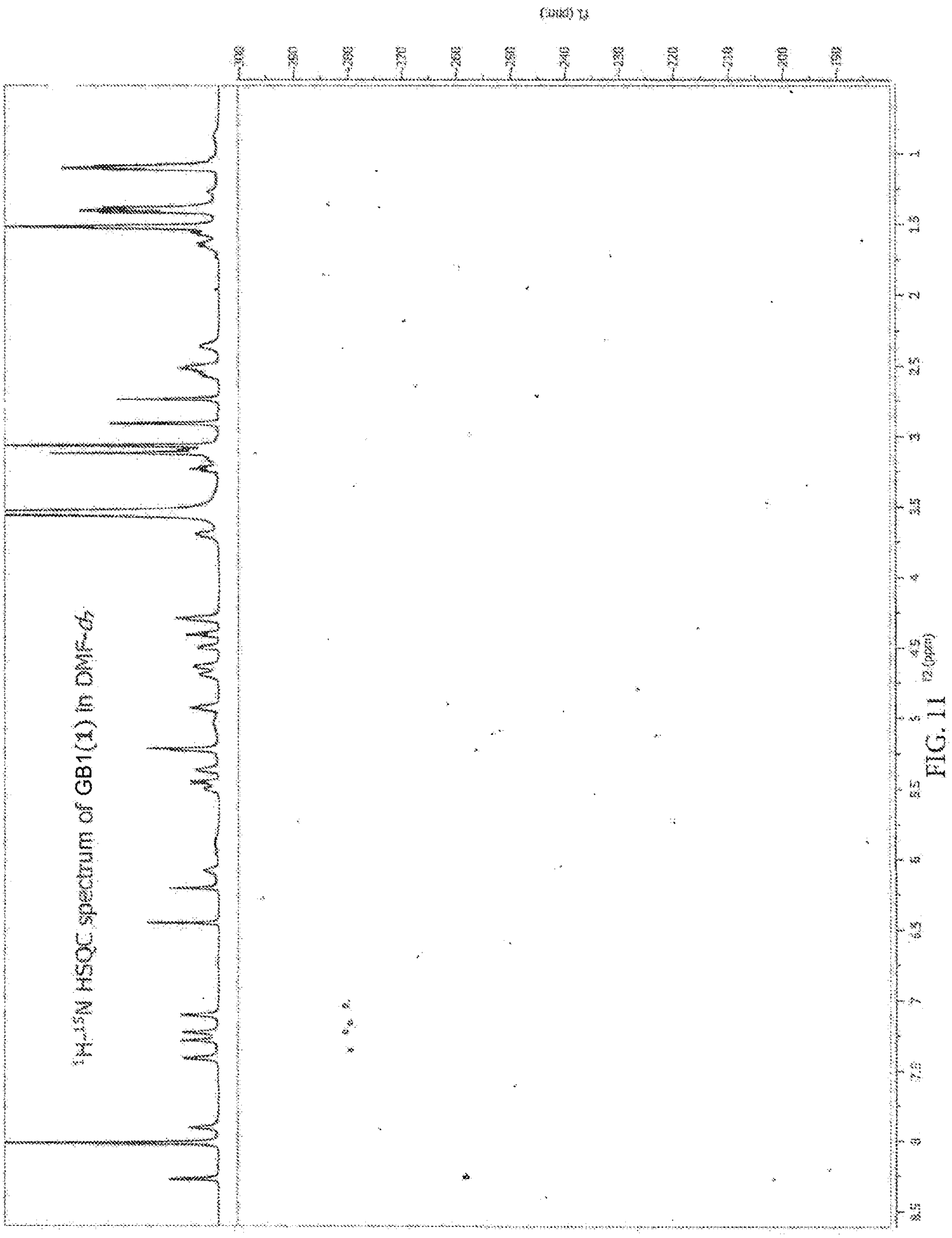
FIG. 11 depicts an exemplary $^1H$-$^{15}N$ HSQC spectrum of GB1 (1) in DMF-$d_7$.
Figure 12:
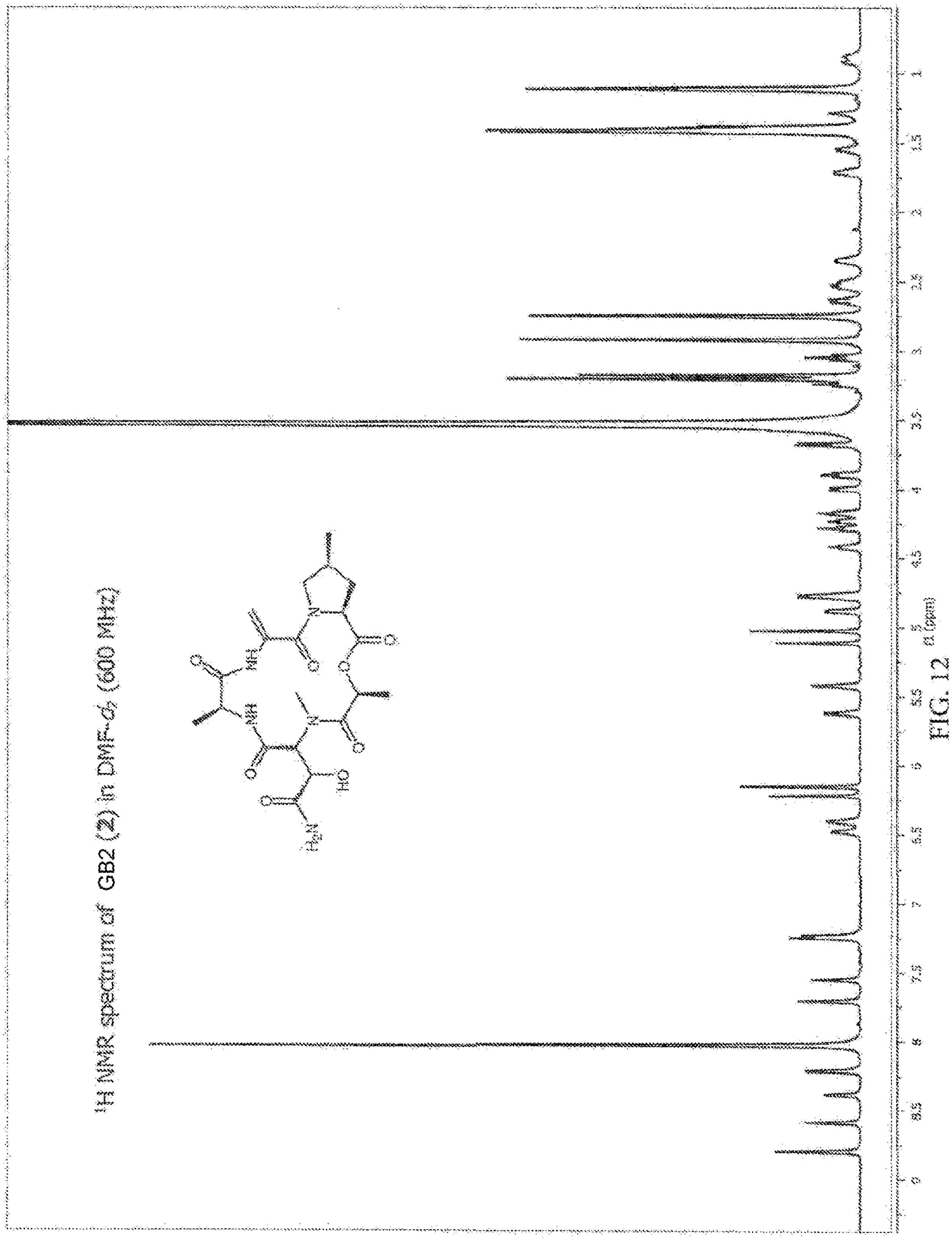
FIG. 12 depicts an exemplary $^1H$ NMR spectrum of GB2 (2) in DMF-$d_7$ (600 MHz).
Figure 13:
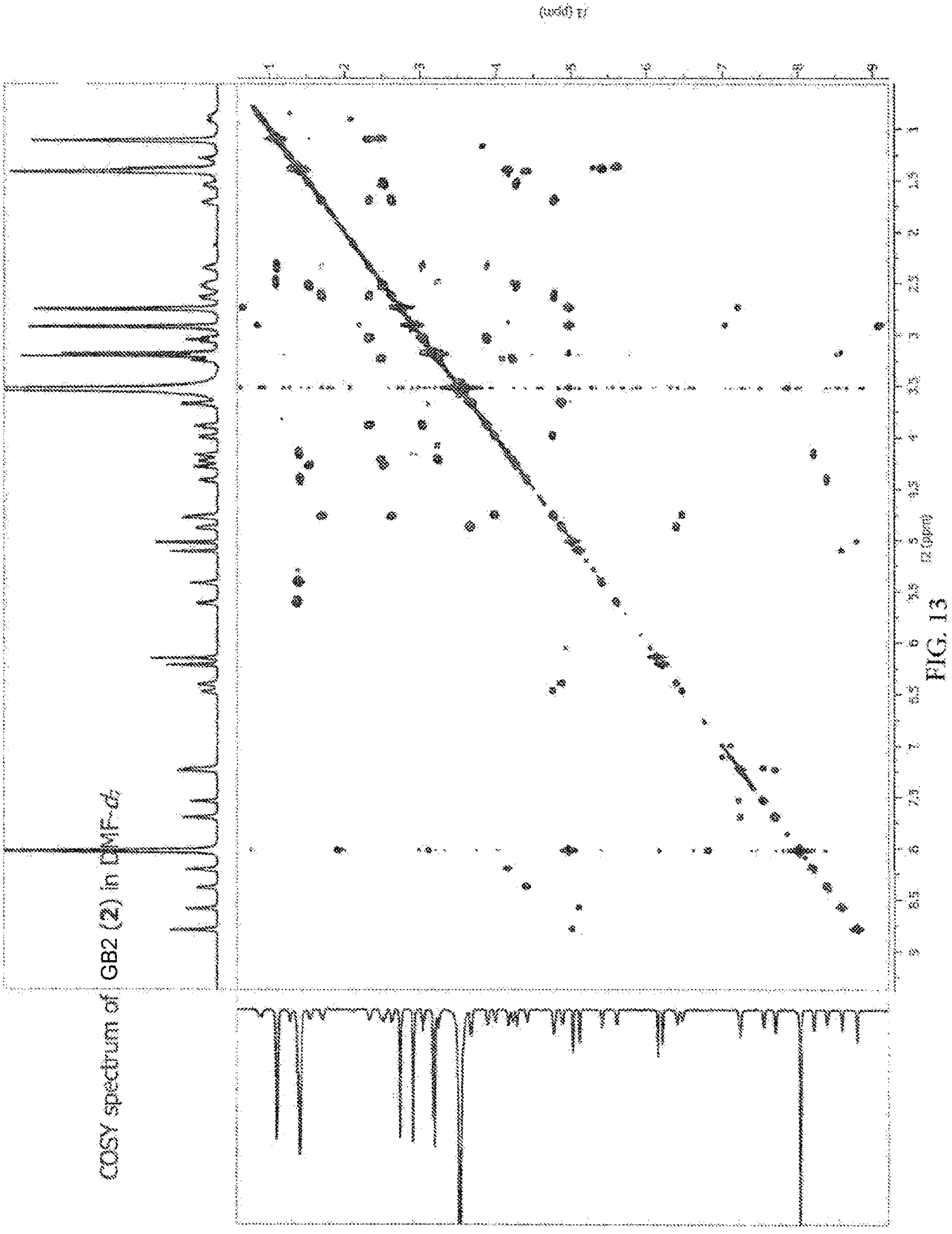
FIG. 13 depicts an exemplary COSY spectrum of GB2 (2) in DMF-$d_7$.
Figure 14:
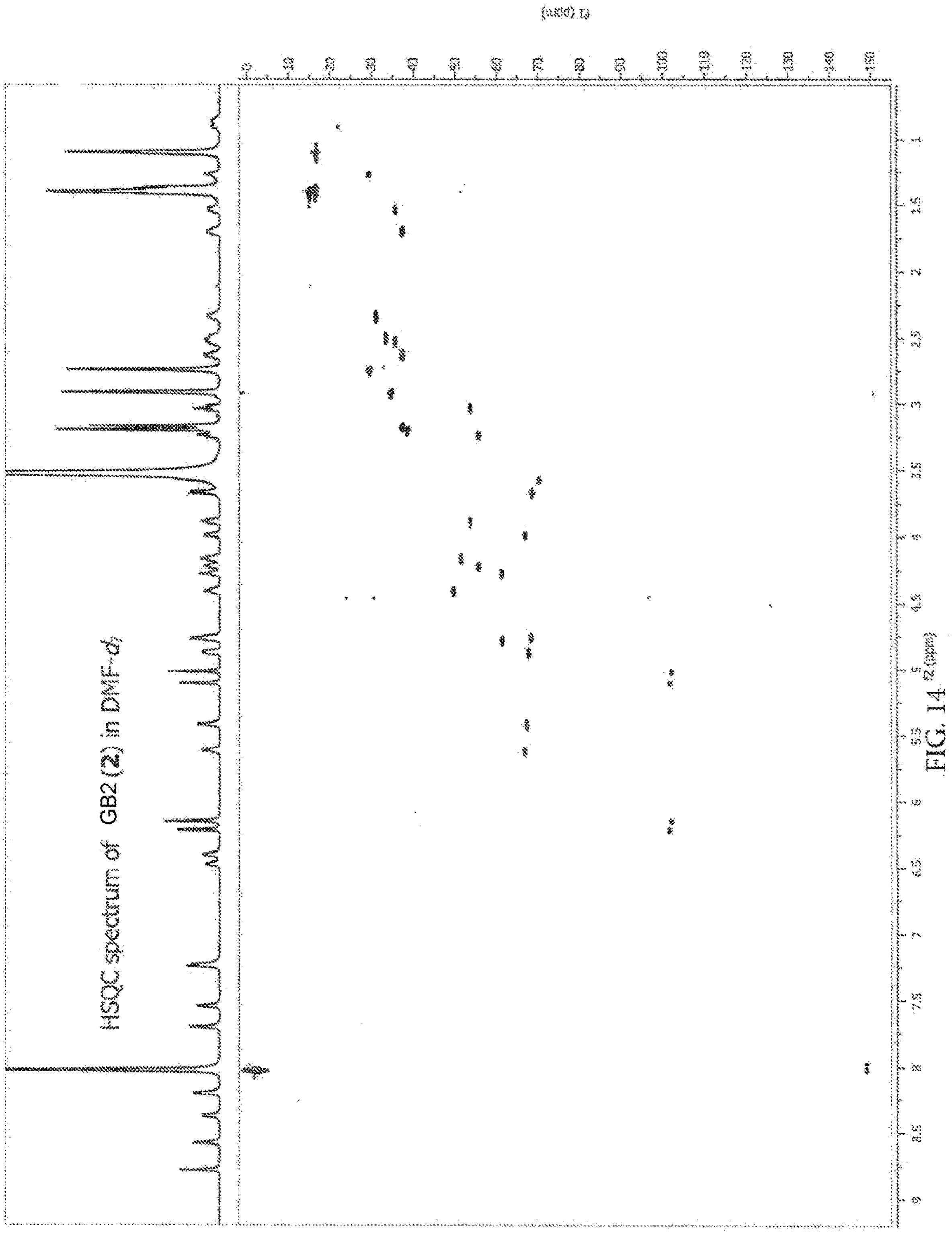
FIG. 14 depicts an exemplary HSQC spectrum of GB2 (2) in DMF-$d_7$.
Figure 15:
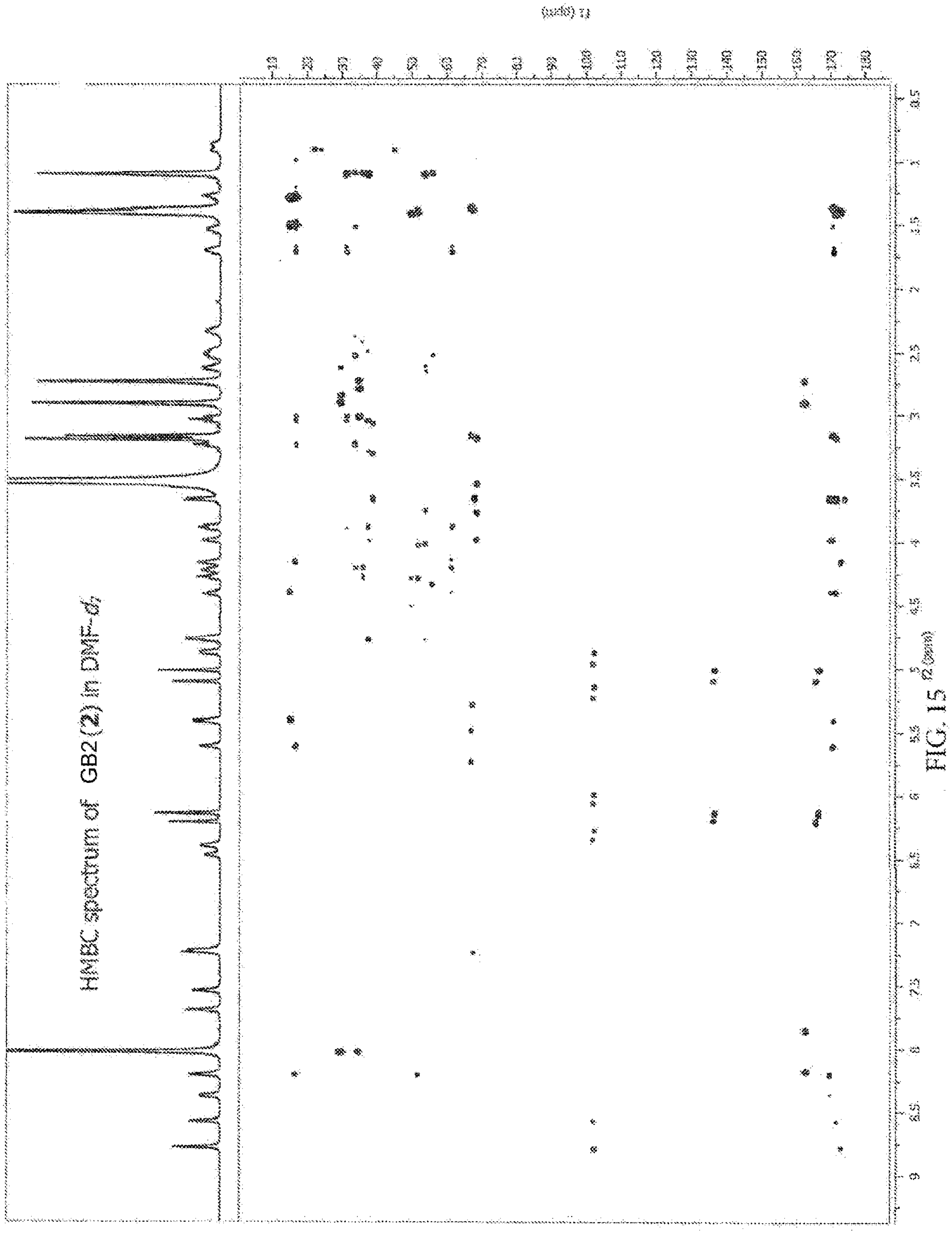
FIG. 15 depicts an exemplary HMBC spectrum of GB2 (2) in DMF-$d_7$.
Figure 16:
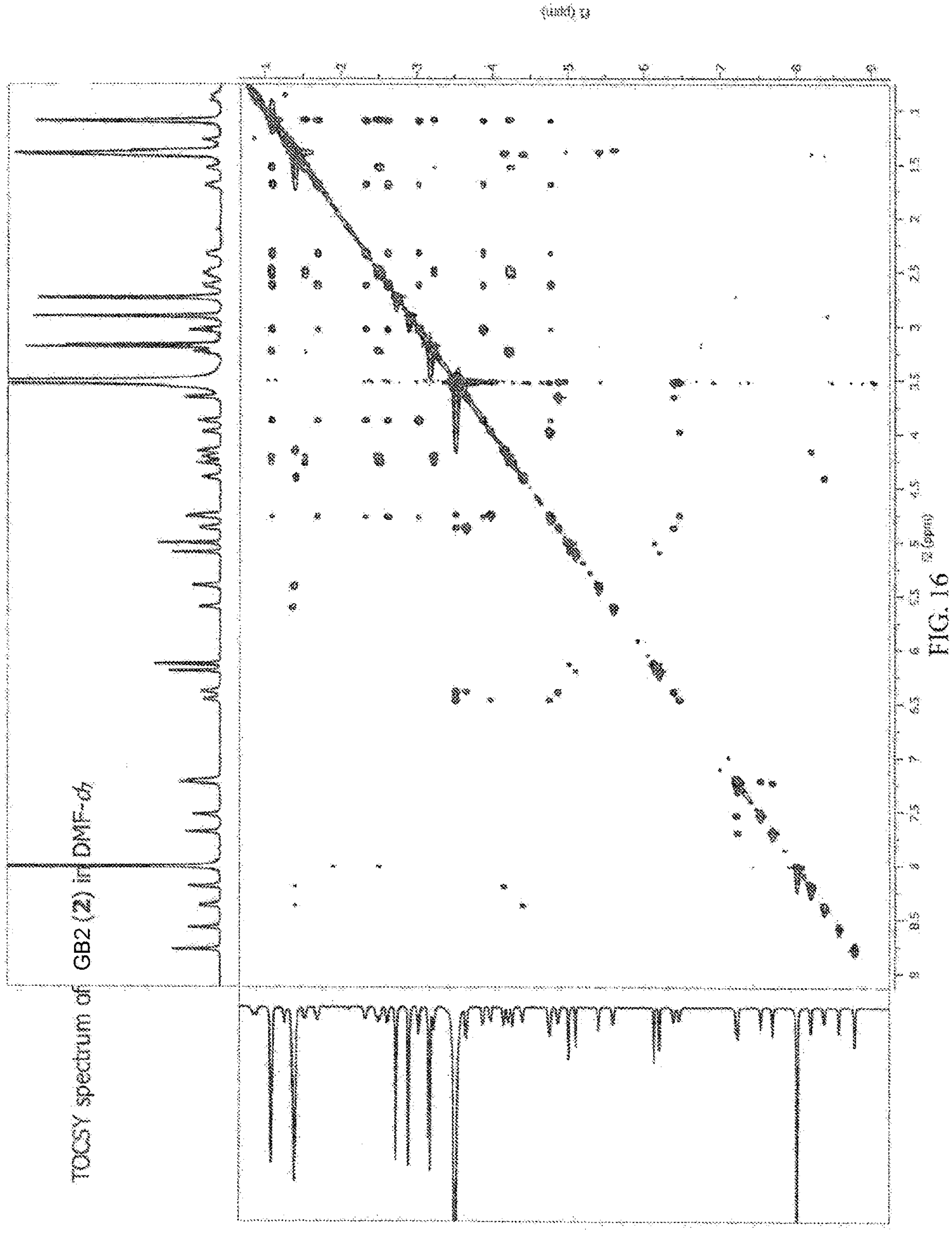
FIG. 16 depicts an exemplary TOCSY spectrum of GB2 (2) in DMF-$d_7$.
Figure 17:
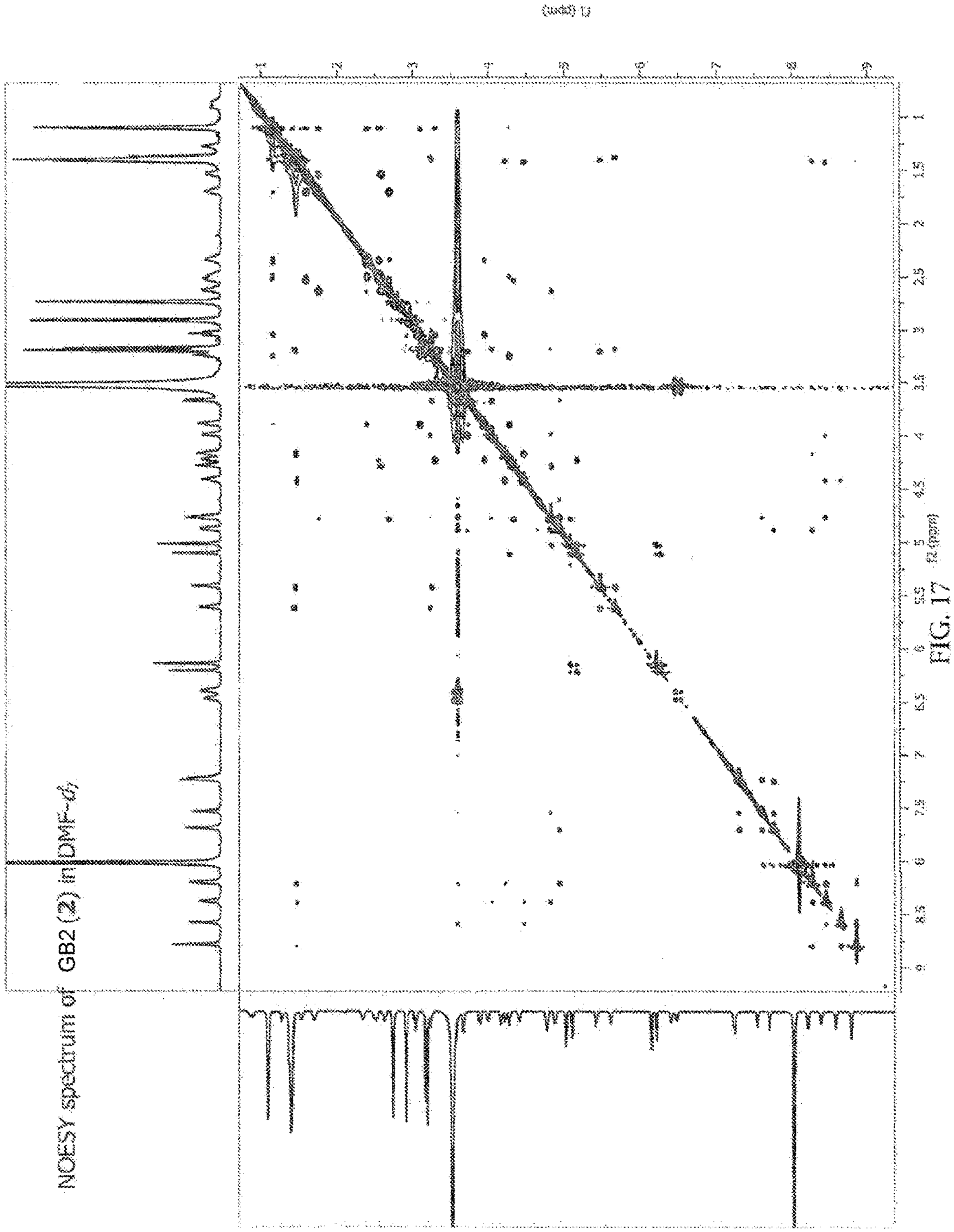
FIG. 17 depicts an exemplary NOESY spectrum of GB2 (2) in DMF-$d_7$.

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of -sheet and a-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 μg/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 pM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 μg/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from 0, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from 0, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)$CF_3$), sulfonates (e.g., mesyl, tosyl), acetamides (e.g., —NHC(O)Me), carbamates (e.g., N(Me) C(O)Ot-Bu), phosphonates (e.g., —OP(O)(OEth), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, $2^{nd}$ *Edition*, Carlson R, Ed, 2005; Elsevier Science Ltd.; Jahnisch, Ket al, Angew. Chem. Int. Ed. Engl. 2004_43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cisltrans and EIZ isomers are expressly included in the present invention. The compounds herein may also be represented in multiple tautomeric forms, in such instances, the invention expressly includes all tautomeric forms of the compounds described herein, even though only a single tautomeric form may be represented. While compounds may be depicted as racemic or as one or more diastereoisomers, enantiomers, or other isomers, all such racemic diastereoisomer, enantiomer, or other isomer forms of that depicted are included in the present disclosure. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

In one aspect, the invention provides a method of modulating the proliferation activity of a cell in a subject, comprising contacting the subject with a compound of formula I, in an amount and under conditions sufficient to modulate cell proliferation activity.

In one embodiment, the modulation is inhibition.

In another aspect, the invention provides a method of treating a subject suffering from or susceptible to a cell proliferation related disorder or disease, comprising administering to the subject an effective amount of a compound or pharmaceutical composition of formula I.

In other aspects, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of formula I, such that said subject is treated for said disorder.

In certain embodiments, the invention provides a method as described above, wherein the compound of formula I is GB1.

In certain embodiments, the invention provides a method of treating a disorder, wherein the disorder is cancer (e.g., breast, colon) or solid tumor.

In certain embodiments, the subject is a mammal, preferably a primate or human

In another embodiment, the invention provides a method as described above, wherein the effective amount of the compound of formula I ranges from about 0.005 μg/kg to about 200 mg/kg. In certain embodiments, the effective amount of the compound of formula I ranges from about 0.1 mg/kg to about 200 mg/kg. In a further embodiment, the effective amount of compound of formula I ranges from about 10 mg/kg to 100 mg/kg.

In other embodiments, the invention provides a method as described above wherein the effective amount of the compound of formula I ranges from about 1.0 pM to about 500 μM. In other embodiments, the invention provides a method as described above wherein the effective amount of the compound of formula I ranges from about 1.0 pM to about 500 nM. In certain embodiments, the effective amount ranges from about 10.0 pM to about 1000 pM. In another embodiment, the effective amount ranges from about 1.0 nM to about 10 nM. In certain embodiments, the effective amount ranges from about 10.0 pM to about 50 μM. In another embodiment, the effective amount ranges from about 1.0 nM to about 50 μM. In certain embodiments, the effective amount ranges from about 10.0 pM to about 10 μM. In another embodiment, the effective amount ranges from about 1.0 nM to about 10 μM. In certain embodiments, the effective amount ranges from about 0.01 μM to about 10 μM. In another embodiment, the effective amount ranges from about 0.1 μM to about 10 μM.

In another embodiment, the invention provides a method as described above, wherein the compound of formula I is administered intravenously, intramuscularly, subcutaneously, intracerebroventricularly, orally or topically.

In other embodiments, the invention provides a method as described above, wherein the compound of formula I is administered alone or in combination with one or more other therapeutics. In a further embodiment, the additional therapeutic agent is an anti-cancer agent, chemotherapeutic agent, an anti-angiogenesis agent, cytotoxic agent, or an anti-proliferation agent. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, The Merck Manual of Diagnosis and Therapy, 15th Ed., pp. 1206-1228, Berkow et al., eds., Rahay, N.J., 1987).

In another embodiment, the invention provides a method as described herein wherein the compound of formula I demonstrates selectivity (e.g., at least 2-fold, at least at least 10-fold, at least X-fold where X is any number between 1 and 20 inclusive) in cell growth activity (e.g., in transformed versus nontransformed cells).

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Another object of the present invention is the use of a compound as described herein (e.g., of any formulae herein) in the manufacture of a medicament for use in the treatment of a cell proliferation disorder or disease. Another object of the present invention is the use of a compound as described herein (e.g., of any formulae herein) for use in the treatment of a cell proliferation disorder or disease.

Pharmaceutical Compositions

In one aspect, the invention provides a pharmaceutical composition comprising the compound of formula I and a pharmaceutically acceptable carrier.

In one embodiment, the invention provides a pharmaceutical composition wherein the compound of formula I is GB1, and a pharmaceutically acceptable carrier.

In another embodiment, the invention provides a pharmaceutical composition further comprising an additional therapeutic agent. In a further embodiment, the additional therapeutic agent is an anti-cancer agent, chemotherapeutic agent, an anti-angiogenesis agent, cytotoxic agent, or an anti-proliferation agent.

In one aspect, the invention provides a kit comprising an effective amount of a compound of formula I, in unit dosage form, together with instructions for administering the compound to a subject suffering from or susceptible to a cell proliferation disease or disorder, including cancer, solid tumor, angiogenesis, etc.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific organozinc compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment f herein includes that embodiment as any single embodiment or in combination with any other embodiments or portions thereof.

EXAMPLES

The present invention will now be demonstrated using specific examples that are not to be construed as limiting.

A. Synthesis and Characterization

General Experimental Procedures

Natural products analysis. Optical rotation was measured on a Perkin-Elmer 341 polarimeter. UV spectra were recorded on a SpectraMax M5 (Molecular Devices). IR spectrum was obtained on a Bruker Vector 22 spectrometer. $^{1}$H NMR and 2D NMR data for GB1 (1a) and GB2 (1b) were initially recorded on a Bruker Avance II 600 MHz spectrometer, operating at 600 MHz ($^{1}$H) and 150 ($^{13}$C), using DMF-$d_7$ as solvent (referenced to $\delta_H$ 8.02, $\delta_C$ 162.9 for residual solvent signals). The instrument was equipped with a 1-mm triple resonance high-temperature superconducting cryogenic probe for 1b analysis[1]. HMQC and HSQC experiments for GB1 (1a) and GB2 (1b) were optimized for $^{1}J_{CH}$=145 Hz, and $^{1}$H-$^{13}$C HMBC experiments for both were optimized for $^{n}J_{CH}$=7 Hz. $^{1}$H-$^{15}$N HMBC NMR data for 1a was obtained on a Varian Unity Inova 500 spectrometer. HRMS data were obtained using an Agilent LC-TOF mass spectrometer equipped with an APCI/ESI multimode ion source detector. LRMS data were obtained using a 3200 Q TRAP LC/MS/MS (hybrid triple quadrupole linear ion trap mass spectrometer, Applied Biosystems) with an electrospray ionization (ESI) interface operated in positive mode. UV spectra were measured on a SpectraMax M5 (Molecular Devices).

Synthesis. All commercial reagents were used without further purification unless otherwise noted. Solvents were purified by PS-MD-5 solvent purification system (Innovative Technology Inc., now Inert Corp.). All reactions were performed in heat-gun dried flasks (400° C. under reduced pressure) under an inert atmosphere of anhydrous Ar unless otherwise noted. Thin layer chromatography was performed on EMD silica gel 60 Å $F_{254}$ glass plates sand preparative thin layer chromatography was performed on Whatman silica gel 60 Å $F_{254}$ glass plates (layer thick 1000 μm). Reversed-phase thin layer chromatography was performed on MilliporeSigma 60 RP-18 F254 s glass plate. Flash column chromatography was performed with Fisher 170-400 mesh silica gel. NMR spectra were recorded on a Bruker Avance III 600 MHz spectrometer or a Bruker Avance Neo-600 spectrometer with a broadband Prodigy cryogenic probe. Chemical shifts for $^{1}$H and $^{13}$C NMR spectra are reported in parts per million relative to the signal residual signal ($CDCl_3$: 7.26 ppm/77.16 ppm; $D_2O$ 4.79 ppm; DMF-$d_7$ 8.02 ppm/163.15 ppm). Optical rotation was measured on a Perkin-Elmer 341 polarimeter (Na D line) using a micro-cell of 1 dm path length. HRMS was conducted using a Thermo Fisher Q Exactive Focus mass spectrometer equipped with UltiMate™ 3000 RSLCnano System and electrospray probe on Universal Ion Max API source.

The abbreviations s, d, dd, ddd, dddd, t, q, p, br, and m stand for the NMR multiplicity singlet, doublet, doublet of doublets, doublet of doublet of doublets, doublet of doublet of doublet of doublets, triplet, quartet, pentet, broad and multiplet, respectively.

Isolation and Structure Determination

Extraction and Isolation. Samples of *Lyngbya* cf. *confervoides* were collected off the coast of Broward County (26°01.1414'N, 80°05.9973'W, 26°15.134'N, 80°03.908'W) at a depth of 7-15 meters in July 2004 and August of 2005.

A voucher specimen is retained at the Smithsonian Marine Station. The freeze-dried organism was extracted with EtOAc-MeOH (1:1) to afford the lipophilic extract, VP56L (3.4 g). VP56L was applied to Diaion HP-20 polymeric resin and subsequently fractionated with water and increasing concentration of acetone. The fraction eluting with 50% aqueous acetone (80 mg) was applied to a $C_{18}$ Alltech SPE cartridge and elution initiated with $H_2O$ followed by aqueous MeOH was then purified by semipreparative reversed-phase HPLC (YMC-Pack ODS-AQ, 250×10 mm, 2.0 mL/min; UV detection at 220 and 240 nm) using a MeOH—$H_2O$ linear gradient (20-100% over 70 min and then 100% MeOH for 10 min) to furnish compound 1a, $t_R$ 31.0 min (1.0 mg).

The same organism was recollected in 2006 during a cyanobacterial bloom, which was freeze-dried and extracted with EtOAc-MeOH (1:1) to afford a crude extract. The extract was suspended in water and defatted with hexanes and further partitioned between n-BuOH and $H_2O$. The combined n-BuOH extract (6.3 g) was applied on a Diaion HP-20 resin and subsequently fractionated with water and increasing concentrations of MeOH, and then with MeCN. The combined fractions eluting between 25-50% aqueous MeOH (350 mg) were subjected to reversed-phase preparative HPLC (Phenomenex Luna-C18 10μ, 100×21.2 mm, 10 mL/min, UV detection at 220 and 240 nm) using a MeOH—$H_2O$ linear gradient (10-55 in 20 min and 55-100% MeOH for 10 min) to afford compound 1a ($t_R$ 16.2 min, 2.0 mg). A fraction with minor peaks eluting between $t_R$ 13.4-15.8 min was also collected and subjected to repeated semipreparative reversed-phase HPLC (YMC-Pack ODS-AQ, 250×10 mm, 2.0 mL/min; UV detection at 220 and 240 nm) using a MeOH—$H_2O$ linear gradient (25-75% in 20 min, 75-100% in 10 min) to give compound 1b ($t_R$ 18 min, ~0.2 mg).

Gatorbulin-1 (1a). Colorless, amorphous solid; $[\alpha]^{20}_D$−84.0 (c 0.10, MeOH); UV (MeOH) $\lambda_{max}$ (log ε) 209.8 (4.07) nm; IR (film) $\nu_{max}$ 3500, 1742, 1672, 1522, 1447, 1267, 1078 $cm^{-1}$; $^1H$ NMR, $^{13}C$ NMR, COSY, and HMBC data, see Table 1; HRESI/APCIMS m/z $[M+H]^+$ 484.2043 (calcd for $C_{24}H_{29}N_5O_9$, 484.2044).

Gatorbulin-2 (1b). Colorless, amorphous solid; $[\alpha]^{20}_D$−62.0 (c 0.008, MeOH); UV (MeOH) $\lambda_{max}$ (log ε) 210.0 (4.07) nm; $^1H$ NMR, $^{13}C$ NMR, COSY, HMBC, and NOESY data, see Table S1; HRESI/APCIMS m/z $[M+H]^+$ 468.2080 (calcd for $C_{20}H_{19}N_5O_8$, 468.2094).

Acid Hydrolysis and Chiral HPLC Analysis of Gatorbulin-1 (1a)

A sample of compound 1a (0.5 mg) was dissolved in 6 N HCl (0.5 mL) and heated at 110° C. for 24 h. The hydrolyzate was concentrated to dryness, re-suspended in $H_2O$ (100 μL), filtered and subjected to chiral HPLC analysis (Phenomenex Chirex 3126 N,S-dioctyl-(D)-penicillamine, 250 mm×4.60 mm, 5 μm; solvent, 2 mM $CuSO_4$ or 2 mM $CuSO_4$-MeCN (95:5); flow rate, 1.0 mL/min; UV detection 254 nm). The absolute configurations of the amino acid units in 1a were established as L-Lac (38.5), (2S,4S)-4-Me-Pro (66.0) (solvent 2 mM $CuSO_4$); L-Lac (18.4), (2S,4S)-4-Me-Pro (19.8) (solvent 95:5) by comparison of the retention times $t_R$ (min) with those of standard amino acids. The retention times $t_R$ (min) for the other standard amino acid isomers were D-Lac (51.0) (solvent 2 mM $CuSO_4$); D-Lac (22.7), (2S,4R)-4-Me-Pro (17.5), (2R,4S)-4-Me-Pro (38.0), (2R,4R)-4-Me-Pro (40.0) (solvent 95:5).

Determination of Absolute Configuration of Gatorbulin-1 (1a) by Advanced Marfey's Analysis A portion of the hydrolysis product from 1a was treated with 1 M $NaHCO_3$ (10 μL) and a 1% solution of either L- or DL-FDLA (1-fluoro-2,4-dinitrophenyl-5-leucinamide) in acetone and heated at 80° C. for 3 min. The solutions were cooled, neutralized with 2 N HCl (5 μL), dried and dissolved in $H_2O$-MeCN (1:1) and subjected to reversed-phase HPLC (Alltech Altima phenyl 5 u, 250×4.6 mm; flow rate, 1 mL/min; PDA detection from 200-500 nm) using a linear gradient of MeOH in 0.1% aqueous HCOOH (20-40% for 20 min, 40-100% for 40 min). The retention times ($t_R$, min) of the L-FDLA derivatized amino acids in the hydrolyzate of 1a matched with those of L-erythro-N-Me-β-OH-Asp ((2S, 3R)-3-OH—N-Me-Asp) (19.58), and (2S,4S)-4-Me-Pro (24.0) and not that of L/D-threo-N-Me-β-OH-Asp (17.50, 18.28), D-erythro-NMe-β-OH-Asp (19.40).

Reduction of 1a to 1b. 1 mg of compound 1a was dissolved in 2 mL of THF under argon. Then 1 mL of 4.5 M aqueous ammonium acetate followed by 0.5 mL of a 10% $TiCl_3$ solution in 20-30 wt. % HCl was added to the solution. The mixture was stirred at room temperature for 3 h. The product was extracted with THF (3×3 mL) and the organic layer was subsequently washed with saturated $NaHCO_3$ (10 mL) and brine (10 mL) solutions. The reduction product (1b) was purified by reversed-phase HPLC (Phenomenex Luna, ODS 250×10 mm, 5 micron, 2.0 mL/min; PDA detection) using a MeOH—$H_2O$ linear gradient (40-100% MeOH for 30 min). The peak eluted at 11.7 min was identified as 1b by low resolution ESI-MS m/z [M+H]+468.4. Equal amounts of starting material (1a) was also (12.1 min) detected by HPLC.

Chiral HPLC analysis of reduction product 1b. The reduction product thus obtained was hydrolyzed with 6 N HCl for 16 h at 116° C. A portion of hydrolyzate was analyzed by ESI-LC-MS-MS in the positive mode, using multiple reaction monitoring (MRM). HPLC conditions: Astec Supelco Chirobiotic TAG column, 250 mm×4.60 mm, 5 mm; solvent, 10 mM Ammonium acetate-MeOH, (60:40, pH~5.3); flow rate 0.5 mL/min. The optimized MS instrument conditions were as follows: source temperature, 750° C.; curtain gas, 50 psi; nebulizer gas (GS1), 65 psi; turbo gas (GS2), 65 psi; collision energy (CE), 17.4 V. The following precursor and product ion transitions were used for multiple reaction monitoring: L and D-alanine, 90→44, and compared with Ala standards. L-Ala (9.3 min) was detected in the reduction product hydrolyzate but not D-Ala (18.1 min), verifying the configuration of the N—OH-Ala unit as L in 1a.

Synthesis of N-Me-β-Hydroxyaspartic Acids (Scheme S1)

Scheme S1. Synthesis of N-Me-β-hydroxyaspartic acids.

a. Hydrolysis and aminolysis of optically pure compounds

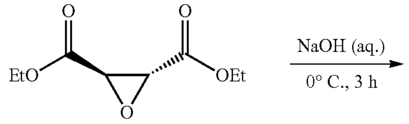

(2R,3R)-diethyl-2,3-epoxysuccinate

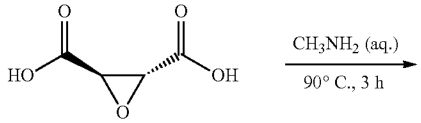

(2R,3R)-epoxysuccinic acid

-continued

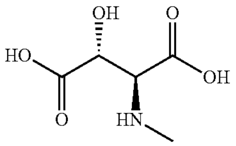

(2R,3R)-3-OH-N-Me-Asp
(erythro-3-OH-N-Me-Asp)

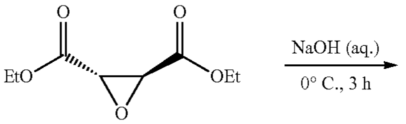

(2S,3S)-diethyl-2,3-epoxysuccinate

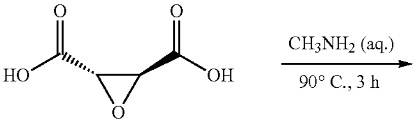

(2S,3S)-epoxysuccinic acid

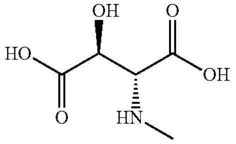

(2R,3S)-3-OH-N-Me-Asp
(threo-3-OH-N-Me-Asp)

b. Aminolysis of trans/cis mixture

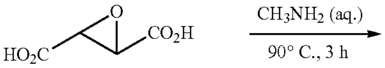

(+/-) trans-epoxysuccinic acid

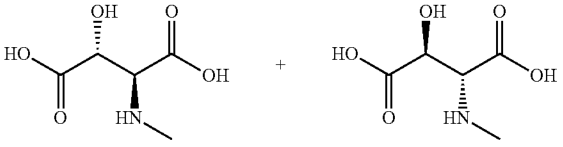

(2R,3R)-3-OH-N-Me-Asp
(erythro-3-OH-N-Me-Asp)

(2R,3S)-3-OH-N-Me-Asp
(threo-3-OH-N-Me-Asp)

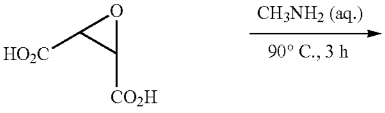

(+/-) cis-epoxysuccinic acid

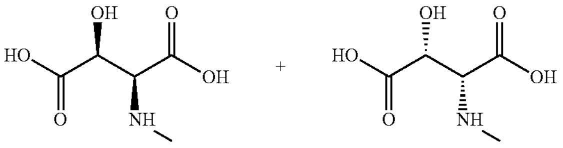

(2S,3S)-3-OH-N-Me-Asp (2R,3R)-3-OH-N-Me-Asp

Enantiometrically pure L- and D-isomers of N-Me-β-hydroxyaspartic acids were obtained by saponification of corresponding diethyl-2,3-epoxysuccinate (Scheme S1a) as described below. A solution of aqueous NaOH (40 mg, 2 eq.) was added to (2R,3R)-diethyl-2,3-epoxysuccinate (94 mg, 1 eq.) in an ice bath. The resulting solution was stirred for 2 h at 0° C., then for 30 min at room temperature, after which the solution was neutralized and dried to yield (2R,3R)-2,3-epoxysuccinic acid. $^1H$ NMR (400 MHz, $D_2O$): δ 3.19 (s, 2H); $^{13}C$ NMR (100 MHz, $D_2O$): δ 175.3. 53.9.

100 mg (0.5 mmol) of (2R,3R)-2,3-epoxysuccinic acid was heated under reflux with concentrated methylamine (41% aq., 2 mL) for 3 h to afford L-erythro-N-Me-β-OH-Asp ((2S,3R)-3-OH—N-Me-Asp) (0.47 mmol, 94% overall yield). $[\alpha]^{20}_D$+26.0 (c 0.24, $H_2O$); $^1H$ NMR (400 MHz, $D_2O$): δ 4.36 (d, J=2.4, 1H), 3.84 (d, J=2.4 Hz, 1H), 2.78 (s, 3H) ppm; $^{13}C$ NMR (100 MHz, $D_2O$): δ 170.2, 170.4, 69.9, 66.3, 32.3 ppm.

Similarly (2S,3S)-diethyl-2,3-epoxysuccinate (55 mg, 0.3 mmol) was treated as described above to yield D-erythro-N-Me-β-OH-Asp ((2R,3S)-3-OH—N-Me-Asp) (0.39 mmol, 100% overall yield). $[\alpha]^{20}_D$−15.0 (c 0.20, $H_2O$); $^1H$ NMR (400 MHz, $D_2O$/1,4 Dioxane): δ 4.61 (d, 1H, J=2.8), 4.06 (d, 1H, J=2.8 Hz), 2.82 (s, 3H) ppm. $^{13}C$ NMR (100 MHz, $D_2O$): δ 175.3, 170.1, 69.2, 65.7, 32.5 ppm.

N-Me-DL-(erythro/threo)-β-hydroxyaspartic acid has been prepared by conversion of corresponding (+/−)-(trans/cis)-epoxysuccinic acid with concentrated solutions of aqueous methylamine to yield L/D-threo-N-Me-β-OH-Asp and L/D-erythro-N-Me-β-OH-Asp, respectively (Scheme S1b).

Similarly, L/D-threo-N-Me-β-OH-Asp was obtained from (+/−)-cis-epoxysuccinic acid as colorless amorphous powder (88% yield). $^1H$ NMR (400 MHz, $D_2O$/1,4 Dioxane): δ 4.51 (d, 1H, J=2.2), 3.93 (d, 1H, J=2.2 Hz), 2.70 (s, 3H) ppm. L/D-erythro-N-Me-β-OH-Asp was obtained as colorless amorphous powder (92% yield). $^1H$ NMR (400 MHz, $D_2O$/1,4 Dioxane): δ 4.62 (d, J=3.0, 1H), 4.07 (d, J=3.0 Hz, 1H), 2.80 (s, 3H) ppm. $^{13}C$ NMR (100 MHz, $D_2O$): δ 174.7, 169.8, 68.8, 65.3, 32.4 ppm.

Total Synthesis of Gatorbulin-1 (1a)

Scheme S2. Synthesis of building block 4.

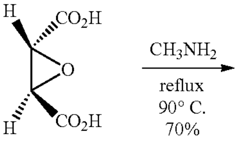

10

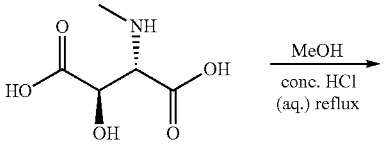

11

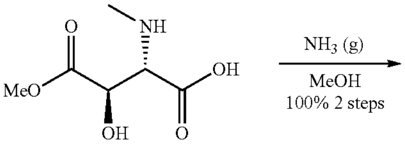

12

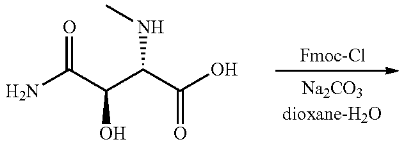

13

-continued

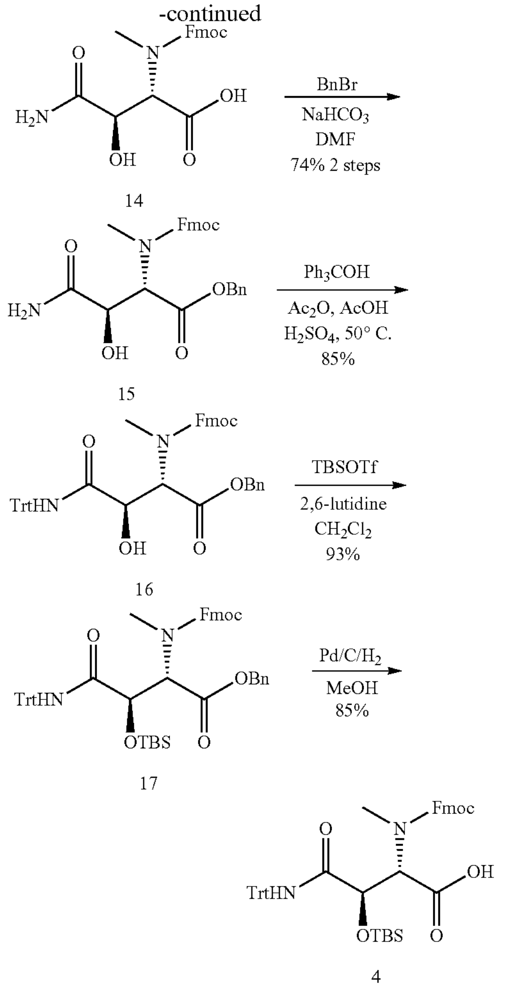

(2S,3R)-3-Hydroxy-N-methylaspartic acid[2] (11). Methylamine water solution (41%) (100 mL) was added to solid of (2R,3R)-epoxysuccinic acid (10) (6.0 g, 45.43 mmol) at 0° C. The mixture was stirred for 4.5 h under refluxing (75-80° C.), then cooled down to room temperature and concentrated under reduced pressure. Water (3×15 mL) was added to the concentrated residue and evaporated again for three times to remove unreacted methylamine. The crude product was purified by column of Dowex ($H^+$) resin, eluted by deionized water and then 4 M aqueous ammonia to provide product 11 (6.7 g, 90%). $^1$H NMR (400 MHz, $D_2O$): δ 4.64 (d, J=2.8 Hz, 1H), 4.10 (d, J=3.2 Hz, 1H), 2.78 (s, 3H) ppm. HRMS (ESI) m/z calcd for $C_5H_9NO_5$ $(M+H)^+$ 164.0559, found 164.0550.

(2S,3R)-3-Hydroxy-N-methylaspartic acid β-methyl ester (12). Concentrated chloric acid (1.7 mL, 12 M) was added to the solution of compound 11 (1.649 g) in MeOH (50 mL) and the reaction mixture was refluxed for 3 h. The resulting mixture was concentrated under reduced pressure. MeOH (3×20 mL) was added to the concentrated residue and evaporated again for three times to remove excess chloric acid. The crude product was dried by oil pump to provide product 12 (1.73 g, 100%) as white foam. $^1$H NMR (400 MHz, $D_2O$): δ 4.87 (d, J=2.4 Hz, 1H), 4.44 (d, J=2.8 Hz, 1H), 3.80 (s, 3H), 2.83 (s, 3H) ppm. $^{13}$C NMR (100 MHz, $CDCl_3$): δ 171.9, 168.0, 67.4, 63.0, 53.2, 31.6 ppm. HRMS (ESI) m/z calcd for $C_6H_{11}NO_5$ $(M+H)^+$ 178.0715, found 178.0712.

(2S,3R)-3-hydroxy-$N_\alpha$-methyl-asparagine (13). Compound 12 (1.7 g, 10.49 mmol) was dissolved in anhydrous MeOH (40 mL). The resulting solution was saturated (bubbled) with ammonia (gas) for 5-7 min each day (total 3 days). After stirring for three days, the reaction solution was evaporated to dryness in vacuo. The resulting solid was washed with cold methanol, then diethyl ether and to give the compound 13 as a white solid (1.60 g, 95%). $[\alpha]^{20}_D$: +27 (c 0.09, $H_2O$). $^1$H NMR (600 MHz, $D_2O$, mixtures of rotamers): δ 4.61 (br m, 1H), 4.00 (br m, 1H), 2.82 (s, 1H) ppm. $^{13}$C NMR (150 MHz, $D_2O$, mixtures of rotamers): δ 175.4, 169.2, 68.7, 65.1, 32.0 ppm. HRMS (ESI) m/z calcd for $C_5H_{10}N_2O_4$ $(M+H)^+$ 163.0719, found 163.0710.

(2S,3R)-3-Hydroxy-$N_\alpha$-methyl-$N_\alpha$-Fmoc-asparagine (14). 9-Fluorenylmethyl chloroformate (Fmoc-Cl) (2.945g, 11.386 mmol) and $Na_2CO_3$ (2.413 g, 22.767 mmol) were dissolved in the solution of the mixture of 1,4-dioxane and water (45 mL-45 mL). Compound 13 (1.23 g, 7.589 mmol) was added to the above solution at 0° C. ant stirred 10 min at this temperature. After the reaction mixture was moved to room temperature and stirred at this temperature overnight, it was diluted with water (80 mL) and concentrated under reduced pressure to move most of 1,4-dioxane. The concentrated mixture was extracted with diethyl ether (20 mL×4). The water layer was acidified with 2M HCl (aq.) to pH 2 and extracted with EtOAc (150 mL×3). The combined organic phase was dried with anhydrous $MgSO_4$ and evaporated in vacuo to give product 14 (2.393 g, 82%). $[\alpha]^{20}_D$: +1.5 (c 0.32, MeOH). $^1$H NMR (400 MHz, $CDCl_3$, mixtures of rotamers): δ 7.68 (d, J=7.7 Hz, 2H), 7.50 (t, J=8.0 Hz, 2H), 7.36-7.30 (br m, 3H), 7.26-7.21 (br m, 3H), 4.86 (s, 1H), 4.49 (s, 1H), 4.36-4.25 (br m, 2H), 4.18-4.12 (br m, 1H), 3.01 (s, 3H) ppm. $^{13}$C NMR (125 MHz, $CDCl_3$): δ 176.2, 171.1, 158.4, 143.8, 143.5, 141.3, 141.3, 72.9, 68.5, 64.6, 47.0, 36.1 ppm. HRMS (ESI) m/z calcd for $C_{20}H_{20}N_2O_6$ $(M+H)^+$ 385.1400, found 385.1385. Usually, compound 14 was used in the next step without further purification and characterization.

(2S,3R)-3-Hydroxy-$N_\alpha$-methyl-$N_\alpha$-Fmoc-asparagine benzyl ester (15). BnBr (2.94 mL, 24.735 mmol) was added to the solution of compound 14 (2.351 g, 6.121 mmol) and $NaHCO_3$ (1.55 g, 18.45 mmol) in anhydrous DMF (45 mL) at 0° C. and was stirred at this temperature for 1 h, room temperature for 20 h. The resulting mixture was quenched with water (100 mL) and was extracted with EtOAc (150 mL×4). The combined organic phase was washed with water (100 mL×4), dried with anhydrous $MgSO_4$, evaporated in vacuo and purified by flash chromatography column on silica gel (eluted by 40-80% ethyl acetate in hexane) to give product 15 (2.14 g, 74%). $[\alpha]^{20}_D$: +2.8 (c 0.12, MeOH). $^1$H NMR (400 MHz, $CDCl_3$, mixtures of rotamers): δ 7.78 (d, J=7.6 Hz, 2H), 7.58 (d, J=7.5 Hz, 2H), 7.42 (t, J=7.5 Hz, 2H), 7.33-7.27 (br m, 7H), 6.83 (s, 1H), 5.96-5.86 (br m, 2H), 5.23-5.15 (m, 2H), 4.76 (br s, 1H), 4.50-4.45 (m, 2H), 4.39-4.35 (m, 1H), 4.24 (t, J=7.0 Hz, 1H), 3.08 (s, 3H) ppm. $^{13}$C NMR (125 MHz, $CDCl_3$): δ 173.7, 167.7, 158.6, 143.9, 143.5, 141.4, 141.3, 135.2, 128.5, 128.4, 128.2, 127.9, 127.9, 127.2, 125.1, 125.0, 120.1, 73.7, 68.5, 67.5, 66.4, 47.1, 37.5 ppm. HRMS (ESI) m/z calcd for $C_{27}H_{26}N_2O_6$ $(M+H)^+$ 475.1869, found 475.1854.

(2S,3R)-3-Hydroxy-$N_\alpha$-methyl-$N_\alpha$-Fmoc-$N_\gamma$-trityl-asparagine benzyl ester (16). Compound 15 (2.443 g, 5.153 mmol) and trityl alcohol (13.414 g, 51.528 mmol) was dissolved in AcOH (17.5 mL). The solution was heated to 50° C. and was treated successively with concentrated sulfuric acid (168 μL, 3.092 mmol) and acetic anhydride (1.22 mL, 12.882 mmol). The reaction mixture was cooled to room temperature after stirred at 50° C. for 2.5 h, then it was diluted with EtOAc (100 mL) and quenched with saturated aqueous $NaHCO_3$ solution (70 mL). Excessive $NaHCO_3$ powder was added slowly to the quenched solution to that there was no bubble ($CO_2$) produced any more. EtOAc layer was separated and the aqueous layer was further extracted with EtOAc, and the combined organic layers were dried ($MgSO_4$), filtered, concentrated in vacuo and purified by flash chromatography column ($SiO_2$, 33% EtOAc in hexane) to provide 16 as a white solid (3.5 g, 95%). $[\alpha]^{20}_D$: +28.4 (c 0.0.48, MeOH). $^1$H NMR (400 MHz, $CDCl_3$): δ 8.23 (s, 1H), 7.79 (d, J=7.6 Hz, 2H), 7.59 (dd, J=7.6, 3.2 Hz, 2H), 7.43 (dd, J=7.6, 7.6 Hz, 2H), 7.35-7.16 (m, 22H), 6.03 (s, 1H), 5.42 (d, J=12.4 Hz, 1H), 5.11 (d, J=12.4 Hz, 1H), 4.72 (br s, 1H), 4.50-4.46 (m, 2H), 4.41-4.36 (m, 1H), 4.26 (dd, J=7.2, 7.2 Hz, 1H), 3.03 (s, 3H) ppm. $^{13}$C NMR (100 MHz, $CDCl_3$): δ 169.1, 167.7, 158.8, 144.8, 144.0, 143.5, 141.5, 141.4, 135.5, 128.8, 128.6, 128.5, 128.4, 128.0, 128.0, 127.2, 127.1, 125.1, 125.1, 120.1, 75.1, 70.2, 68.5, 67.4, 67.2, 47.1, 38.1 ppm. HRMS (ESI) m/z calcd for $C_{46}H_{40}N_2O_6$ $(M+Na)^+$ 739.2748, found 739.2761.

(2S,3R)-3-OTBS-$N_\alpha$-methyl-$N_\alpha$-Fmoc-$N_\gamma$-trityl-asparagine benzyl ester (17). To the solution of 16 (1.48 g, 2.066 mmol) in anhydrous $CH_2Cl_2$ (20 mL) were added 2,6-lutidine (2.4 mL, 20.661 mmol) and tert-butyldimethylsilyl trifluoromethanesulfonate (TBSOTf) (2.37 mL, 10.33 mmol) at 0° C. under argon. After stirring at the same temperature for 20 min, the reaction mixture was moved to room temperature and stirred for another 1 h, then it was quenched with MeOH (10 mL) and saturated aq. $NH_4Cl$ (30 mL), and extracted with EtOAc (50 mL×3). The combined organic layer was washed with 0.5 M HCl (20 mL×3), saturate aq. $NaHCO_3$ (20 mL×2) and brine (20 mL), dried with anhydrous $MgSO_4$ and evaporated in vacuo. The resulting crude mixture was purified by flash chromatography column ($SiO_2$, eluted by 10-12.5% EtOAc in hexane) to give product 17 (1.71 g, 93%) as a white solid. $[\alpha]^{20}_D$+11.6 (c 0.22, MeOH). $^1$H NMR (400 MHz, $CDCl_3$, mixture of rotamers, major and minor (7/3)): δ 7.82 (s, 1H), 7.77 (d, J=7.6 Hz, 1.7H), 7.73-7.70 (m, 1H), 7.57-7.53 (m, 2H), 7.49 (d, J=7.6 Hz, 0.3H), 7.40 (dd, J=7.6, 7.6 Hz, 2H), 7.36-7.11 (m, 21H), 5.30 (d, J=6.8 Hz, 0.7H), 5.19-5.07 (m, 2.3H) 4.73 (d, J=6.8 Hz, 0.7H), 4.63 (d, J=6.0 Hz, 0.3H), 4.58-4.52 (m, 0.3H), 4.37 (dd, J=10.0, 7.2 Hz, 0.7H), 4.29 (dd, J=7.2, 7.2 Hz, 0.7H), 4.23 (dd, J=7.2, 7.2 Hz, 0.7H), 4.11-4.05 (m, 0.6H), 2.83 (s, 3H), 0.81 (s, 9H), 0.15 (s, 2.1H), 0.06 (s, 2.1H), −0.01 (s, 0.9H), −0.02 (s, 0.9H) ppm. $^{13}$C NMR (100 MHz, $CDCl_3$, mixture of rotamers, major and minor (7/3)): δ 169.0, 168.5, 168.1, 157.0, 155.8, 144.4, 144.3, 144.0, 143.9, 141.4, 135.7, 135.5, 128.8, 128.7, 128.6, 128.5, 128.4, 128.3, 128.1, 128.0, 127.8, 127.7, 127.3, 127.2, 127.2, 127.1, 125.3, 125.0, 120.1, 120.0, 73.2, 72.3, 70.6, 70.5, 68.2, 68.0, 67.3, 67.1, 61.9, 61.2, 34.8, 34.6, 32.2, 31.9, 31.7, 25.7, 25.7, 25.4, 22.8, 17.9, 17.9, 14.3, −4.6, −4.7, −5.2, −5.3 ppm. HRMS (ESI) m/z calcd for $C_{52}H_{54}N_2O_6Si$ $(M+H)^+$ 831.3829, found 831.3802.

(2S,3R)-3-OTBS-$N_\alpha$-methyl-$N_\alpha$-Fmoc-$N_\gamma$-trityl-asparagine (4). MeOH (50 mL) was added cautiously to the mixture of compound 17 (1.6 g, 1.927 mmol) and Pd/C (10% wt) (160 mg). The suspension was degassed with argon (balloon) and hydrogen (balloon) successively, then it was stirred under hydrogen gas (balloon) at room temperature for 30 min. The catalyst was removed by filtration through Celite and the filtrate cake was washed by MeOH. The combined filtrate was concentrated in vacuo and purified by flash chromatography column ($SiO_2$, eluted by 2-7% MeOH in $CH_2Cl_2$) to provide product 4 as a white solid (1.21 g, 85%). $[\alpha]^{20}_D$+32.4 (c 0.18, MeOH). $^1$H NMR (400 MHz, $CDCl_3$, mixture of rotamers, major and minor (3/1)): δ 9.03 (br s, 1H), 7.93 (br s, 0.75H), 7.78 (d, J=7.2 Hz, 1.75H), 7.72 (dd, J=7.6, 7.6 Hz, 0.5H), 7.59 (dd, J=6.4, 6.4 Hz, 1.75H), 7.53 (d, J=7.6 Hz, 0.25H), 7.43-7.38 (m, 1.75H), 7.36-7.20 (m, 17.25H), 5.17 (d, J=6.4 Hz, 0.75H), 4.99 (d, J=6.0 Hz, 0.25H), 4.84 (d, J=6.4 Hz, 0.75H), 4.71-4.66 (m, 0.5H), 4.42-4.32 (m, 1.5H), 4.26 (dd, J=7.2, 7.2 Hz, 1H), 4.18-4.10 (m, 0.5H), 2.75 (s, 0.75H), 2.74 (s, 2.25H), 0.87 (s, 6.75H), 0.85 (s, 2.25H), 0.20 (s, 2.25H), 0.16 (s, 2.25H), 0.04 (s, 0.75H), 0.00 (s, 0.75H) ppm. $^{13}$C NMR (100 MHz, $CDCl_3$, mixture of rotamers, major and minor (3/1)): δ 177.2, 172.5, 172.0, 169.3, 169.0, 157.3, 155.9, 144.1, 144.1, 144.0, 143.9, 141.4, 141.3, 128.8, 128.1, 127.8, 127.3, 127.2, 127.1, 125.3, 125.2, 120.0, 72.7, 72.0, 70.5, 68.3, 67.9, 61.8, 61.5, 47.2, 36.2, 34.8, 34.6, 32.5, 32.1, 29.2, 27.0, 25.8, 25.7, 25.4, 20.8, 18.9, 17.9, 14.2, 11.6, −4.7, −5.2 ppm. HRMS (ESI) m/z calcd for $C_{45}H_{48}N_2O_6Si$ $(M+H)^+$ 741.3360, found 741.3341.

Scheme S3. Synthesis of building block 5[2,3]

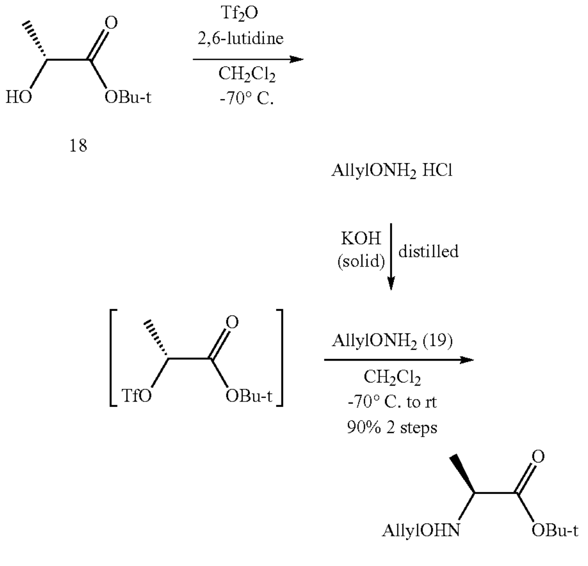

18

5

Allyloxamine (19)[3,4]. Alloxyamine·HCl (6.0 g) was mixed with KOH pellets (15.0 g) in a distillation flask with distillation assembly. The mixture was subjected to distillation by heating at 1 atm under the atmosphere of nitrogen. The product was collected at 86-90° C. as colorless liquid (3.5 g, 88%). $^1$H NMR (400 MHz, $CDCl_3$): δ 5.93-5.83 (m, 1H), 5.37 (br s, 2H), 5.29-5.19 (m, 2H), 1.06 (d, J=6.5 Hz, 2H) ppm. $^{13}$C NMR (100 MHz, $CDCl_3$): δ 134.0, 118.5, 76.8 ppm.

(S)—N-Allyloxyalanine t-butyl ester (5)[3,4]. Triflic anhydride (4.2 mL, 24.981 mmol) was added dropwise to the solution of tert-butyl (R)-lactate (3.044 g, 20.817 mmol) in anhydrous $CH_2Cl_2$ (90 mL) at −70° C. The mixture was stirred 5 min, then 2,6-lutidine (3.044 mL, 26.022 mmol) was added dropwise at the same temperature. After the reaction mixture was stirred at −70° C. for 1.5 h, alloxyamine (19) (3.35 mL, 41.635 mmol) was added dropwise at the same temperature. When the resulting mixture was stirred at −70° C. for another 15 min, it was warmed to room temperature and stirred overnight (about 19 h). The reaction was diluted with $CH_2Cl_2$ (40 mL) and quenched with water (40 mL). The organic layer was washed successively with water (50 mL×2), 2% citric acid (50 mL×2), 5% $NaHCO_3$ (50 mL×2), dried with anhydrous $MgSO_4$, filtered and concentrated in vacuo. The residue was purified by flash chromatography column ($SiO_2$, eluted by 10% EtOAc in hexanes) to provide product 5 (3.77 g, 90%). $[\alpha]^{20}_{D}$: −8.3 (c 0.12, MeOH). $^1$H NMR (400 MHz, $CDCl_3$): δ 5.90 (dddd, J=17.3, 10.4, 5.6, 5.6 Hz, 1H), 5.20 (m, 2H), 5.86-5.76 (m, 1H), 5.70 (br, 1H), 4.17 (d, J=5.6 Hz, 2H), 3.59 (q, J=6.8 Hz, 1H), 1.46 (s, 9H), 1.17 (d, J=7.2 Hz, 3H) ppm. $^{13}$C NMR (100 MHz, $CDCl_3$): δ 173.7, 134.6, 117.5, 81.4, 75.1, 59.7, 28.1, 15.0 ppm. HRMS (ESI) m/z calcd for $C_{10}H_{19}NO_3$ $(M+H)^+$ 202.1443, found 202.1449.

Scheme S4. Synthesis of building block 6.

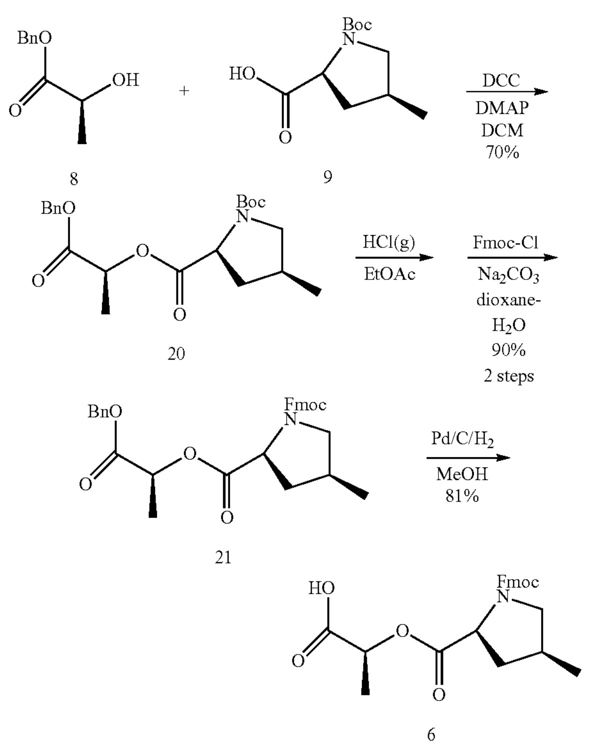

N-Boc-4-MePro-Lac-OBn (20). To the suspension of 4-MePro-OH (9) (3.247 g, 14.160 mmol) in toluene (5.0 ml) was added N,N-diisopropylethylamine (DIEA) (3.69 ml, 21.24 mmol), 2,4,6-trichlorobenzoyl chloride (3.32 ml, 21.24 mmol) at room temperature under argon, and stirred at the same temperature for 40 min. Then the benzyl lactate (8) (2.5 ml, 15.575 mmol) and DMAP (2.941 g, 24.07 mmol) were added to the above mixture at 0° C. The reaction was stirred at 0° C. for 20 min and at room temperature for another 4 h, then it was quenched with water (50 ml) and extracted with diethyl ether (50 ml×4). The combined organic layer was washed with saturated $NH_4Cl$ (50 ml×2), saturated $NaHCO_3$ (50 ml×2), brine (50 ml), dried over $MgSO_4$ and concentrated in vacuo. The residue was purified by silica gel flash chromatography column (eluted by 10% ethyl acetate in hexane) to give ester 20 (4.738 g, 86%). $[\alpha]^{20}_{D}$: −86 (c 0.43, MeOH). $^1$H NMR (400 MHz, $CDCl_3$, mixture of rotamers, major and minor (1/1)): δ 7.39-7.26 (m, 5H), 5.25-5.09 (m, 3H), 4.65 (d, J=10.8 Hz, 1H), 4.31 (t, J=8.4 Hz, 0.5H), 4.22 (t, J=8.4 Hz, 0.5H), 4.22 (t, J=8.4 Hz, 0.5H), 3.73 (dd, J=10.0, 6.8 Hz, 0.5H), 3.65 (dd, J=10.4, 7.2 Hz, 0.5H), 3.65 (dd, J=10.4, 7.2 Hz, 0.5H), 2.95 (dd+dd, J=10.0, 10.0 Hz, 1H), 2.41-2.32 (m, 1H), 2.26-2.13 (m, 1H), 1.58-1.49 (m, 4H), 1.45 (s, 4.5H), 1.39 (s, 4.5H), 1.00 (d, J=6.4 Hz, 1.5H), 0.98 (d, J=6.0 Hz, 1.5H) ppm. $^{13}$C NMR (100 MHz, $CDCl_3$, mixture of rotamers, major and minor (1/1)): δ 172.8, 172.4, 170.7, 170.3, 154.3, 153.5, 135.3, 135.2, 128.6, 128.6, 128.5, 128.5, 128.4, 128.3, 128.3, 80.0, 79.9, 68.8, 68.7, 67.2, 67.0, 59.1, 58.7, 53.9, 53.3, 38.7, 37.7, 33.3, 32.6, 28.5, 28.2, 17.0, 16.9, 16.9, 16.8 ppm. HRMS (ESI) m/z calcd for $C_{21}H_{29}NO_6$ $(M+Na)^+$ 414.1893, found 414.1878.

N-Fmoc-4-MePro-Lac-OBn (21). Trifluoroacetic acid (TFA) (30 ml) was added to the solution of compound 20 (4.738 g, 12.108 mmol) in $CH_2Cl_2$ (30 ml) at 0° C. The reaction mixture was stirred at 0° C. for 20 min, then moved room temperature and stirred for 1.5 h. Toluene (30 ml) was added in and the solvent was evaporated. Another toluene (5 ml×3) was added to the concentrated residue and evaporated again for three times to move excess TFA. The residue was dried under vacuum and used in the next step without purification. The dried residue was dissolved in 1,4-dioxane (30 ml) and water (30 ml). $NaHCO_3$ (2.543 g, 30.271 mmol), Fmoc-Cl (3.759 g, 14.53 mmol) were added the above solution successively at 0° C. After the reaction mixture was stirred at 0° C. for 20 min, at room temperature for 4.5 h, it was diluted water (30 ml) and extracted with EtOAc (50 mL×3). The combined organic layer was washed water (30 mL×3), dried with anhydrous $MgSO_4$, filtered and concentrated in vacuo. The residue was purified by flash chromatography column ($SiO_2$, eluted by 10-25% EtOAc in hexane) to provide product 21 (5.874 g, 95%). $[\alpha]^{20}_{D}$: −81 (c 0.21, MeOH). $^1$H NMR (500 MHz, $CDCl_3$, mixture of rotamers, major and minor (5.5/4.5)): δ 7.77 (dd, J=7.0, 7.0 Hz, 2H), 7.64 (d, J=7.5 Hz, 0.55H), 7.61 (dd, J=6.5, 6.5 Hz, 1H), 7.56 (d, J=7.5 Hz, 0.45H), 7.42-7.30 (m, 9H), 5.27 (q, J=7.0 Hz, 0.55H), 5.23-5.07 (m, 2.45H), 4.51 (dd, J=10.5, 6.0 Hz, 0.45H), 4.45 (dd, J=10.0, 6.5 Hz, 0.55H), 4.41 (t, J=8.5 Hz, 0.55H), 4.35 (t, J=8.0 Hz, 0.45H), 4.33-4.26 (m, 1.55H), 4.16 (dd, J=6.5, 6.5 Hz, 0.45H), 3.85 (dd, J=10.5, 7.0 Hz, 0.45H), 3.80 (dd, J=10.0, 7.0 Hz, 0.55H), 3.13 (dd, J=10.0, 10.0 Hz, 0.55H), 3.05 (dd, J=10.0, 10.0 Hz, 0.45H), 2.46 (dq, J=7.5, 7.5 Hz, 1H), 2.34-2.26 (m, 0.55H), 2.26-2.18 (m, 0.45H), 1.69-1.62 (m, 1H), 1.56 (d, J=7.0 Hz, 1.65H), 1.47 (d, J=7.0 Hz, 1.35H), 1.07 (d, J=6.5 Hz, 1.65H), 1.03 (d, J=6.5 Hz, 1.35H) ppm. $^{13}$C NMR (125 MHz, $CDCl_3$, mixture of rotamers, major and minor (5.5/4.5)): δ 172.2, 172.1, 170.6, 170.3, 154.8, 154.3, 144.5, 144.2, 144.0, 143.7, 141.4, 141.4, 141.3, 135.3, 135.2, 128.7, 128.7, 128.6, 128.5, 128.3, 128.3, 127.8, 127.7, 127.7, 127.1, 127.1, 127.0, 125.3, 125.2, 125.2, 125.0, 120.0, 120.0, 120.0, 69.0, 69.0, 67.6, 67.4, 67.2, 67.1, 59.3, 58.8, 54.2, 53.7, 47.4, 47.3, 38.8, 37.6, 33.5, 32.6, 17.1, 17.0, 16.9, 16.9 ppm. HRMS (ESI) m/z calcd for $C_{31}H_{31}NO_6$ $(M+Na)^+$ 536.2049, found 536.2029.

N-Boc-4-MePro-Lac-OH (6). MeOH (250 ml) was added cautiously to the mixture of compound 21 (6.6 g, 12.86 mmol) and Pd/C (10% wt) (660 mg). The suspending mixture was degassed with argon (balloon) and hydrogen (balloon) successively, then it was stirred under hydrogen gas (balloon) at room temperature for 30 min. The catalyst was removed by filtration through Celite and the filtrate cake was washed with MeOH. The combined filtrate was concentrated in vacuo and purified by flash chromatography column ($SiO_2$, eluted by 10-15% MeOH in $CH_2Cl_2$) to provide product 6 as a white solid (5.0 g, 92%). $[\alpha]^{20}_{D}$: −82.5 (c 0.11 MeOH). $^1$H NMR (400 MHz, $CDCl_3$, mixture of rotamers, major and minor (5.5/4.5)): δ 8.73 (br, 1H), 7.77-7.74 (m, 2H), 7.62-7.58 (m, 1.55H), 7.55 (d, J=7.6 Hz, 0.45H), 7.39 (d, J=7.6, 7.6 Hz, 2H), 7.33-7.28 (m, 2H), 5.20-5.13 (m, 0.55H), 5.00 (q, J=7.2 Hz, 0.45H), 4.52-4.39 (m, 1.55H), 4.36-4.24 (m, 2H), 4.15 (dd, J=6.8, 6.8 Hz, 0.45H), 3.83 (dd, J=10.8, 7.6 Hz, 0.45H), 3.78-3.72 (m, 1H), 3.12-3.01 (m, 1H), 2.54-2.45 (m, 1H), 2.35-2.19 (m, 1H), 1.78-1.68 (m, 1H), 1.51 (d, J=7.2 Hz, 1.65H), 1.44 (d, J=7.2 Hz, 1.35H), 1.08 (d, J=6.4 Hz, 1.65H), 1.04 (d, J=6.4 Hz, 1.35H) ppm. $^{13}$C NMR (100 MHz, $CDCl_3$, mixture of rotamers, major and minor (5.5/4.5)): δ 175.2, 175.0, 172.2, 172.0, 155.1, 154.5, 144.3, 144.1, 143.8, 143.6, 141.3, 141.3, 141.2, 127.8, 127.8, 127.7, 127.1, 127.1, 127.0, 125.2, 125.2, 125.2, 125.0, 120.0, 120.0, 120.0, 119.9, 69.4, 69.1, 67.8, 67.6, 59.4, 58.8, 54.2, 53.7, 53.5, 47.3, 47.2, 38.6, 37.6, 33.3, 33.3, 32.6, 17.3, 17.1, 17.0, 16.9 ppm. HRMS (ESI) m/z calcd for $C_{24}H_{25}NO_6$ $(M+Na)^+$ 446.1580. found 446.1563.

Scheme S4. Alternative synthesis of building block 6.

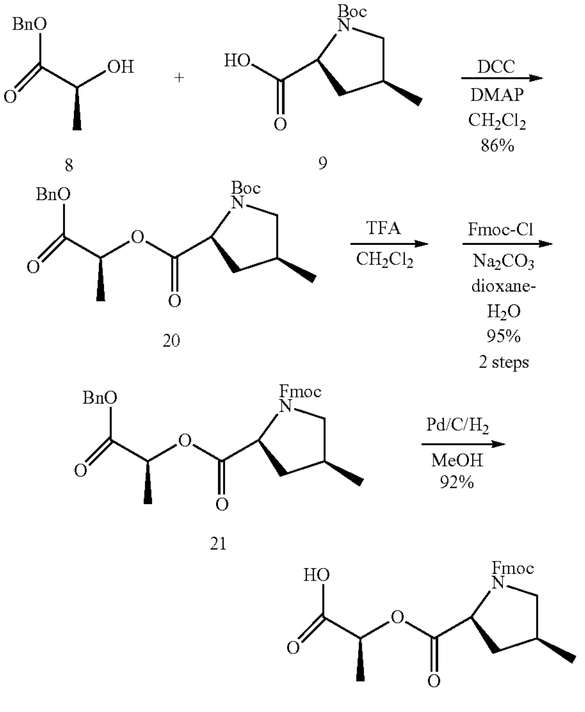

8 9 20 21 6

N-Boc-4-MePro-Lac-OBn (20). To the suspension of 4-MePro-OH (9) (3.247 g, 14.160 mmol) in toluene (5.0 mL) was added N,N-diisopropylethylamine (DIEA) (3.69 mL, 21.24 mmol), 2,4,6-trichlorobenzoyl chloride (3.32 mL, 21.24 mmol) at room temperature under argon, and stirred at the same temperature for 40 min. Then the benzyl lactate (8) (2.5 mL, mmol) and DMAP (2.941 g, 24.07 mmol) were added to the above mixture at 0° C. The reaction was stirred at 0° C. for 20 min and at room temperature for another 4 h, then it was quenched with water (50 mL) and extracted with diethyl ether (50 mL×4). The combined organic layer was washed with saturated $NH_4Cl$ (50 mL×2), saturated $NaHCO_3$ (50 mL×2), brine (50 mL), dried over $MgSO_4$ and concentrated in vacuo. The residue was purified by silica gel flash chromatography column (eluted by 10% ethyl acetate in hexane) to give ester 20 (4.738 g, 86%). $[\alpha]^{20}_D$: −86 (c 0.43, MeOH). $^1$H NMR (400 MHz, $CDCl_3$, mixture of rotamers, major and minor (1/1)): 7.39-7.26 (m, 5H), 5.25-5.09 (m, 3H), 4.65 (d, J=10.8 Hz, 1H), 4.31 (t, J=8.4 Hz, 0.5H), 4.22 (t, J=8.4 Hz, 0.5H), 4.22 (t, J=8.4 Hz, 0.5H), 3.73 (dd, J=10.0, 6.8 Hz, 0.5H), 3.65 (dd, J=10.4, 7.2 Hz, 0.5H), 3.65 (dd, J=10.4, 7.2 Hz, 0.5H), 2.95 (dd+dd, J=10.0, 10.0 Hz, 1H), 2.41-2.32 (m, 1H), 2.26-2.13 (m, 1H), 1.58-1.49 (m, 4H), 1.45 (s, 4.5H), 1.39 (s, 4.5H), 1.00 (d, J=6.4 Hz, 1.5H), 0.98 (d, J=6.0 Hz, 1.5H) ppm. $^{13}$C NMR (100 MHz, $CDCl_3$, mixture of rotamers, major and minor (1/1)): δ 172.8, 172.4, 170.7, 170.3, 154.3, 153.5, 135.3, 135.2, 128.6, 128.6, 128.5, 128.5, 128.4, 128.3, 128.3, 80.0, 79.9, 68.8, 68.7, 67.2, 67.0, 59.1, 58.7, 53.9, 53.3, 38.7, 37.7, 33.3, 32.6, 28.5, 28.2, 17.0, 16.9, 16.9, 16.8 ppm. HRMS (ESI) m/z calcd for $C_{21}H_{29}NO_6$ $(M+Na)^+$ 414.1893, found 414.1878.

N-Fmoc-4-MePro-Lac-OBn (21). Trifluoroacetic acid (TFA) (30 mL) was added to the solution of compound 20 (4.738 g, 12.108 mmol) in $CH_2Cl_2$ (30 mL) at 0° C. The reaction mixture was stirred at 0° C. for 20 min, then moved room temperature and stirred for 1.5 h. Toluene (30 mL) was added in and the solvent was evaporated. Another toluene (5 mL×3) was added to the concentrated residue and evaporated again for three times to move excess TFA. The residue was dried under vacuum and used in the next step without purification. The dried residue was dissolved in 1,4-dioxane (30 mL) and water (30 mL). $NaHCO_3$ (2.543 g, 30.271 mmol), Fmoc-Cl (3.759 g, 14.53 mmol) were added the above solution successively at 0° C. After the reaction mixture was stirred at 0° C. for 20 min, at room temperature for 4.5 h, it was diluted water (30 mL) and extracted with EtOAc (50 mL×3). The combined organic layer was washed water (30 mL×3), dried with anhydrous $MgSO_4$, filtered and concentrated in vacuo. The residue was purified by flash chromatography column ($SiO_2$, eluted by 10-25% EtOAc in hexane) to provide product 21 (5.874 g, 95%). $[\alpha]^{20}_D$: −81 (c 0.21, MeOH). $^1$H NMR (500 MHz, $CDCl_3$, mixture of rotamers, major and minor (5.5/4.5)): δ 7.77 (dd, J=7.0, 7.0 Hz, 2H), 7.64 (d, J=7.5 Hz, 0.55H), 7.61 (dd, J=6.5, 6.5 Hz, 1H), 7.56 (d, J=7.5 Hz, 0.45H), 7.42-7.30 (m, 9H), 5.27 (q, J=7.0 Hz, 0.55H), 5.23-5.07 (m, 2.45H), 4.51 (dd, J=10.5, 6.0 Hz, 0.45H), 4.45 (dd, J=10.0, 6.5 Hz, 0.55H), 4.41 (t, J=8.5 Hz, 0.55H), 4.35 (t, J=8.0 Hz, 0.45H), 4.33-4.26 (m, 1.55H), 4.16 (dd, J=6.5, 6.5 Hz, 0.45H), 3.85 (dd, J=10.5, 7.0 Hz, 0.45H), 3.80 (dd, J=10.0, 7.0 Hz, 0.55H), 3.13 (dd, J=10.0, 10.0 Hz, 0.55H), 3.05 (dd, J=10.0, 10.0 Hz, 0.45H), 2.46 (dq, J=7.5, 7.5 Hz, 1H), 2.34-2.26 (m, 0.55H), 2.26-2.18 (m, 0.45H), 1.69-1.62 (m, 1H), 1.56 (d, J=7.0 Hz, 1.65H), 1.47 (d, J=7.0 Hz, 1.35H), 1.07 (d, J=6.5 Hz, 1.65H), 1.03 (d, J=6.5 Hz, 1.35H) ppm. $^{13}$C NMR (125 MHz, $CDCl_3$, mixture of rotamers, major and minor (5.5/4.5)): δ 172.2, 172.1, 170.6, 170.3, 154.8, 154.3, 144.5, 144.2, 144.0, 143.7, 141.4, 141.4, 141.3, 135.3, 135.2, 128.7, 128.7, 128.6, 128.5, 128.3, 128.3, 127.8, 127.7, 127.7, 127.1, 127.1, 127.0, 125.3, 125.2, 125.2, 125.0, 120.0, 120.0, 120.0, 69.0, 69.0, 67.6, 67.4, 67.2, 67.1, 59.3, 58.8, 54.2, 53.7, 47.4, 47.3, 38.8, 37.6, 33.5, 32.6, 17.1, 17.0, 16.9, 16.9 ppm. HRMS (ESI) m/z calcd for $C_{31}H_{31}NO_6$ $(M+Na)^+$ 536.2049, found 536.2029.

N-Boc-4-MePro-Lac-OH (6). MeOH (250 mL) was added cautiously to the mixture of compound 21 (6.6 g, 12.86 mmol) and Pd/C (10% wt) (660 mg). The suspending mixture was degassed with argon (balloon) and hydrogen (balloon) successively, then it was stirred under hydrogen gas (balloon) at room temperature for 30 min. The catalyst was removed by filtration through Celite and the filtrate cake was washed with MeOH. The combined filtrate was concentrated in vacuo and purified by flash chromatography column ($SiO_2$, eluted by 10-15% MeOH in $CH_2Cl_2$) to provide product 6 as a white solid (5.0 g, 92%). $[\alpha]^{20}_D$: −82.5 (c 0.11 MeOH). $^1$H NMR (400 MHz, $CDCl_3$, mixture of rotamers, major and minor (5.5/4.5)): δ 8.73 (br, 1H), 7.77-7.74 (m, 2H), 7.62-7.58 (m, 1.55H), 7.55 (d, J=7.6 Hz, 0.45H), 7.39 (d, J=7.6, 7.6 Hz, 2H), 7.33-7.28 (m, 2H), 5.20-5.13 (m, 0.55H), 5.00 (q, J=7.2 Hz, 0.45H), 4.52-4.39 (m, 1.55H), 4.36-4.24 (m, 2H), 4.15 (dd, J=6.8, 6.8 Hz, 0.45H), 3.83 (dd, J=10.8, 7.6 Hz, 0.45H), 3.78-3.72 (m, 1H), 3.12-3.01 (m, 1H), 2.54-2.45 (m, 1H), 2.35-2.19 (m, 1H), 1.78-1.68 (m, 1H), 1.51 (d, J=7.2 Hz, 1.65H), 1.44 (d, J=7.2 Hz, 1.35H), 1.08 (d, J=6.4 Hz, 1.65H), 1.04 (d, J=6.4 Hz, 1.35H) ppm. $^{13}$C NMR (100 MHz, $CDCl_3$, mixture of rotamers, major and minor (5.5/4.5)): δ 175.2, 175.0, 172.2, 172.0, 155.1, 154.5, 144.3, 144.1, 143.8, 143.6, 141.3, 141.3, 141.2, 127.8, 127.8, 127.7, 127.1, 127.1, 127.0, 125.2, 125.2, 125.2, 125.0, 120.0, 120.0, 120.0, 119.9, 69.4, 69.1, 67.8, 67.6, 59.4, 58.8, 54.2, 53.7, 53.5, 47.3, 47.2, 38.6, 37.6, 33.3, 33.3, 32.6, 17.3, 17.1, 17.0, 16.9 ppm. HRMS (ESI) m/z calcd for $C_{24}H_{25}NO_6$ $(M+Na)^+$ 446.1580, found 446.1563.

Scheme S5. Synthesis of building block 7.

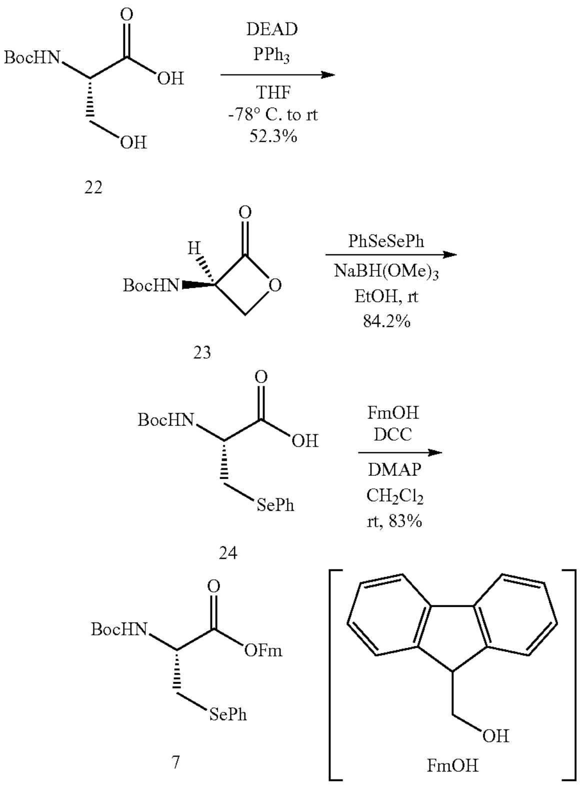

22

23

24

7

N-Boc-L-serine β-lactone (23)[5,6]. Diethyl azodicarboxylate (DEAD) (14.0 mL, 30.73 mmol) was added to the solution of triphenylphosphine ($Ph_3P$) (8.06 g, 30.73 mmol) in THF (250 mL) at −78° C. The resulting solution was stirred at −78° C. for 15 min, then warmed to room temperature and stirred for another 15 min. Then it was cooled to −78° C. A solution of N-Boc-Ser-OH (6.31 g, 30.73 mmol) in THF (30 mL) was added dropwise to the above solution at −78° C. The reaction mixture was stirred at −78° C. for 30 minutes, room temperature for another 2 h, then concentrated in vacuo. The residue was triturated in EtOAc/hexane (200 mL, 1:1) and filtered. The filtrate was concentrated in vacuo and purified by flash column chromatography ($SiO_2$, EtOAc/hexane, 1:3) to provide β-lactone 23 (3.01 g, 52%) as white solid, which was confirmed by MS (ESI) and used in next step directly without characterization by NMR. MS (ESI) m/z calcd for $C_8H_{13}NO_4$ $(M+Na)^+$ 210.08, found 210.1; $C_8H_{13}NO_4$ $(M-H)^-$ 186.08, found 186.0.

(S)—N-Boc-L-(Se)-phenylselenocysteine (24)[5,6]. Sodium trimethoxyborohydride ($NaBH(OMe)_3$) (2.47 g, 19.316 mmol) was added to the solution of diphenyl diselenide ($(PhSe)_2$) (3.014 g, 9.659 mmol) in absolute ethanol (150 mL) at room temperature under argon. The resulting mixture was stirred for 30 min at room temperature, then β-lactone (23) (2.583 g, 13.797 mmol) was added. The reaction mixture was stirred for 3 h at room temperature under argon and concentrated in vacuo. Saturated aqueous $NaHCO_3$ (100 mL) was added to the residue and stirred 20 min at room temperature. The above mixture was washed with $Et_2O$ (30 mL×3). The water layer was acidified with 3 M aqueous HCl to pH 2 and extracted with EtOAc (100 mL×3). The combined organic layers were washed with brine (50 mL×3), dried with anhydrous $MgSO_4$ and concentrated to give a yellowish oil, which was added hexanes (20 mL) and kept −20° C. freezer overnight. The precipitate was filtrated to give product 24 (4.52 g, 95%) as a white solid. $^1$H NMR (400 MHz, $CDCl_3$): δ 7.56-7.54 (m, 2H), 7.27-7.25 (m, 3H), 5.29 (d, J=6.8 Hz, 1H), 4.65-4.61 (m, 1H), 3.39-3.29 (m, 2H), 1.41 (s, 9H) ppm. LRMS (ESI) m/z calcd for $C_{14}H_{19}NO_4{}^{78}Se$ $(M+Na)^+$ 368.05, found 368.0; $C_{14}H_{19}NO_4{}^{78}Se$ $(M-H)^-$ 344.05, found 344.1.

Fm (S)—N-Boc-L-(Se)-phenylselenocysteine ester (7)[7]. DMAP (150 mg, 1.228 mmol), DCC (2.767 g, 13.409 mmol) were added to a solution of 24 (4.205 g, 12.19 mmol) and 9-fluorenylmethanol (FmOH) (2.632 g, 13.415 mmol) in anhydrous $CH_2Cl_2$ (70 mL) at 0° C. under argon. After stirring at room temperature for 4 h, the reaction mixture was evaporated in vacuo. EtOAc (200 mL) was added to the residue and the suspension was filtered. The filtrate was evaporated, and purified by flash chromatography column on silica gel (eluted by 6-12% AcOEt in hexane) to provide 7 (4.791 g, 67%). $^1$H NMR (400 MHz, $CDCl_3$): δ 7.78-7.75 (m, 2H), 7.55-7.51 (m, 4H), 7.44-7.39 (m, 2H), 7.35-7.29 (m, 2H), 7.25-7.19 (m, 3H), 5.38 (d, J=8.4 Hz, 1H), 4.76-4.71 (m, 1H), 4.25 (dd, J=10.4, 7.2 Hz, 1H), 4.14-4.04 (m, 2H), 3.29 (br d, J=5.2 Hz, 2H), 1.45 (s, 9H) ppm. $^{13}$C NMR (100 MHz, $CDCl_3$): δ 170.7, 155.1, 143.5, 143.4, 141.4, 141.3, 133.8, 129.2, 128.9, 128.0, 127.6, 127.3, 127.2, 125.2, 125.1, 120.1, 120.1, 80.2, 67.3, 53.4, 46.6, 30.6, 28.4 ppm. HRMS (ESI) m/z calcd for $C_{28}H_{29}NO_4Se$ $(M+H)^+$ 524.1340, found 524.1319.

Scheme S6. Fusing of all fragments and macrocyclization

4
$(COCl)_2$
benzene
5
AgCN/benzene
80° C.
50% 2 steps

-continued

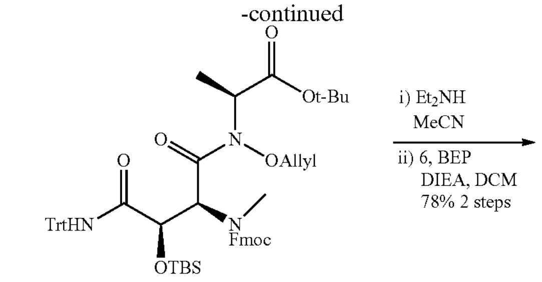

25

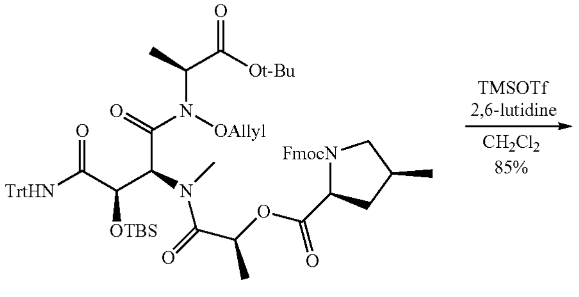

26

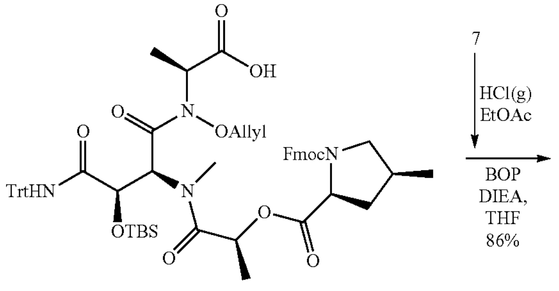

27

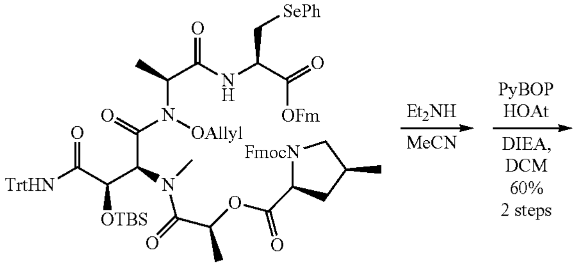

3

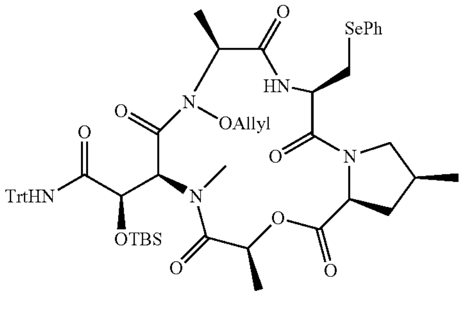

2 (60.3%)

((2S,3R)-3-OTBS-$N_\alpha$-methyl-$N_\alpha$-Fmoc-$N_\gamma$trityl)-Asn-(N—OAllyl)-Ala-Ot-Bu (25). $(COCl)_2$ (2.0 mL, 22.89 mol) was added to the solution of acid 4 (1.107 g, 1.496 mmol) in benzene (22 ml) under nitrogen. After the reaction mixture was stirred at room temperature for 1 h, it was concentrated in vacuo. The residue was added dry benzene (5 mL×3) and evaporated again for another three times to remove traces of $(COCl)_2$, and dried under high vacuum. The residue was dissolved in dry benzene (24 ml) and the solution of compound 5 (352 mg, 1.75 mmol) in dry benzene (2 ml) was added under $N_2$. The reaction flask was equipped with a reflux condenser and covered with Al foil. AgCN (260 mg, 1.942 mmol) was added in a single portion. The reaction mixture was stirred at room temperature for 10 min and then at 80° C. to for 20 min (pre-heated oil bath). The reaction mixture was cooled to room temperature and diluted with $CH_2Cl_2$ (40 ml) and filtered through Celite. The filtrate was then concentrated in vacuo and purified by flash chromatography column ($SiO_2$, eluted by 7-15% EtOAc in hexanes) to afford 25 (690 mg, 50%) as a white solid. $[\alpha]^{20}_D$: +20.3 (c 0.1, MeOH). $^1H$ NMR (400 MHz, $CDCl_3$, mixture of rotamers, major and minor (3/1)): δ 7.88 (br s, 0.25H), 7.78 (d, J=7.6 Hz, 2H), 7.75 (br s, 0.75H), 7.72 (d, J=7.6 Hz, 0.75H), 7.64-7.60 (m, 2H), 7.49 (d, J=6.8 Hz, 0.25H), 7.41 (dd, J=7.6, 7.6 Hz, 2H), 7.36-7.19 (m, 16H), 6.12-5.92 (m, 0.75H), 5.61 (d, J=8.4 Hz, 0.75H), 5.47 (d, J=6.0 Hz, 0.25H), 5.38-5.19 (m, 2H), 4.73-4.41 (m, 5H), 4.30-4.20 (m, 2H), 3.06 (s, 2.25H), 2.96 (s, 0.75H), 1.53-1.45 (m, 12H), 0.84 (s, 2.25H), 0.81 (s, 6.75H), 0.09 (s, 2.25H), 0.03 (s, 0.75H), −0.01 (s, 0.75H), −0.07 (s, 2.25H) ppm. $^{13}C$ NMR (100 MHz, $CDCl_3$, mixture of rotamers, major and minor (3/1)): δ 169.5, 169.4, 168.7, 456.4, 155.7, 144.8, 144.6, 144.5, 144.2, 144.1, 143.4, 141.5, 141.3, 141.3, 141.1, 131.7, 131.0, 129.0, 128.9, 128.1, 128.0, 127.9, 127.8, 127.7, 127.2, 127.1, 127.1, 127.0, 125.5, 125.4, 120.6, 120.2, 120.1, 120.0, 119.1, 82.0, 81.9, 78.0, 77.4, 77.3, 73.4, 71.9, 70.3, 68.2, 60.1, 58.8, 58.2, 58.0, 47.2, 46.9, 34.8, 34.6, 32.0, 31.9, 29.8, 29.8, 28.0, 26.0, 25.9, 22.8, 22.8, 17.9, 17.8, 14.8, 14.5, 14.2, −4.7, −4.8, −4.9 ppm. HRMS (ESI) m/z calcd for $C_{55}H_{65}N_3O_8Si$ $(M+H)^+$ 924.4619, found 924.4594.

(N-Fmoc-4-Me)-Pro-Lac-((2S,3R)-3-OTBS-$N_\alpha$-methyl-$N_\alpha$-Fmoc-$N_\gamma$-trityl)-Asn-(N—OAllyl)-Ala-Ot-Bu (26). Dipeptide 25 (283.0 mg, 0.306 mmol) was treated with diethylamine ($Et_2NH$) (4.0 ml) in MeCN (8.0 ml) at room temperature for 1 h. The reaction mixture was concentrated in vacuo and the residue was co-evaporated with toluene (5 ml×3) for three times to remove trace of $Et_2NH$, and dried with high vacuum for 1 h. DIEA (160 mmol) was added to the solution of the above residue and BEP (125.9 mg, 0.46 mmol) in dry $CH_2Cl_2$ (18 ml) at 0° C. The reaction mixture was stirred at room temperature overnight under argon, then concentrated in vacuo and purified by flash chromatography column ($SiO_2$, eluted by EtOAc/hexane (1:3, v/v) to afford product 26 (359 mg, 78%). $[\alpha]^{20}_D$: −42.0 (c 0.2, MeOH). $^1H$ NMR (400 MHz, $CDCl_3$, mixture of rotamers, major and minor (6/4)): δ 7.82-7.76 (m, 3H), 7.68 (d, J=6.8 Hz, 0.4H), 7.63-7.58 (m, 1.6H), 7.41-7.38 (m, 2.4H), 7.35-7.10 (m, 16.6H), 6.00 (br, 1H), 5.81 (br m, 0.6H), 5.72 (br d, J=5.6 Hz, 0.6H), 5.65 (br m, 0.4H), 4.62 (br m, 1H), 4.58-4.48 (m, 2.4H), 4.44-4.20 (m, 4H), 3.79 (br m, 0.4H), 3.72 (br m, 0.6H), 3.10-2.95 (m, 4H), 2.16 (br m, 2H), 1.77-1.69 (m, 0.4H), 1.66-1.57 (m, 0.6H), 1.50-1.45 (m, 13.8H), 1.34 (d, J=6.4 Hz, 1.2H), 1.00-0.92 (m, 3H), 0.92-0.83 (m, 2.4H), 0.79 (s, 3.6H), 0.78 (s, 5.4H), 0.07 (s, 1.8H), −0.12 (s, 1.8H) ppm. $^{13}C$ NMR (100 MHz, $CDCl_3$, mixture of rotamers, major and minor (6/4)): δ 172.1, 172.0, 169.6, 169.5, 169.3, 169.0, 168.9, 154.8, 154.4, 144.6, 144.5, 144.3, 144.0, 143.7, 141.1, 141.3, 141.3, 131.8, 131.7, 129.0, 128.0, 127.8, 127.7, 127.7, 127.2, 127.1, 127.1, 127.0, 125.5, 125.3, 125.2, 125.1, 121.0, 120.0, 82.0, 78.1, 77.4, 72.1, 72.1, 70.4, 67.8, 67.5, 67.0, 59.8, 59.3, 58.7, 58.6, 57.1, 54.3, 53.8, 47.4, 47.3, 38.7, 37.6, 34.6, 34.8, 33.5, 32.9, 32.6, 29.8, 28.1, 26.0, 17.9, 17.1, 17.0, 15.0, −4.7, −4.9 ppm. HRMS (ESI) m/z calcd for $C_{64}H_{78}N_4O_{11}Si$ $(M+Na)^+$ 1129.5334, found 1129.5320.

(N-Fmoc-4-Me)-Pro-Lac-((2S,3R)-3-OTBS-$N_\alpha$-methyl-$N_\alpha$-Fmoc-$N_\gamma$-trityl)-Asn-(N—OAllyl)-Ala-OH (27). To the solution of 26 (355 mg, 0.321 mmol) in anhydrous $CH_2Cl_2$ (20 mL) were added 2,6-lutidine (1.86 mL, 16.04 mmol) and trimethylsilyl trifluoromethanesulfonate (TMSOTf) (1.74 mL, 9.62 mmol) at 0° C. under argon. After stirred at the same temperature for 20 min, the reaction mixture was moved to room temperature and stirred for 2.5 h, then it was quenched with saturated aqueous $NaHCO_3$ (30 mL) and extracted with EtOAc (50 mL×3). The combined organic layer was washed with 5% $KHSO_4$ (30 mL×5), water (30 mL×2) and brine (30 mL), dried with anhydrous $MgSO_4$ and evaporated in vacuo. The resulting crude mixture was purified by flash chromatography column ($SiO_2$, eluted by 5% MeOH in $CH_2Cl_2$) to provide acid 27 (285 mg, 85%) as a white solid. $[\alpha]^{20}_D$: −55.0 (c 0.09, MeOH). $^1H$ NMR (400 MHz, $CDCl_3$, mixture of rotamers, major and minor (5.5/4.5)): δ 8.15 (s, 0.45H), 8.11 (s, 0.55H), 7.76 (dd, J=6.4, 6.4 Hz, 2H), 7.63-7.55 (m, 2H), 7.41-7.36 (m, 2H), 7.32-7.25 (m, 11H), 7.16-7.14 (m, 6H), 6.03-5.91 (m, 1H), 5.87 (dd, J=7.6 Hz, 1H), 5.57 (br d, J=6.0 Hz, 0.55H), 5.41-5.27 (m, 2.45H), 4.90-4.80 (m, 2H), 4.60-4.50 (m, 2H), 4.48-4.41 (m, 1H), 4.38-4.26 (m, 2.55H), 4.17 (dd, J=6.4 Hz, 0.45H), 3.85-3.75 (m, 1H), 3.09-3.03 (m, 0.55H), 2.98 (br s, 3.45H), 2.50-2.38 (br m, 1H), 2.31-2.17 (br m, 1H), 1.70-1.56 (m, 1H), 1.50-1.45 (m, 4.65H), 1.37 (d, J=6.4 Hz, 1.35H), 1.05 (d, J=6.4 Hz, 1.65H), 1.01 (d, J=6.4 Hz, 1.35H), 0.80 (s, 4.95H), 0.79 (s, 4.05H), 0.09 (s, 1.65H), 0.07 (s, 1.35H), 0.07 (s, 3H) ppm. $^{13}C$ NMR (100 MHz, $CDCl_3$, mixture of rotamers, major and minor (5.5/4.5)): δ 171.9, 171.8, 171.5, 171.3, 170.8, 170.9, 170.8, 169.6, 169.6, 154.8, 154.4, 144.4, 144.3, 143.9, 143.7, 141.4, 141.3, 141.3, 131.0, 130.9, 128.7, 128.2, 127.8, 127.8, 127.7, 127.5, 127.2, 127.1, 127.0, 125.4, 125.3, 125.2, 125.0, 121.7, 120.0, 120.0, 79.4, 77.3, 71.2, 70.3, 70.1, 67.6, 67.5, 59.3, 58.8, 58.1, 57.2, 54.2, 53.8, 47.4, 47.3, 38.7, 37.5, 33.4, 33.0, 32.5, 31.7, 25.9, 22.8, 17.9, 17.2, 16.6, 16.4, 14.2, −4.7, −5.1 ppm. HRMS (ESI) m/z calcd for $C_{60}H_{70}N_4O_{11}Si$ $(M+Na)^+$ 1073.4708, found 1073.4691.

(N-Fmoc-4-Me)-Pro-Lac-((2S,3R)-3-OTBS-$N_\alpha$-methyl-$N_\alpha$-Fmoc-$N_\gamma$-trityl)-Asn-(N—OAllyl)-Ala-((S)—N-Boc-L-(Se)-phenylseleno)-Cys-OFm (3). Compound 7 (244.7 mg, 0.468 mmol) was treated with 4 M HCl in dry EtOAc (15 ml) at 0° C. for 10 min and then room temperature for 1 h. The reaction mixture was concentrated in vacuo, and the residue was co-evaporated with toluene (5 ml×3) for three times to move trace of HCl. The residue was dried under vacuum and used in next step without purification. Compound 27 (277 mg, 0.264 mmol), BOP (256.4 mg, 0.58 mmol), DIEA (230 μl, 1.321 mmol) were added successively to the solution of the above residue from 7 in dry THF (20 ml) at room temperature. After the reaction mixture was stirred at the same temperature for 3 h, it was evaporated in vacuo and purified by flash chromatography column ($SiO_2$, eluted by 15-20% EtOAc in hexane) to provide product 3 (330 mg, 86%). $[\alpha]^{20}_D$: −54.4 (c 0.09, MeOH). $^1H$ NMR (400 MHz, $CDCl_3$, mixture of rotamers, major and minor (5.5/4.5)): δ 8.21 (s, 0.45H), 8.19 (s, 0.55H), 8.09 (d, J=7.6 Hz, 1H), 7.79-7.76 (m, 4H), 7.65-7.57 (m, 2H), 7.53 (d, J=7.6 Hz, 1H), 7.48-7.12 (m, 28H), 6.07-5.90 (m, 2H), 5.59 (q, J=5.6 Hz, 0.55H), 5.50-5.38 (m, 1.45H), 5.30 (dd, J=10.0, 1H), 5.25-5.19 (br m, 1H), 4.98 (d, J=7.6 Hz, 1H), 4.78-4.71 (m, 1H), 4.66-4.60 (m, 1H), 4.50-4.26 (m, 6H), 4.18 (dd, J=6.8, 6.8 Hz, 0.55H), 4.09 (t, J=8.8 Hz, 1H), 4.02 (dd, J=6.8, 6.8 Hz, 1H), 3.89-3.79 (m, 1H), 3.12-3.00 (m, 4.45H), 2.89-2.84 (br m, 1H), 2.58-2.47 (m, 1H), 2.37-2.27 (m, 1H), 2.25-2.14 (m, 1.55H), 1.74-1.62 (m, 1.45H), 1.50 (br d, J=6.8 Hz, 4.65H), 1.40 (d, J=6.8 Hz, 1.35H), 1.09 (d, J=6.4 Hz, 1.65H), 1.05 (d, J=6.4 Hz, 1.35H), 0.82 (s, 4.05H), 0.81 (s, 4.95H), 0.15-0.12 (m, 6H) ppm. $^{13}C$ NMR (100 MHz, $CDCl_3$): δ 172.0, 171.9, 171.8, 171.8, 170.5, 170.1, 169.3, 168.8, 168.7, 154.8, 154.4, 144.4, 144.3, 144.1, 144.0, 143.8, 143.3, 141.4, 141.4, 141.4, 141.4, 141.2, 133.7, 133.7, 131.1, 131.0, 129.3, 129.0, 128.8, 128.2, 127.9, 127.8, 127.8, 127.8, 127.8, 127.7, 127.7, 127.5, 127.5, 127.3, 127.2, 127.1, 127.1, 127.0, 125.7, 125.3, 125.3, 125.3, 125.2, 125.0, 120.7, 120.1, 120.0, 120.0, 79.0, 79.0, 77.4, 71.0, 70.9, 70.4, 70.3, 67.6, 67.6, 67.5, 67.2, 59.3, 58.7, 57.0, 57.0, 55.4, 54.2, 53.8, 52.9, 47.5, 47.3, 46.7, 38.7, 37.6, 33.5, 33.3, 33.3, 32.6, 31.7, 29.8, 28.5, 25.9, 22.8, 17.9, 17.3, 17.2, 16.6, 15.0, 14.2, −4.7, −5.0 ppm. HRMS (ESI) m/z calcd for $C_{83}H_{89}N_5O_{12}SeSi$ $(M+Na)^+$ 1478.5340, found 1478.5337.

Macrocycle 2. Linear compound 3 (222.5 mg, 0.153 mmol) was treated with diethylamine ($Et_2NH$) (10 ml) in MeCN (20 ml) under nitrogen atmosphere at room temperature for 2.5 h. The reaction mixture was concentrated in vacuo and the residue was co-evaporated with the mixture of toluene/$CH_2Cl_2$/DIEA (10:10:1, 5 ml×3) for three times and $CH_2Cl_2$ (5 ml×2) two times to remove traces of $Et_2NH$, and dried with high vacuum for 0.5 h. The reaction mixture was purified by a preparative column (Alltech, 1 gram, silica). The column was eluted sequentially by $CH_2Cl_2$, EtOAc/hexane (1:1) and $CH_2Cl_2$/MeOH (4:1). The fraction eluted by $CH_2Cl_2$/MeOH (4:1) was collected, evaporated, dried and used in next step directly. DIEA (239.2 μl, 1.376 mmol) was added to the solution of the above residue, PyBOP (238.6 mg, 0.459 mmol) and HOAt (64.5 mg, 0.474 mmol) in dry $CH_2Cl_2$ (250 ml) at room temperature. The reaction mixture was stirred at the same temperature for 24 h under argon, then concentrated in vacuo and purified by flash chromatography column ($SiO_2$, eluted by EtOAc/hexane (1:3 to 1:1, v/v) to afford product 2 (95.2 mg, 60.3%) and 28 (5.1 mg, 3.8%). $[\alpha]^{20}_D$: −42.3 (c 0.11, MeOH). $^1H$ NMR of 2 (400 MHz, $CDCl_3$): δ 7.75 (s, 1H), 7.46-7.43 (m, 2H), 7.29-7.20 (m, 12H), 7.15-7.12 (m, 6H), 6.82 (d, J=9.2 Hz, 1H), 6.01 (dddd, J=17.0, 10.7, 6.4, 6.0 Hz, 1H), 5.52-5.46 (m, 2H), 5.40-5.30 (m, 2H), 4.89 (ddt, J=11.2, 6.0, 1.2 Hz, 1H), 4.79 (td, J=9.6, 4.8 Hz, 1H), 4.69 (d, J=9.2 Hz, 1H), 4.66 (q, J=6.8 Hz, 1H), 4.56 (dd, J=8.8, 5.2 Hz, 1H), 4.19 (ddt, J=10.8, 6.4, 1.6 Hz, 1H), 3.57 (dd, J=12.0, 7.2 Hz, 1H), 3.15 (dd, J=12.8, 10.4, 1H), 3.06 (dd, J=12.8, 5.2 Hz, 1H), 2.92 (s, 3H), 2.78 (dd, J=12.0, 6.4 Hz, 1H), 2.47-2.40 (m, 1H), 2.15-2.07 (m, 1H), 1.69-1.63 (m, 1H), 1.60 (d, J=6.8 Hz, 3H), 1.11 (d, J=7.2 Hz, 3H), 0.90 (d, J=7.2 Hz, 3H), 0.82 (s, 9H), 0.21 (s, 3H), −0.05 (s, 3H) ppm. $^{13}C$ NMR (100 MHz, $CDCl_3$): δ 169.9, 169.7, 169.4, 168.5, 167.8, 165.4, 144.3, 131.3, 131.1, 129.6, 129.1, 128.0, 127.2, 127.2, 120.1, 78.7, 77.4, 74.8, 70.5, 69.7, 59.8, 59.2, 56.5, 53.7, 49.9, 39.2, 32.3, 30.9, 29.8, 28.4, 26.0, 18.6, 18.0, 16.6, 16.1, −3.6, −5.0 ppm. HRMS (ESI) m/z calcd for $C_{54}H_{67}N_5O_9SeSi$ $(M+Na)^+$ 1060.3771, found 1060.3753.

Scheme S6. Alternative fusing of all fragments and macrocyclization.

4

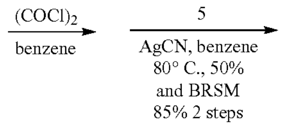

-continued

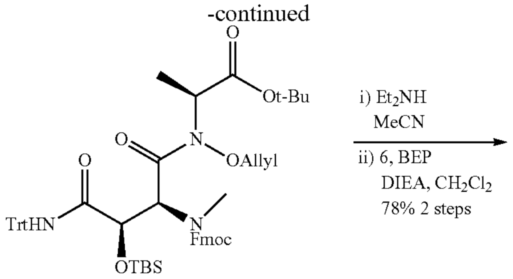

25

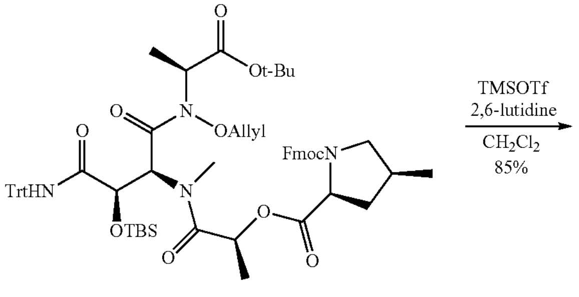

26

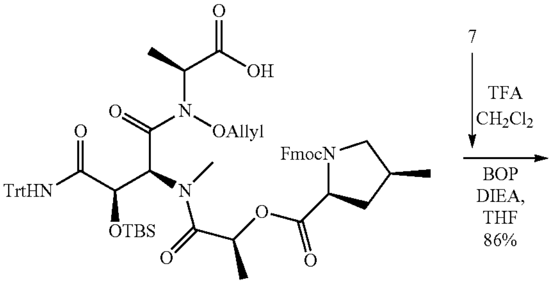

27

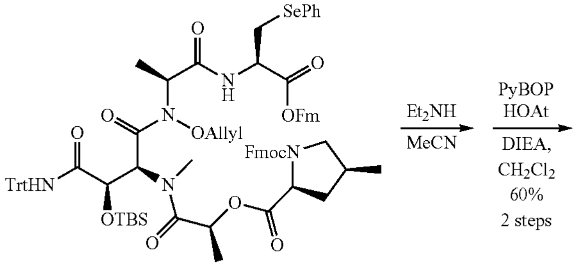

3

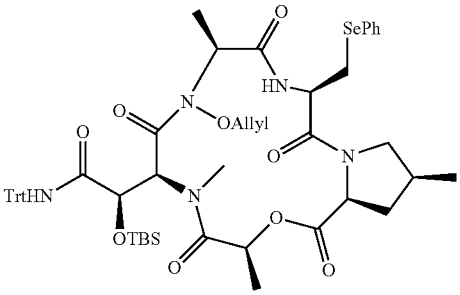

2

((2S,3R)-3-OTBS-$N_\alpha$-methyl-$N_\alpha$-Fmoc-$N_\gamma$-trityl)-Asn-(N—OAllyl)-Ala-Ot-Bu (25). $(COCl)_2$ (2.0 mL, 22.89 mol) was added to the solution of acid 4 (1.107 g, 1.496 mmol) in benzene (22 ml) under nitrogen. After the reaction mixture was stirred at room temperature for 1 h, it was concentrated in vacuo. The residue was added dry benzene (5 mL×3) and evaporated again for another three times to remove traces of $(COCl)_2$, and dried under high vacuum. The residue was dissolved in dry benzene (24 mL) and the solution of compound 5 (352 mg, 1.75 mmol) in dry benzene (2 mL) was added under $N_2$. The reaction flask was equipped with a reflux condenser and covered with Al foil. AgCN (260 mg, 1.942 mmol) was added in a single portion. The reaction mixture was stirred at room temperature for 10 min and then at 80° C. to for 20 min (pre-heated oil bath). The reaction mixture was cooled to room temperature and diluted with $CH_2Cl_2$ (40 mL) and filtered through Celite. The filtrate was then concentrated in vacuo and purified by flash chromatography column ($SiO_2$, eluted by 7-15% EtOAc in hexanes) to afford 25 (690 mg, 50%, 85% BRSM) as a white solid. $[\alpha]^{20}_D$: +20.3 (c 0.1, MeOH). $^1H$ NMR (400 MHz, $CDCl_3$, mixture of rotamers, major and minor (3/1)): δ 7.88 (br s, 0.25H), 7.78 (d, J=7.6 Hz, 2H), 7.75 (br s, 0.75H), 7.72 (d, J=7.6 Hz, 0.75H), 7.64-7.60 (m, 2H), 7.49 (d, J=6.8 Hz, 0.25H), 7.41 (dd, J=7.6, 7.6 Hz, 2H), 7.36-7.19 (m, 16H), 6.12-5.92 (m, 0.75H), 5.61 (d, J=8.4 Hz, 0.75H), 5.47 (d, J=6.0 Hz, 0.25H), 5.38-5.19 (m, 2H), 4.73-4.41 (m, 5H), 4.30-4.20 (m, 2H), 3.06 (s, 2.25H), 2.96 (s, 0.75H), 1.53-1.45 (m, 12H), 0.84 (s, 2.25H), 0.81 (s, 6.75H), 0.09 (s, 2.25H), 0.03 (s, 0.75H), −0.01 (s, 0.75H), −0.07 (s, 2.25H) ppm. $^{13}C$ NMR (100 MHz, $CDCl_3$, mixture of rotamers, major and minor (3/1)): δ 169.5, 169.4, 168.7, 456.4, 155.7, 144.8, 144.6, 144.5, 144.2, 144.1, 143.4, 141.5, 141.3, 141.3, 141.1, 131.7, 131.0, 129.0, 128.9, 128.1, 128.0, 127.9, 127.8, 127.7, 127.2, 127.1, 127.1, 127.0, 125.5, 125.4, 120.6, 120.2, 120.1, 120.0, 119.1, 82.0, 81.9, 78.0, 77.4, 77.3, 73.4, 71.9, 70.8, 70.3, 68.2, 60.1, 58.8, 58.2, 58.0, 47.2, 46.9, 34.8, 34.6, 32.0, 31.9, 29.8, 29.8, 28.0, 26.0, 25.9, 22.8, 22.8, 17.9, 17.8, 14.8, 14.5, 14.2, −4.7, −4.8, −4.9 ppm. HRMS (ESI) m/z calcd for $C_{55}H_{65}N_3O_8Si$ $(M+H)^+$ 924.4619, found 924.4594.

(N-Fmoc-4-Me)-Pro-Lac-((2S,3R)-3-OTBS-$N_\alpha$-methyl-$N_\alpha$-Fmoc-$N_\gamma$-trityl)-Asn-(N—OAllyl)-Ala-Ot-Bu (26). Dipeptide 25 (283.0 mg, 0.306 mmol) was treated with diethylamine ($Et_2NH$) (4.0 mL) in MeCN (8.0 mL) at room temperature for 1 h. The reaction mixture was concentrated in vacuo and the residue was co-evaporated with toluene (5 mL×3) for three times to remove traces of $Et_2NH$, and dried with high vacuum for 1 h. DIEA (160 μL, 0.919 mmol) was added to the solution of the above residue and BEP (125.9 mg, 0.46 mmol) in dry $CH_2Cl_2$ (18 mL) at 0° C. The reaction mixture was stirred at room temperature overnight under argon, then concentrated in vacuo and purified by flash chromatography column ($SiO_2$, eluted by EtOAc/hexane (1:3, v/v) to afford product 26 (359 mg, 78%). $[\alpha]^{20}_D$: −42.0 (c 0.2, MeOH). $^1H$ NMR (400 MHz, $CDCl_3$, mixture of rotamers, major and minor (6/4)): δ 7.82-7.76 (m, 3H), 7.68 (d, J=6.8 Hz, 0.4H), 7.63-7.58 (m, 1.6H), 7.41-7.38 (m, 2.4H), 7.35-7.10 (m, 16.6H), 6.00 (br, 1H), 5.81 (br m, 0.6H), 5.72 (br d, J=5.6 Hz, 0.6H), 5.65 (br m, 0.4H), 4.62 (br m, 1H), 4.58-4.48 (m, 2.4H), 4.44-4.20 (m, 4H), 3.79 (br m, 0.4H), 3.72 (br m, 0.6H), 3.10-2.95 (m, 4H), 2.16 (br m, 2H), 1.77-1.69 (m, 0.4H), 1.66-1.57 (m, 0.6H), 1.50-1.45 (m, 13.8H), 1.34 (d, J=6.4 Hz, 1.2H), 1.00-0.92 (m, 3H), 0.92-0.83 (m, 2.4H), 0.79 (s, 3.6H), 0.78 (s, 5.4H), 0.07 (s, 1.8H), −0.12 (s, 1.8H) ppm. $^{13}C$ NMR (100 MHz, $CDCl_3$, mixture of rotamers, major and minor (6/4)): δ 172.1, 172.0, 169.6, 169.5, 169.3, 169.0, 168.9, 154.8, 154.4, 144.6, 144.5, 144.3, 144.0, 143.7, 141.1, 141.3, 141.3, 131.8, 131.7, 129.0, 128.0, 127.8, 127.7, 127.7, 127.2, 127.1, 127.1, 127.0, 125.5, 125.3, 125.2, 125.1, 121.0, 120.0, 82.0, 78.1, 77.4, 72.1, 72.1, 70.4, 67.8, 67.5, 67.0, 59.8, 59.3, 58.7, 58.6, 57.1, 54.3, 53.8, 47.4, 47.3, 38.7, 37.6, 34.6, 34.8, 33.5, 32.9, 32.6, 29.8, 28.1, 26.0, 17.9, 17.1, 17.0, 15.0, −4.7, −4.9 ppm. HRMS (ESI) m/z calcd for $C_{64}H_{78}N_4O_{11}Si$ $(M+Na)^+$ 1129.5334, found 1129.5320.

(N-Fmoc-4-Me)-Pro-Lac-((2S,3R)-3-OTBS-$N_\alpha$-methyl-$N_\alpha$-Fmoc-$N_\gamma$trityl)-Asn-(N—OAllyl)-Ala-OH (27). To the solution of 26 (355 mg, 0.321 mmol) in anhydrous $CH_2Cl_2$ (20 mL) were added 2,6-lutidine (1.86 mL, 16.04 mmol) and trimethylsilyl trifluoromethanesulfonate (TMSOTf) (1.74 mL, 9.62 mmol) at 0° C. under argon. After stirred at the same temperature for 20 min, the reaction mixture was moved to room temperature and stirred for 2.5 h, then it was quenched with saturated aqueous $NaHCO_3$ (30 mL) and extracted with EtOAc (50 mL×3). The combined organic layer was washed with 5% $KHSO_4$ (30 mL×5), water (30 mL×2) and brine (30 mL), dried with anhydrous $MgSO_4$ and evaporated in vacuo. The resulting crude mixture was purified by flash chromatography column ($SiO_2$, eluted by 5% MeOH in $CH_2Cl_2$) to provide acid 27 (285 mg, 85%) as a white solid. $[\alpha]^{20}_D$: −55.0 (c 0.09, MeOH). $^1H$ NMR (400 MHz, $CDCl_3$, mixture of rotamers, major and minor (5.5/4.5)): δ 8.15 (s, 0.45H), 8.11 (s, 0.55H), 7.76 (dd, J=6.4, 6.4 Hz, 2H), 7.63-7.55 (m, 2H), 7.41-7.36 (m, 2H), 7.32-7.25 (m, 11H), 7.16-7.14 (m, 6H), 6.03-5.91 (m, 1H), 5.87 (dd, J=7.6 Hz, 1H), 5.57 (br d, J=6.0 Hz, 0.55H), 5.41-5.27 (m, 2.45H), 4.90-4.80 (m, 2H), 4.60-4.50 (m, 2H), 4.48-4.41 (m, 1H), 4.38-4.26 (m, 2.55H), 4.17 (dd, J=6.4 Hz, 0.45H), 3.85-3.75 (m, 1H), 3.09-3.03 (m, 0.55H), 2.98 (br s, 3.45H), 2.50-2.38 (br m, 1H), 2.31-2.17 (br m, 1H), 1.70-1.56 (m, 1H), 1.50-1.45 (m, 4.65H), 1.37 (d, J=6.4 Hz, 1.35H), 1.05 (d, J=6.4 Hz, 1.65H), 1.01 (d, J=6.4 Hz, 1.35H), 0.80 (s, 4.95H), 0.79 (s, 4.05H), 0.09 (s, 1.65H), 0.07 (s, 1.35H), 0.07 (s, 3H) ppm. $^{13}C$ NMR (100 MHz, $CDCl_3$, mixture of rotamers, major and minor (5.5/4.5)): δ 171.9, 171.8, 171.5, 171.3, 170.8, 170.9, 170.8, 169.6, 169.6, 154.8, 154.4, 144.4, 144.3, 143.9, 143.7, 141.4, 141.3, 141.3, 131.0, 130.9, 128.7, 128.2, 127.8, 127.8, 127.7, 127.5, 127.2, 127.1, 127.0, 125.4, 125.3, 125.2, 125.0, 121.7, 120.0, 120.0, 79.4, 77.3, 71.2, 70.3, 70.1, 67.6, 67.5, 59.3, 58.8, 58.1, 57.2, 54.2, 53.8, 47.4, 47.3, 38.7, 37.5, 33.4, 33.0, 32.5, 31.7, 25.9, 22.8, 17.9, 17.2, 16.6, 16.4, 14.2, −4.7, −5.1 ppm. HRMS (ESI) m/z calcd for $C_{60}H_{70}N_4O_{11}Si$ $(M+Na)^+$ 1073.4708, found 1073.4691.

(N-Fmoc-4-Me)-Pro-Lac-((2S,3R)-3-OTBS-$N_\alpha$-methyl-$N_\alpha$-Fmoc-$N_\gamma$trityl)-Asn-(N—OAllyl)-Ala-((S)—N-Boc-L-(Se)-phenylseleno)-Cys-OFm (3). Compound 7 (244.7 mg, 0.468 mmol) was treated with TFA (2.5 mL) in $CH_2Cl_2$ (5 mL) at room temperature for 30 min. The reaction mixture was concentrated in vacuo, and the residue was co-evaporated with toluene (5 mL×3) for three times to remove traces of TFA. The residue was dried under vacuum and used in next step without purification. Compound 27 (277 mg, 0.264 mmol), BOP (256.4 mg, 0.58 mmol), DIEA (230 µL, 1.321 mmol) were added successively to the solution of the above residue from 7 in dry THF (20 mL) at room temperature. After the reaction mixture was stirred at the same temperature for 3 h, it was evaporated in vacuo and purified by flash chromatography column ($SiO_2$, eluted by 15-20% EtOAc in hexane) to provide product 3 (330 mg, 86%). $[\alpha]^{20}_D$: −54.4 (c 0.09, MeOH). $^1H$ NMR (400 MHz, $CDCl_3$, mixture of rotamers, major and minor (5.5/4.5)): δ 8.21 (s, 0.45H), 8.19 (s, 0.55H), 8.09 (d, J=7.6 Hz, 1H), 7.79-7.76 (m, 4H), 7.65-7.57 (m, 2H), 7.53 (d, J=7.6 Hz, 1H), 7.48-7.12 (m, 28H), 6.07-5.90 (m, 2H), 5.59 (q, J=5.6 Hz, 0.55H), 5.50-5.38 (m, 1.45H), 5.30 (dd, J=10.0, 1H), 5.25-5.19 (br m, 1H), 4.98 (d, J=7.6 Hz, 1H), 4.78-4.71 (m, 1H), 4.66-4.60 (m, 1H), 4.50-4.26 (m, 6H), 4.18 (dd, J=6.8, 6.8 Hz, 0.55H), 4.09 (t, J=8.8 Hz, 1H), 4.02 (dd, J=6.8, 6.8 Hz, 1H), 3.89-3.79 (m, 1H), 3.12-3.00 (m, 4.45H), 2.89-2.84 (br m, 1H), 2.58-2.47 (m, 1H), 2.37-2.27 (m, 1H), 2.25-2.14 (m, 1.55H), 1.74-1.62 (m, 1.45H), 1.50 (br d, J=6.8 Hz, 4.65H), 1.40 (d, J=6.8 Hz, 1.35H), 1.09 (d, J=6.4 Hz, 1.65H), 1.05 (d, J=6.4 Hz, 1.35H), 0.82 (s, 4.05H), 0.81 (s, 4.95H), 0.15-0.12 (m, 6H) ppm. $^{13}C$ NMR (100 MHz, $CDCl_3$): δ 172.0, 171.9, 171.8, 171.8, 170.5, 170.1, 169.3, 168.8, 168.7, 154.8, 154.4, 144.4, 144.3, 144.1, 144.0, 143.8, 143.3, 141.4, 141.4, 141.4, 141.4, 141.2, 133.7, 133.7, 131.1, 131.0, 129.3, 129.0, 128.8, 128.2, 127.9, 127.8, 127.8, 127.8, 127.8, 127.7, 127.7, 127.5, 127.5, 127.3, 127.2, 127.1, 127.1, 127.0, 125.7, 125.3, 125.3, 125.3, 125.2, 125.0, 120.7, 120.1, 120.0, 120.0, 79.0, 79.0, 77.4, 71.0, 70.9, 70.4, 70.3, 67.6, 67.6, 67.5, 67.2, 59.3, 58.7, 57.0, 57.0, 55.4, 54.2, 53.8, 52.9, 47.5, 47.3, 46.7, 38.7, 37.6, 33.5, 33.3, 33.3, 32.6, 31.7, 29.8, 28.5, 25.9, 22.8, 17.9, 17.3, 17.2, 16.6, 15.0, 14.2, −4.7, −5.0 ppm. HRMS (ESI) m/z calcd for $C_{83}H_{89}N_5O_{12}SeSi$ $(M+Na)^+$ 1478.5340, found 1478.5337.

Macrocycle 2. Linear compound 3 (222.5 mg, 0.153 mmol) was treated with diethylamine ($Et_2NH$) (10 mL) in MeCN (20 mL) under nitrogen atmosphere at room temperature for 2.5 h. The reaction mixture was concentrated in vacuo and the residue was co-evaporated with the mixture of toluene/$CH_2Cl_2$/DIEA (10:10:1, 5 mL×3) for three times and $CH_2Cl_2$ (5 mL×2) two times to remove traces of $Et_2NH$, and dried with high vacuum for 0.5 h. The reaction mixture was purified by a preparative column (Alltech, 1 gram, silica). The column was eluted sequentially by $CH_2Cl_2$, EtOAc/hexane (1:1) and $CH_2Cl_2$/MeOH (4:1). The fraction eluted by $CH_2Cl_2$/MeOH (4:1) was collected, evaporated, dried and used in next step directly. DIEA (239.2 µL, 1.376 mmol) was added to the solution of the above residue, PyBOP (238.6 mg, 0.459 mmol) and HOAt (64.5 mg, 0.474 mmol) in dry $CH_2Cl_2$ (250 mL) at room temperature. The reaction mixture was stirred at the same temperature for 24 h under argon, then concentrated in vacuo and purified by flash chromatography column ($SiO_2$, eluted by EtOAc/hexane (1:3 to 1:1, v/v) to afford product 2 (95.2 mg, 60%). $[\alpha]^{20}_D$: −42.3 (c 0.11, MeOH). $^1H$ NMR of 2 (400 MHz, $CDCl_3$): δ 7.75 (s, 1H), 7.46-7.43 (m, 2H), 7.29-7.20 (m, 12H), 7.15-7.12 (m, 6H), 6.82 (d, J=9.2 Hz, 1H), 6.01 (dddd, J=17.0, 10.7, 6.4, 6.0 Hz, 1H), 5.52-5.46 (m, 2H), 5.40-5.30 (m, 2H), 4.89 (ddt, J=11.2, 6.0, 1.2 Hz, 1H), 4.79 (td, J=9.6, 4.8 Hz, 1H), 4.69 (d, J=9.2 Hz, 1H), 4.66 (q, J=6.8 Hz, 1H), 4.56 (dd, J=8.8, 5.2 Hz, 1H), 4.19 (ddt, J=10.8, 6.4, 1.6 Hz, 1H), 3.57 (dd, J=12.0, 7.2 Hz, 1H), 3.15 (dd, J=12.8, 10.4, 1H), 3.06 (dd, J=12.8, 5.2 Hz, 1H), 2.92 (s, 3H), 2.78 (dd, J=12.0, 6.4 Hz, 1H), 2.47-2.40 (m, 1H), 2.15-2.07 (m, 1H), 1.69-1.63 (m, 1H), 1.60 (d, J=6.8 Hz, 3H), 1.11 (d, J=7.2 Hz, 3H), 0.90 (d, J=7.2 Hz, 3H), 0.82 (s, 9H), 0.21 (s, 3H), −0.05 (s, 3H) ppm. $^{13}C$ NMR (100 MHz, $CDCl_3$): δ 169.9, 169.7, 169.4, 168.5, 167.8, 165.4, 144.3, 131.3, 131.1, 129.6, 129.1, 128.0, 127.2, 127.2, 120.1, 78.7, 77.4, 74.8, 70.5, 69.7, 59.8, 59.2, 56.5, 53.7, 49.9, 39.2, 32.3, 30.9, 29.8, 28.4, 26.0, 18.6, 18.0, 16.6, 16.1, −3.6, −5.0 ppm. HRMS (ESI) m/z calcd for $C_{54}H_{67}N_5O_9SeSi$ $(M+Na)^+$ 1060.3771, found 1060.3753.

Scheme S7. Fully unmasking and completion of final target gatorbulin-1 (1a).

2

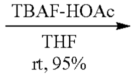

-continued

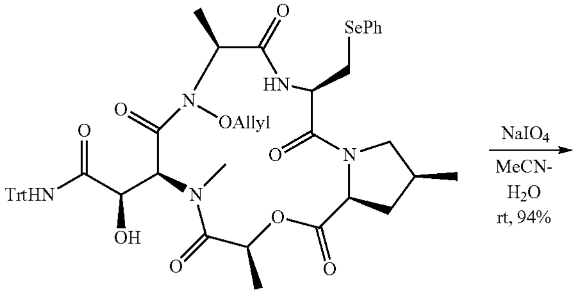

28

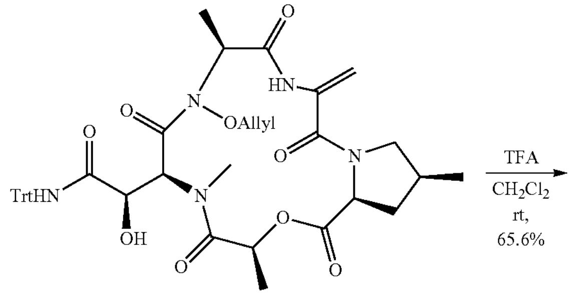

29

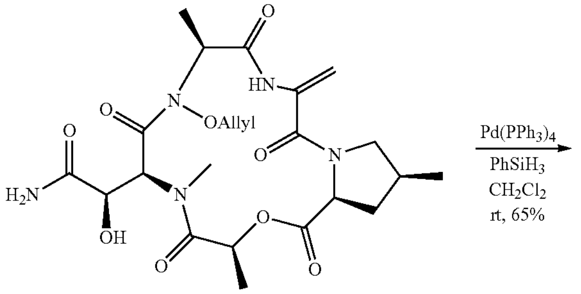

30

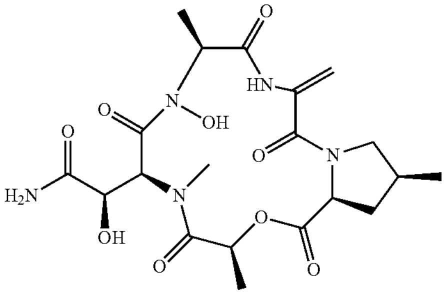

1a

Macrocycle 28. The pre-mixed buffer of TBAF (1.35 mL, 0.5 M in THF, 0.675 mmol) and AcOH (1.62 mL, 0.5 M in THF, 0.81 mmol) was added to the solution of macrocycle 2 (70 mg, 0.0675 mmol) in dry THF (14 mL). After the reaction mixture was stirred at room temperature under argon for 5 h, it was diluted with EtOAc and quenched with saturate $NaHCO_3$ (10 mL) extracted with EtOAc (15 mL×3). The combined organic layers were dried over anhydrous $MgSO_4$ and purified by preparative TLC plate ($SiO_2$, developed by acetone/hexanes 1:2, Rf=0.4) to provide product 28 (59.2 mg, 95%). $[\alpha]^{20}_D$: −91.5 (c 0.09, MeOH). $^1$H NMR (400 MHz, $CDCl_3$): δ 8.10 (s, 1H), 7.47-7.44 (m, 2H), 7.30-7.18 (m, 18H), 6.76 (d, J=9.2 Hz, 2H), 6.09-5.99 (m, 1H), 5.49 (q, J=6.8 Hz, 1H), 5.43-5.33 (m, 2H), 4.91 (dd, J=10.8, 5.6 Hz, 1H), 4.85-4.79 (m, 1H), 4.53 (dd, J=8.8, 6.0 Hz, 1H), 4.46 (br s, 2H), 4.30 (dd+dd, J=11.2, 6.8 Hz, 2H), 3.64 (dd, J=11.6, 7.2 Hz, 1H), 3.18 (dd, J=12.4, 10.0 Hz, 1H), 3.02 (dd, J=12.4, 5.6 Hz, 1H), 3.03 (s, 3H), 2.88-2.83 (m, 1H), 2.51-2.44 (m, 1H), 2.17-2.09 (m, 1H), 1.65 (ddd, J=13.2, 6.4, 6.4 Hz, 1H), 1.57 (d, J=6.8 Hz, 3H), 1.26 (d, J=6.8 Hz, 3H), 0.96 (d, J=6.8 Hz, 3H) ppm. $^{13}$C NMR (100 MHz, $CDCl_3$): δ 169.6, 169.5, 169.5, 169.3, 169.0, 166.8, 144.5, 131.6, 131.2, 129.5, 129.2, 128.8, 128.0, 127.3, 127.1, 120.8, 79.2, 77.4, 71.7, 70.1, 60.0, 59.5, 53.7, 49.7, 39.3, 31.1, 28.9, 18.3, 16.7, 16.5 ppm. HRMS (ESI) m/z calcd for $C_{48}H_{53}N_5O_9Se$ $(M+Na)^+$ 946.2906, found 946.2878.

Macrocycle 29. $NaIO_4$(67.8 mg, 0.314 mmol) was added to the solution of compound 28 (73.2 mg, 0.0793 mmol) in the mixture of MeCN—$H_2O$ (15 mL-11.2 mL) at the room temperature. After the reaction mixture was stirred at the same temperature under argon for 2 h, $CH_2Cl_2$ (25 mL) and aqueous saturate $NaHCO_3$ (15 mL) were added and the resulting mixture was extracted with $CH_2Cl_2$ (20 mL×4). The combined organic layers were dried with anhydrous $MgSO_4$, evaporated in vacuo and purified by preparative TLC plate ($SiO_2$, developed by acetone/hexanes 2:3, Rf=0.5) to afford product 29 (57.2 mg, 94%). $[\alpha]^{20}_D$: −48.4 (c 0.07, MeOH). $^1$H NMR (400 MHz, $CDCl_3$, mixture of three conformers, major, medium and minor (0.65:0.25: 0.1)): δ 8.38 (s, 0.1H), 8.30 (s, 0.1H), 8.28 (s, 0.65H), 8.24 (s, 0.25H), 8.19 (s, 0.65H), 7.99 (s, 0.25H), 7.28-7.20 (m, 15H), 6.48 (s, 0.65H), 6.25 (s, 0.25H), 6.23 (s, 0.1H), 6.14-6.04 (m, 0.25H), 5.95-5.86 (m, 0.65H), 5.86-5.77 (m, 0.1H), 5.63 (q, J=6.8 Hz, 0.75H), 5.48-5.27 (m, 3H), 5.13 (s, 0.65H), 5.05 (br m, 0.25H), 5.01 (s, 0.25H), 4.91 (s, 0.1H), 4.72 (dd, J=8.4, 6.0 Hz, 0.35H), 4.69 (d, J=9.2 Hz, 1H), 4.56 (dd, J=9.6, 7.2 Hz, 0.65H), 4.48 (dd, J=10.8, 6.8 Hz, 0.65H), 4.42-4.39 (m, 2.65H), 4.34-4.31 (m, 1H), 4.30-4.24 (m, 0.35H), 4.18 (q, J=6.8 Hz, 1H), 4.07 (dd, J=10.4, 6.8 Hz, 0.9H), 4.02 (dd, J=11.6, 7.2 Hz, 0.1H), 3.75 (dd, J=11.6, 7.2 Hz, 0.35H), 3.40 (dd, J=10.0, 8.4 Hz, 0.65H), 3.24 (t, J=11.2, 0.25H), 3.14 (t, J=11.2 Hz, 0.1H), 3.05 (s, 1.95H), 3.03 (s, 0.3H), 2.97 (s, 0.75H), 2.63-2.42 (m, 2.25H), 2.37-2.27 (m, 0.65H), 2.00 (d, J=7.2 Hz, 0.3H), 1.81 (d, J=7.6 Hz, 1.95H), 1.62-1.55 (m, 1.75H), 1.48 (d, J=7.2 Hz, 0.3H), 1.40 (d, J=6.8 Hz, 1.95H), 1.33 (d, J=6.4 Hz, 0.75H), 1.15-1.11 (m, 3H) ppm. $^{13}$C NMR (100 MHz, $CDCl_3$, mixture of three conformers, major, medium and minor): δ 172.3, 171.4, 171.0, 170.4, 170.2, 170.0, 169.6, 169.4, 169.0, 168.7, 167.9, 166.5, 166.0, 165.8, 144.5, 144.5, 144.5, 144.4, 135.8, 134.3, 134.3, 131.5, 131.3, 130.6, 130.5, 129.5, 128.7, 128.7, 128.4, 128.2, 128.0, 127.8, 127.1, 121.7, 120.6, 120.3, 104.8, 104.2, 103.1, 78.8, 77.4, 76.3, 74.7, 73.5, 73.4, 70.1, 70.0, 67.9, 67.6, 63.9, 63.6, 63.4, 62.0, 61.7, 60.7, 56.1, 54.7, 53.4, 40.0, 37.4, 36.9, 36.0, 35.9, 34.0, 31.7, 29.8, 17.7, 17.6, 17.3, 17.0, 16.9, 16.7, 16.0, 14.6, 14.2 ppm. HRMS (ESI) m/z calcd for $C_{42}H_{47}N_5O_9$ $(M+Na)^+$ 788.3271, found 788.3244.

Macrocycle 30. TFA (2.0 mL) was added to the solution of 29 (26.3 mg, 0.0344 mmol) in dry $CH_2Cl_2$ (10 mL) at 0° C. The reaction was stirred room temperature for 1 h, then it was diluted with toluene (10 mL). The solvent was evaporated in vacuo and the residue was purified by preparative TLC plate ($SiO_2$, developed by MeOH/$CH_2Cl_2$ 5:95, Rf=0.2) to afford product 30 (11.8 mg, 66%). $[\alpha]^{20}_D$: −54.5 (c 0.08, MeOH). $^1$H NMR (400 MHz, $CDCl_3$, mixture of conformers, major/minor (2:1)): δ 8.24 (s, 0.67H), 7.95 (s, 0.33H), 6.49 (s, 0.67H), 6.27 (s, 0.33H), 6.06-5.96 (m, 1H), 5.80 (br m, 1H), 5.67 (q, J=6.8 Hz, 0.67H), 5.29 (d, J=10.0

Hz, 0.33H), 5.14 (s, 0.67H), 5.02 (br s, 1H), 4.96-4.92 (m, 0.33H), 4.60-4.36 (m, 5H), 4.20-4.07 (m, 2H), 3.74 (dd, J=12.0, 7.2 Hz, 0.33H), 3.35 (dd, J=10.4, 7.6 Hz, 0.67H), 3.23 (t, J=11.6, 0.33H), 3.14-3.12 (m, 1.32H), 3.09-3.06 (m, 2.68H), 2.55-2.43 (m, 2H), 2.38-2.27 (m, 0.67H), 1.67-1.64 (m, 3.33H), 1.47-1.43 (m, 3H), 1.14-1.11 (m, 3H), 7-5.03 (m, 2H), 4.65 (d, J=10.8 Hz, 1H), 4.45 (d, J=10.8 Hz, 1H), 3.86-3.80 (m, 1H), 3.80 (s, 3H), 3.08 (dd, J=7.2, 3.6 Hz, 1H), 2.31-2.20 (m, 2H), 1.87 (br m, 1H), 1.66 (ddd, J=13.2, 9.2, 2.8 Hz, 1H), 1.46-1.34 (m, 2H), 1.06 (d, J=6.8 Hz, 3H), 0.91 (s, 9H), 0.86 (s, 9H) ppm. $^{13}C$ NMR (100 MHz, $CDCl_3$, mixture of conformers, major/minor (2:1)): δ 173.8, 173.6, 170.7, 170.5, 170.0, 169.4, 168.6, 168.4, 166.9, 166.3, 165.3, 134.3, 134.2, 131.2, 130.6, 122.4, 120.3, 104.8, 104.1, 78.2, 77.4, 70.7, 70.4, 63.4, 62.0, 61.8, 60.9, 56.2, 54.7, 40.0, 36.1, 35.3, 33.9, 32.0, 31.8, 29.8, 29.8, 17.9, 17.3, 17.1, 16.7, 15.8, 14.3 ppm. HRMS (ESI) m/z calcd for $C_{23}H_{33}N_5O_9$ $(M+H)^+$ 524.2357, found 524.2341.

Gatorbulin-1 (1a). $PhSiH_3$ (10 μL, 0.081 mmol) and $Pd(PPh_3)_4$ (2.43 mg, 0.0021 mmol, in degassed $CH_2Cl_2$ (0.5 mL) were added to the solution of 30 (11.0 mg, 0.021 mmol) in degassed dry $CH_2Cl_2$ (4.0 mL) sequentially at room temperature. The reaction flask was protected by aluminum foil and the reaction mixture was stirred at the room temperature for 1.5 h under argon. Then the reaction was concentrated under reduced pressure and the residue was purified by preparative reverse TLC plate (C18, developed by $MeOH/H_2O$ (1:1), Rf=0.5). The product band was scraped and washed down by $MeOH/CH_2Cl_2$ (3:7). The washed down product fraction was concentrated to dryness under reduced pressure and rinsed with hexanes. The residue was purified again by reverse preparative cartridge (C18, 100 mg, Alltech, eluted by MeOH). The product fractions were collected, concentrated and dried to provide product 1a (6.6 mg, 65%) as off-white solid. The $^1H$ NMR and $^{13}C$ NMR were identical to natural product 1a (mixture of two conformers (1:1)). $[\alpha]^{20}_D$: −119.2 (c 0.17, MeOH) (natural 1, $[\alpha]^{20}_D$: −84.0 (c 0.10, MeOH)).

(Integrated two conformers separately) Conformer 1: $^1H$ NMR (600 MHz, DMF-$d_7$), δ 11.38 (br s, 1H), 8.28 (s, 1H), 7.28 (s, 1H), 7.09 (s, 1H), 6.46 (s, 1H), 6.07 (br, 1H), 5.51 (br d, J=9.6 Hz, 1H), 5.47 (q, J=7.2 Hz, 1H), 5.23 (s, 1H), 4.51 (br d, 1H), 4.41 (t, J=7.8 Hz, 1H), 4.31 (m, 1H), 3.25 (dd, J=10.2, 7.8 Hz, 1H), 3.09 (s, 3H), 2.58 (m, 1H), 2.53 (m, 1H), 1.58 (m, 1H), 1.53 (d, J=6.6 Hz, 3H), 1.42 (d, J=7.2 Hz, 3H), 1.12 (d, J=6.6 Hz, 3H) ppm; $^{13}C$ NMR (150 MHz, DMF-$d_7$), δ 175.1, 170.8, 170.5, 169.9, 165.9, 136.2, 101.9, 72.9, 68.8, 64.6, 62.6, 57.9, 56.9, 37.0, 34.7, 34.0, 18.0, 17.6, 15.6, 13.8 ppm. Conformer 2: $^1H$ NMR (400 MHz, $d_7$-DMF): δ 10.61 (br s, 1H), 7.91 (s, 1H), 7.41 (s, 1H), 7.21 (s, 1H), 6.22 (s, 1H), 5.90 (br, 1H), 5.38 (q, J=7.2 Hz, 1H), 5.22 (s, 1H), 5.07 (br, 1H), 4.93 (dd, J=9.6, 7.2 Hz, 1H), 4.71 (br q, J=7.2 Hz, 1H), 4.64 (br m, 1H), 4.29 (q, J=6.6 Hz, 1H), 3.71 (dd, J=11.4, 7.2 Hz, 1H), 3.13 (s, 3H), 3.11 (dd, J=11.4, 11.4 Hz, 1H), 2.38 (m, 1H), 1.66 (m, 1H), 1.52 (d, J=6.0 Hz, 3H), 1.40 (d, J=6.6 Hz, 3H), 1.10 (d, J=6.6 Hz, 3H) ppm; $^{13}C$ NMR (100 MHz, $CDCl_3$): δ 174.9, 170.4, 170.2, 169.7, 165.4, 166.8, 136.2, 72.2, 69.7, 63.8, 60.0, 55.8, 55.6 40.8, 34.5, 32.4, 17.3, 16.9 ppm. HRMS (ESI) m/z calcd for $C_{24129}N_5O_9$ $(M+H)^+$ 484.2044, found 484.2028.

(Integrated two conformers together): $^1H$ NMR (600 MHz, DMF-$d_7$, mixture of conformers (1:1)): δ 11.38 (br s, 0.5H), 10.61 (br s, 0.5H), 8.28 (s, 0.5H), 7.91 (s, 0.5H), 7.41 (s, 0.5H), 7.28 (s, 0.5H), 7.21 (s, 0.5H), 7.09 (s, 0.5H), 6.46 (s, 0.5H), 6.22 (s, 0.5H), 6.07 (br, 0.5H), 5.90 (br, 0.5H), 5.51 (br d, J=9.6 Hz, 0.5H), 5.47 (q, J=7.2 Hz, 0.5H), 5.38 (q, J=7.2 Hz, 0.5H), 5.23 (s, 0.5H), 5.22 (s, 0.5H), 5.07 (br, 0.5H), 4.93 (dd, J=9.6, 7.2 Hz, 0.5H), 4.71 (br q, J=7.2 Hz, 0.5H), 4.64 (br m, 0.5H), 4.51 (br d, 0.5H), 4.41 (t, J=7.8 Hz, 0.5H), 4.33-4.28 (m, 1H), 3.71 (dd, J=11.4, 7.2 Hz, 0.5H), 3.25 (dd, J=10.2, 7.8 Hz, 0.5H), 3.15-3.11 (m, 2H), 3.09 (s, 1.5H), 2.60-2.50 (m, 1.5H), 2.41-2.34 (m, 0.5H), 1.69-1.63 (m, 1H), 1.60-1.56 (m, 1H), 1.53 (d, J=6.6 Hz, 1.5H), 1.52 (d, J=6.0 Hz, 1.5H), 1.42 (d, J=7.2 Hz, 1.5H), 1.40 (d, J=6.6 Hz, 1.5H), 1.12 (d, J=6.6 Hz, 1.5H), 1.10 (d, J=6.6 Hz, 1.5H) ppm; $^{13}C$ NMR (150 MHz, DMF-$d_7$, mixture of conformers (1:1)): δ 175.1, 174.9, 170.8, 170.5, 170.4, 170.2, 169.9, 169.7, 169.4, 166.8, 165.9, 165.4, 136.2, 136.2, 101.9, 72.9, 72.2, 69.7, 68.8, 64.6, 63.8, 62.6, 60.0, 57.9, 56.9, 55.8, 55.6, 40.8, 37.0, 34.7, 34.5, 34.0, 32.4, 18.0, 17.6, 17.3, 16.9, 15.6, 13.8 ppm. HRMS (ESI) m/z calcd for $C_{24}H_{29}N_5O_9$ $(M+H)^+$ 484.2044, found 484.2028.

Qualitative Test for Fe(III) Chelating Ability of GB1 (1a)

We applied a solution of GB1 (1a) in $CH_2Cl_2$ to reverse TLC ($C_{18}$) ($MeOH/H_2O$ 1:1, v/v), then dipped the TLC into $FeCl_3$ solution in ethanol (5% wt). The compound quickly caused an orange spot (positive reaction).

REFERENCES FOR SYNTHESIS AND CHARACTERIZATION

1. Sendai, M., Hashiguchi, S., Tomimoto, M., Kishimoto, S., Matsuo, T., Ochiai, M. Synthesis of carumonam (AMA-1080) and a related compound starting from (2R, 3R)-epoxysuccinic acid. *Chem. Pharm. Bull.* 33, 3798-3810 (1985).
2. Koyama, J., Sugita, T., Suzuta, Y., Irie, H. Thermolysis of oxime O-allyl ethers: a new method for pyridine synthesis. *Chem. Pharm. Bull.* 31, 2601-2606 (1985).
3. Shustov, G. V., Chandler, M. K., Wolfe, S. Stereoselective synthesis of multiply substituted [1,2] oxazinan-3-ones via ring-closing metathesis *Can. J. Chem.* 83, 93-103 (2005).
4. Ley, S. V., Priour, A. Total synthesis of the cyclic peptide argyrin B, *Eur. J. Org. Chem.* 3995-4004 (2002).
5. Okeley, N. M., Zhu, Y., van der Donk, W. A. Facile chemoselective synthesis of dehydroalanine-containing peptides, Org. Lett. 2, 3603-3606 (2000).
6. Mori, T., Higashibayashi, S., Goto, T., Kohno, M., Satouchi, Y., Shinko, K., Suzuki, K., Suzuki, S., Tohmiya, H., Hashimoto, K., Nakata, M. Total synthesis of siomycin A: completion of the total synthesis. *Chem. Asian J.* 3, 984-1012 (2008).

B. Biological Methods

Cell Lines

Isogenic HCT116 cell lines were generated and authenticated as described (S. Y. Chun, et al., Oncogenic KRAS modulates mitochondrial metabolism in human colon cancer cells by inducing HIF-1α and HIF-2α target genes. *Mol. Cancer* 9, 293 (2010)), and normal colon CCD841-CoN cells obtained from ATTC. HeLa cell lines were purchased from the American Type Culture Collection (ATCC) and authenticated by Genetica.

MTT Cell Viability Assay

Parental HCT116, $HCT116^{HIF\text{-}1\alpha-/-HIF\text{-}2\alpha-/-}$, $HCT116^{HIF\text{-}1\alpha-/-}$, $HCT116^{HIF\text{-}2\alpha-/-}$, $HCT116^{WT\ KRAS}$ along with normal colon cell line CCD841-CoN were cultured in Dulbecco's modified Eagle medium (DMEM, Life Technologies, USA) supplemented with 10% Fetal Bovine Serum (FBS, Sigma, USA) and maintained in 5% $CO_2$ at 37° C. HCT116 cells (8,000 cells/well) and normal cells (3,000 cells/well) were seeded in 96-well plates, allowed to attach overnight and then treated with different concentrations of GB1 (1a) or solvent control (0.5% DMSO). Cell viability was measured 48 h following treatment with MTT dye using manufacturer's protocol (Promega). $IC_{50}$ was determined by non-linear regression analysis using GraphPad Prism 8. Data are represented as average±SD (n=3).

HCT116 Cell Cycle Analysis

HCT116 cells were seeded in 6-well plates (400,000 cells/well, DMEM/10% FBS and allowed to attach overnight prior to treatment with GB1. Media was replaced by fresh DMEM/10% FBS after 24 h of incubation and treated with compound and solvent control (0.25% DMSO) for 24 h. The medium in each well was collected separately, and the cells washed with 500 μL PBS and collected into the corresponding tubes. Cells were detached using trypsin (Invitrogen) and collected into the corresponding tubes and centrifuged at 400 g for 10 min at 4° C. The supernatant was discarded and the cell pellets were resuspended in 500 μL ice-cold PBS, centrifuged at 400 g for 10 min at 4° C. and supernatant was discarded. The cell pellets were resuspended in 300 μL ice-cold PBS and 700 μL ice-cold EtOH was added slowly to each cell suspension with gentle pipetting. Cells were incubated at −20° C. overnight and centrifuged at 400 g for 10 min at 4° C. next day. The EtOH/PBS was discarded and cells resuspended in 300 μL PBS containing 1 mM EDTA and 100 μg/mL RNase A (Invitrogen). The cells were incubated at 37° C. for 30 min, with shaking at 800 rpm, followed by addition of 1 μL propidium iodide (1 mg/mL, Invitrogen). Fluorescence from propidium iodide-DNA complexes were quantified using FACScan (BD Biosciences LSRFortessa) and data were analyzed using ModFit LT (Verity Software House).

RNA Isolation, Reverse Transcription and Quantitative Polymerase Chain Reaction

HCT116 cells were seeded in 6-well plates at a density of $4\times10^5$ per well and incubated overnight for cells to attach. Cells were treated with 3.2 μM GB1 or 0.25% DMSO (vehicle). RNA was isolated 16 h later using the RNeasy mini kit (QIAGEN, Valencia, CA). Total RNA was quantified using NanoDrop 2000. cDNA synthesis was carried out using SuperScript II Reverse Transcriptase (Invitrogen, Carlsbad, CA) and oligo (dT) (Invitrogen) from 2 μg of total RNA. The qPCR after reverse transcription (RT-qPCR) was performed on a 25 μL reaction solution containing a 0.3 μL aliquot of cDNA, 12.5 μL of TaqMan gene expression master mix, 1.25 μL of probes, and 11 μL RNase-free water. qPCR was carried out on an ABI 7300 sequence detection system using the thermocycler program: 2 min at 50° C., 10 min at 95° C., and 15 s at 95° C. (40 cycles) and 1 min at 60° C. Experiments were performed in triplicate. Probes for target gene: VEGFA (Hs00900055_m1) and for endogenous control: β-actin (Hs99999903_m1). Statistical analysis for comparison between treatment and vehicle group was done using a student t test (*$p<0.05$).

Tubulin Polymerization Assay

Tubulin polymerization was performed using fluorescence based in vitro polymerization kit (Cytoskeleton, #BK011P) per the manufacturer recommendation. Briefly, the provided tubulin was reconstituted to 10 mg/mL stock, as recommended, and used at final concentration of 2 mg/mL in 80 mM PIPES pH 6.9, 2.0 mM $MgCl_2$, 0.5 mM EGTA, 1.0 mM GTP and 15% glycerol for the assays. The compound was prepared in 3-fold dilutions and kept on ice until the assay was started. Buffer components and tubulin stocks were kept on ice until use. The assay plate was pre-warmed at 37° C. for 10 minutes and the compounds were added to the plate wells at 5 uL (<10% DMSO) for 1 minute to warm. Fifty microliters of tubulin reaction mix (2 mg/mL in 80 mM PIPES pH 6.9, 2.0 mM $MgCl_2$, 0.5 mM EGTA, 1.0 mM GTP and 15% glycerol) was added to each well and mixed gently with the inhibitor to avoid bubble formation. The plate was read on FlexStation3 reader (Molecular Devices) at 360 nm excitation/450 nm emission, every minute for 1 hours at 37° C. Decrease in fluorescent signal indicated inhibition of polymerization.

C. Description of the Examples

There is continued demand for new microtubule-targeting agents, ideally against novel binding sites, since anticancer efficacy and the pharmacological effects vary depending on the chemical scaffold and binding site. Current approved drugs and other known tubulin agents bind to six distinct sites at the α/β-tubulin heterodimer. We have discovered a new microtubule-destabilizing cyclodepsipeptide with unique chemotype from a marine cyanobacterium, termed gatorbulin-1. The chemical structure was elucidated through multidimensional characterization. The structure was determined by $^1H$, $^{13}C$ and 15 N NMR and mass spectrometry, revealing the modified pentapeptide possessing a functionally-critical hydroxamate group, and developed a total synthesis to solve the supply issue. We probed the pharmacology using isogenic cancer cell screening, extensive cellular profiling, and complementary phenotypic assays. The unique chemical structure and observed pharmacology suggested that GB1 might interact with tubulin in a distinct way and different from other agents.

Results

Figure 19:
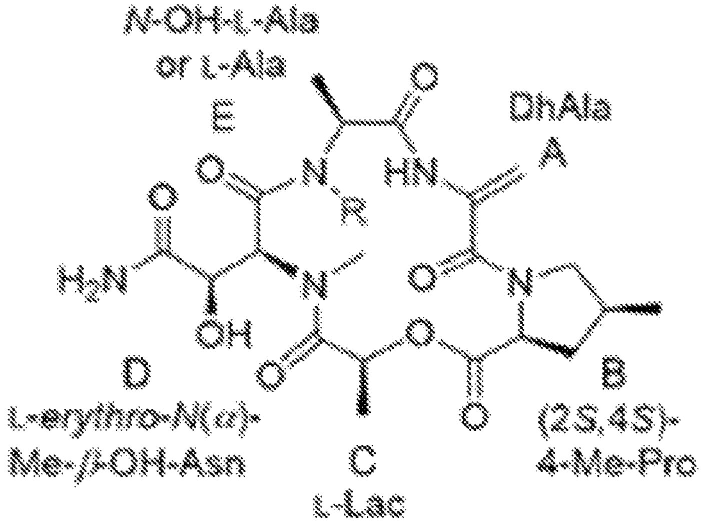
FIG. 19 depicts structures of the isolated natural products, gatorbulin-1 (GB1, 1a) and its N-deoxy-derivative, gatorbulin-2 (GB2, 1b).
Figure 20:
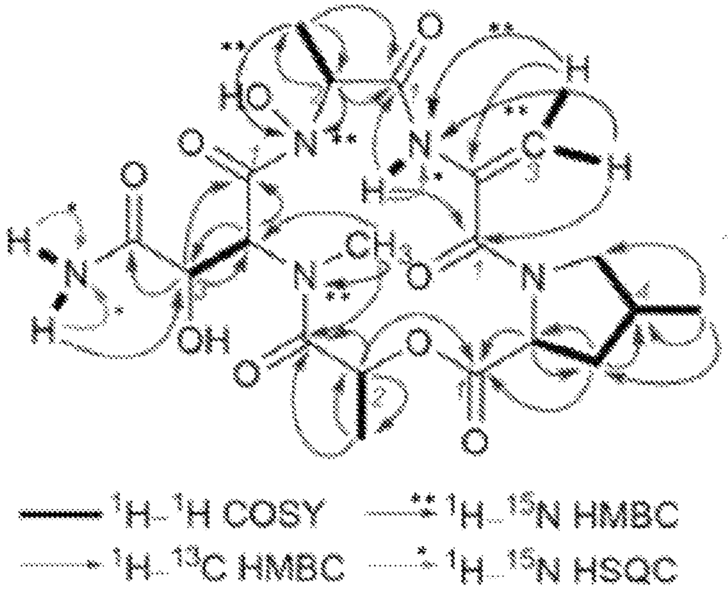
FIG. 20 depicts homo- and heteronuclear 2D NMR correlations for GB1.

Isolation and structure determination. Various collections of the cyanobacterium *Lyngbya* cf. *confervoides* during blooms off the coast near Ft. Lauderdale[11] (Broward County) were extracted with EtOAc-MeOH (1:1). The extracts, previously proven to be rich in secondary metabolites and possessing antifeedant activity[12,13], w were either solvent-solvent partitioned first or directly applied onto a Diaion HP-20 column and then fractions subjected to reversed-phase HPLC to afford gatorbulin-1 (GB1) as an optically active white solid ($[\alpha]^{20}_D$−84.0 (c 0.10, MeOH)) and as the most antiproliferative extract component by bioassay-guided isolation using colon cancer cells, along with a minor analogue, gatorbulin-2 (FIG. 19). Doubling of virtually every signal in the $^1H$ NMR spectrum of gatorbulin-1 recorded in DMF-$d_7$ suggested the presence of an asymmetric dimer or the presence of conformers in a ratio of 1:1. This observation coupled with the $[M+H]^+$ ion peak at m/z 484.2043 obtained by HRESI/APCIMS and $^{13}C$ NMR data suggested a molecular formula of $C_{20}H_{29}N_5O_9$ (calcd for $C_{20}H_{30}N_5O_9$, 484.2044) and consequently the presence of conformers in the NMR solvent. NMR analysis using $^1H$ NMR, $^{13}C$ NMR, COSY, HMQC, and $^1H$-$^{13}C$ HMBC data was carried out for both conformers, revealing two sets of five spin-coupled systems as part of a pentapeptide structure; one signal set appeared slightly broader (FIG. 18 FIG. 20).

For both signal sets, one putative NH singlet each ($\delta_H$ 8.28 and 8.60) showed COSY correlations to $sp^2$-methylene protons ($\delta_H$ 6.46/5.22 for conformer 1, 6.22/5.11 for conformer 2) which also appeared as singlets in $^1H$ NMR spectrum. Correlations from the NH to the corresponding olefinic methylene carbon ($\delta_C$ 101.8 and 103.0), to a quaternary $sp^2$ hybridized carbon ($\delta_C$ 136.3 and 136.2) and to two carbonyl carbons ($\delta_C$ 165.9/170.5 for conformer 1 and 166.8/170.2 for conformer 2) defined the first unit as a dehydro-alanine (DhAla) residue (FIGS. 18 and 19) as a dehydro-alanine (DhAla) residue (FIG. 18, FIG. 20).

The second multi-proton spin system consisted of two methylenes ($\delta_H$ 4.31/3.25, 2.58/1.58 for conformer 1), two methines ($\delta_H$ 4.42, 2.53) and one methyl group ($\delta_H$ 1.12 d). COSY analysis established their arrangement supported by HMBC data (FIG. 18, FIG. 20). The terminal methine and methylene carbons of this spin system appeared to be nitrogenated ($\delta_C$ 62.6, 56.9) and the HMBC correlation of one of the methylene protons ($\delta_H$ 4.31) to one of the methine carbons ($\delta_C$ 62.6) clarified that the carbons were joined in a 3-methyl pyrrolidine structure (FIG. 20), which upon further analysis of HMBC correlations to a carbonyl carbon ($\delta_H$ 170.8) identified the second residue as a 4-methylproline unit (4-MePro). In a similar fashion, a signal set corresponding to the second conformer for this unit was unambiguously identified (FIG. 18).

Analysis of the third spin system was straightforward and this unit consisted of only one methine and a methyl group and NMR data (FIG. 18 and FIG. 20), consistent with an acylated lactic acid (Lac) moiety (FIG. 19).

Two singlets of another signal set for heteroatom-bound protons ($\delta_H$ 7.26/7.09 for conformer 1 and $\delta_H$ 7.39/7.21 for conformer 2) showed cross-peaks in the COSY spectrum, suggesting a primary amide. Another set of singlets at $\delta_H$ 3.09 and 3.14 was indicative of an N-methyl tertiary amide group; expectedly these signals exhibited HMBC correlations with a carbonyl carbon of the adjacent residue ($\delta_C$ 169.9 and 169.7) and for conformer 1 also to the α-carbon of the N-methylated amino acid ($\delta_C$ 58.0). Rigorous 2D NMR analysis established the second unit as an N(α)-methyl-β-hydroxy-asparagine (N(α)-Me-β-OH-Asn). Even though the significant broadening of all signals for this unit for the second conformer resulted in fewer HMBC correlations, all $^1$H and $^{13}$C NMR resonances could be assigned except for the α-carbon since its NMR signal was too broad to be observed (FIG. 18).

The last unit exhibited similarity to a lactic acid or alanine moiety, yet the α-carbon resonated at higher field than the corresponding carbon for lactic acid ($\delta_C$ 64.7 and 60.0) and thus more likely bore a nitrogen atom, which then in turn had to bear a substituent that was not accounted for yet. This NMR analysis so far led to the assignment of all atoms except one oxygen and hydrogen based on HRMS analysis. In the $^1$H NMR spectrum, the only unassigned signal at this point was a signal for an exchangeable proton at $\delta_H$ 11.35 (br s) for conformer 1 and at $\delta_H$ 10.58 (br) putatively for conformer 2, which could not be rationalized by a secondary amide since it did not show a COSY correlation to the nitrogen-bearing methine while also resonating too far downfield. The chemical shifts were consistent with carboxylic acid protons which could exist in a linear structure; however, it would not leave a substituent for the nitrogen atom in the alanine-like moiety. Therefore, a bond between two heteroatoms, nitrogen and oxygen, had to be invoked which led us to propose a N-hydroxy group in a cyclic hydroxamate (N—OH-Ala); its hydroxy proton was also expected to resonate between $\delta_H$ 10-12 as observed.

Figure 21:
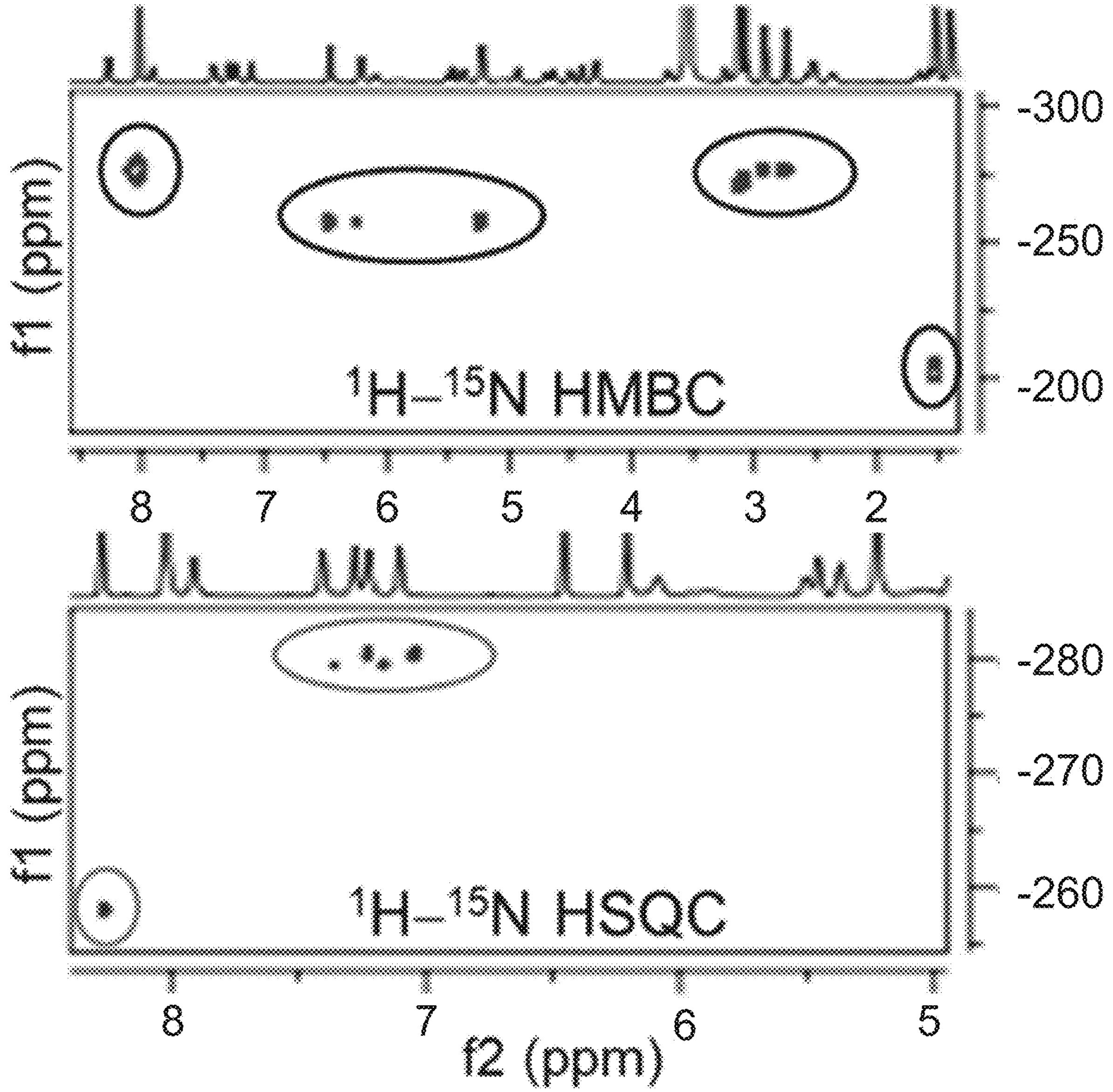
FIG. 21 depicts selected regions of the $^1H$-$^{15}N$ HMBC and $^1H$-$^{15}N$ HSQC spectra of GB1.

The doubling and overlap of signals for several carbonyl carbons for different conformers slightly complicated the sequencing of the individual units. To ultimately prove the existence of the hydroxamate and to validate the nature of the nitrogen atoms we carried out a $^1$H-$^{15}$N HMBC analysis (FIG. 18). Correlations of the H-3a/b methylene protons of the DhAla unit to a nitrogen atom resonating at $\delta_N$–258.2 (relative to external $MeNO_2$, $\delta_N$ 0.0) supported the earlier assignment of a secondary amide (FIGS. 20-21). The N-Me protons of the N-Me-3-OH-Asn showed HMBC correlations to a nitrogen possessing a chemical shift of $\delta_N$–273.8, an expected value for a tertiary amide (FIGS. 20-21). Most importantly and confirmatory for the hydroxamate moiety were two- and three-bond correlations from the α-methine and the β-methyl protons to a signal at $\delta_N$–202.6 (FIGS. 20-21) which is in agreement with literature values for hydroxamate nitrogens ($\delta_N$–199.2 for polyoxypeptin A[14]), further validating the proposed structure for GB1 (1a). The $^1$H-$^{15}$N HSQC spectrum, in addition to the secondary amide proton for DhAla ($\delta_N$–258.2), also showed one-bond correlations for both protons of the primary amide functionality for both conformers ($\delta_N$–280.5 and –279.6, FIG. 21). The presence of the hydroxamate functionality was supported analytically by ferric hydroxamate complex formation[15].

Further support for the proposed structure was found with the isolation of its N-deoxy-derivative, termed gatorbulin-2 (GB2), or N-deoxy-gatorbulin-1 (FIG. 19). The $^1$H NMR spectrum was strikingly similar to the one of GB1, including the presence of conformers in a 1:1 ratio in DMF-$d_7$. The most significant difference appeared to be the lack of the N—OH protons at $\delta_H$ 10-12; instead a new set of doublets appeared in the range for amide protons ($\delta_H$ 8.21 and 8.38 for conformers 1 and 2).

To establish the absolute configuration, we performed acid hydrolysis to liberate the individual units and synthesized all isomers of the amino acid standards for comparative chiral HPLC analysis and advanced Marfey's analysis. The 4-MePro standards were prepared as described previously[16] and the N(α)-Me-β-OH-aspartic acid stereoisomers as described as provided herein. We detected L-eiythro-N(α)-Me-β-OH-Asp, (2S,4S)-4-Me-Pro, and L-Lac in the hydrolyzate of 1a. The structures and identical absolute configurations were confirmed by conversion of 1a into 1b via $TiCl_3$-mediated reduction (FIG. 19)[17]. Upon acid hydrolysis, 1b yielded L-Ala as detected by chiral HPLC analysis, establishing the remaining stereogenic center.

Figure 22:
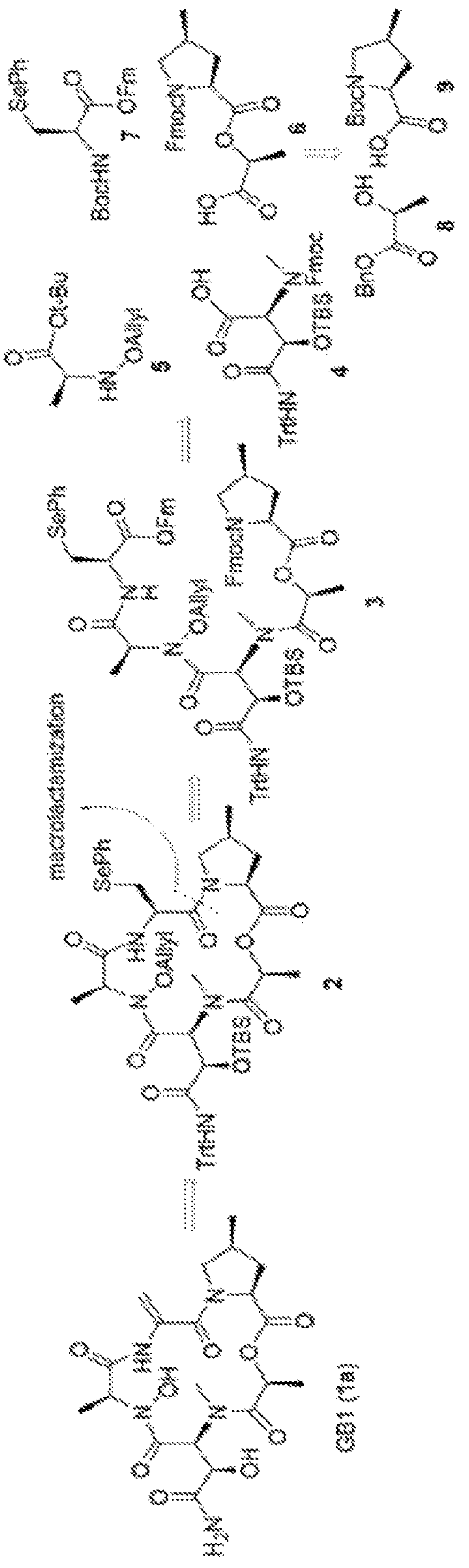
FIG. 22 depicts a retrosynthetic analysis for the total synthesis of gatorbulin-1 (GB1, 1a).

Synthesis of gatorbulin-1. To prove the structure and overcome the supply issue, we embarked on the total synthesis. The retrosynthetic analysis of total synthesis of gatorbulin-1 (GB1) is shown in FIG. 22. The final product GB1 could be obtained from the fully masked cyclized precursor 2 by sequential deprotection. The site between 4-MePro and (Se)-phenylselenocysteine (Sec(Ph)) was chosen for macrolactamization. In linear precursor 3, Fmoc-Fm pair was designed as the protection groups of amino and carboxy termini, respectively, which could be cleaved simultaneously with base to provide the precursor of macrocyclization[20]. Sec(Ph) was proposed as the pro-unit of DhAla[21]. Linear compound 3 was disconnected into four building blocks 4-7, which could be constructed from commercially available reagents (e.g., 6 from 8 and 9) using established or modified protocols.

Figure 23:
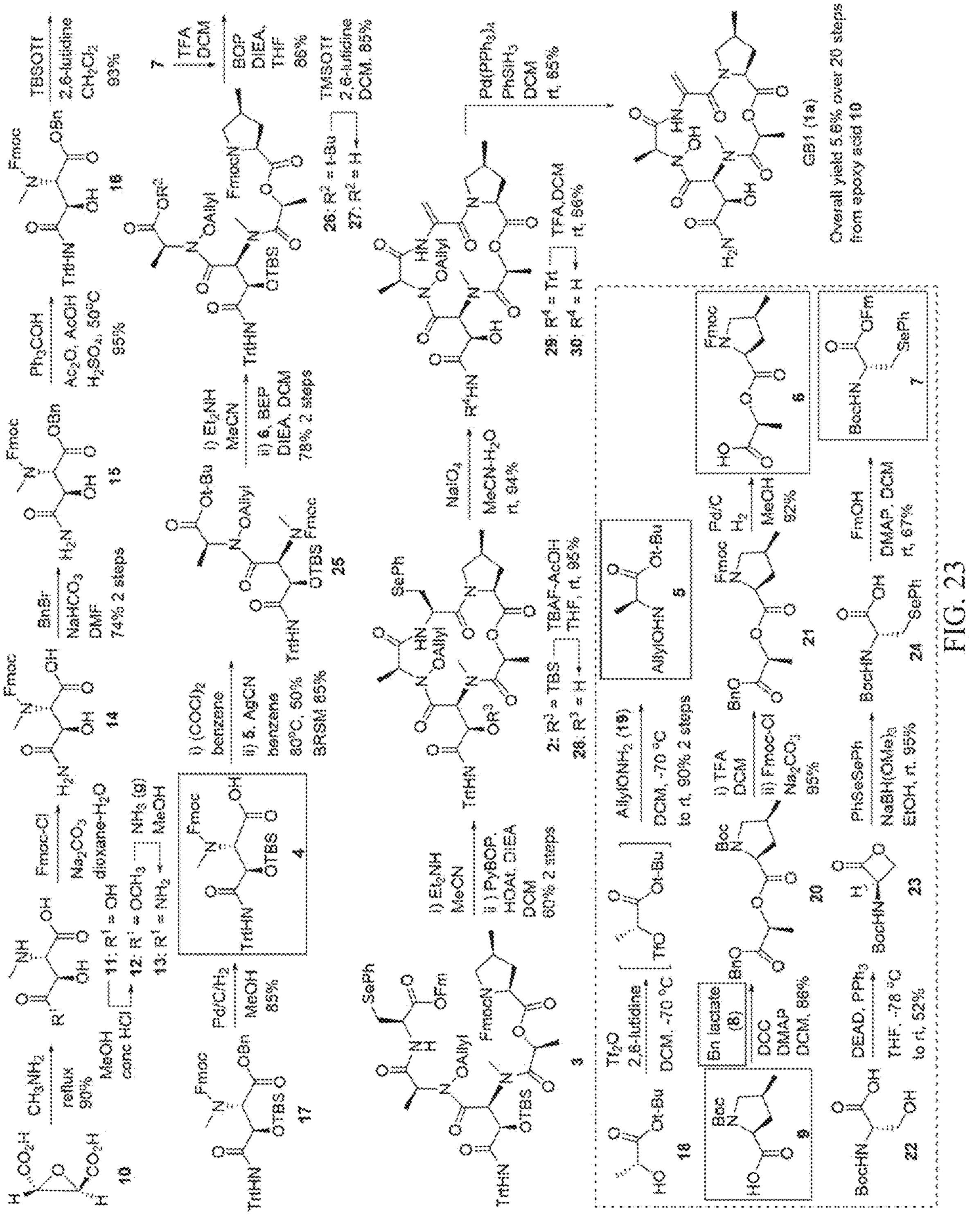
FIG. 23 depicts a forward synthetic route. Longest linear sequence is shown in the main scheme. Building blocks 4-9 from the retrosynthesis are indicated by boxes with solid lines. The synthesis of the building blocks 5-7 is provided in the box with the dashed line

FIG. 23 depicts the synthetic route to gatorbulin-1 (GB1). The synthesis of acid 4 was adopted from published proedures[22]. (2R,3R)-epoxysuccinic acid (10) was converted to erythro-N(α)-methyl-3-hydroxy-L-aspartic acid (11) by treatment with methylamine-water under reflux. Then 11 was selectively esterified with acidic methanol under refluxing[23] to provide monoester 12. Without purification, aminolysis of 12 with ammonia (gas) in MeOH provided N(α)-methyl-β-hydroxy-asparagine (13)[22,23], which had poor solubility in MeOH, so that pure product could be obtained by simple filtration. Sequential protections of the groups of 13 using standard methods[24] provided full masked compound 17. Finally, acid 4 was obtained from 17 by hydrogenation with palladium catalyst.

The synthesis of building block of allyloxamine 5 adopted the triflate method[25]. Allyl was chosen as NOH protecting group as it could be selectively removed by $Pd(Ph_3P)_4$ in the presence of dehydropeptide. Acid 6 was synthesized from (4S)—N-Boc-4-methyl-Pro (9) and benzyl-L-lactate (8) by standard protocols of esterification, protection and deprotection. Following established procedures[21], N-Boc-serine (22) was converted to BocSec(Ph) (24) via δ-lactone 23, which was esterified with FmOH to provide building block 7. Dehydroalanine could be obtained from phenylselenocysteine by oxidative β-elimination.

The fusion of building blocks was initiated by coupling of acid 4 with allyloxamine 5. Acid 4 was activated to the acid chloride, which was then coupled with 5 in presence of AgCN[26,27] to provide 25 in 50% yield and 85% yield based on recovered starting materials (BRSM). This acylation was not successful when other common coupling reagents were used because of poor nucleophilicity of the nitrogen and high steric hindrance[28]. Compound 26 was obtained in 78% yield by BEP-mediated coupling[29] of acid 6 with the free methyl amine generated by selective deprotection of 25. Selective removal of t-butyl group of 26 by TMSOTf/2,6-lutidine[30] afforded acid 27, which was coupled with free amine from 7 using BOP as coupling reagent to yield the linear compound 3 in 86% yield. The use of the t-butyl protecting group prevented diketopiperazine 31 formation upon coupling of 6 and 25, and ensured that trityl and TBS groups were intact for the generation of acid 27. Both Fmoc and Fm protection groups were removed simultaneously when compound 3 was exposed to $Et_2NH$ in MeCN. The macrocyclization was mediated by PyBOP/HOAt to give macrocycle 2 in 60% yield for two steps. Removal of TBS of 2 with the TBAF/HOAc buffer[24,32] provided 28, and subsequent oxidation of SePh with $NaIO_4$[21] yielded dehydropeptide 29. Trityl was removed with TFA in $CH_2Cl_2$[33] to yield primary amide 30. The removal of allyl group by $Pd(PPh_3)_4/PhSiH_3$[32,34] provided final product 1a. The removal sequence for trityl and allyl groups are interchangeable; however, the yield would drop from 66% to 35%. GB1 (1a) was purified by reverse TLC plate ($C_{18}$) with acceptable purity. The synthetic sample was identical to the isolated natural product, which was verified by NMR, HRMS and optical rotation (natural 1a: $[\alpha]^{20}_D$−84.0 (c 0.10, MeOH); synthetic 1a: $[\alpha]^{20}_D$−119.2 (c 0.17, MeOH).

Figure 24:
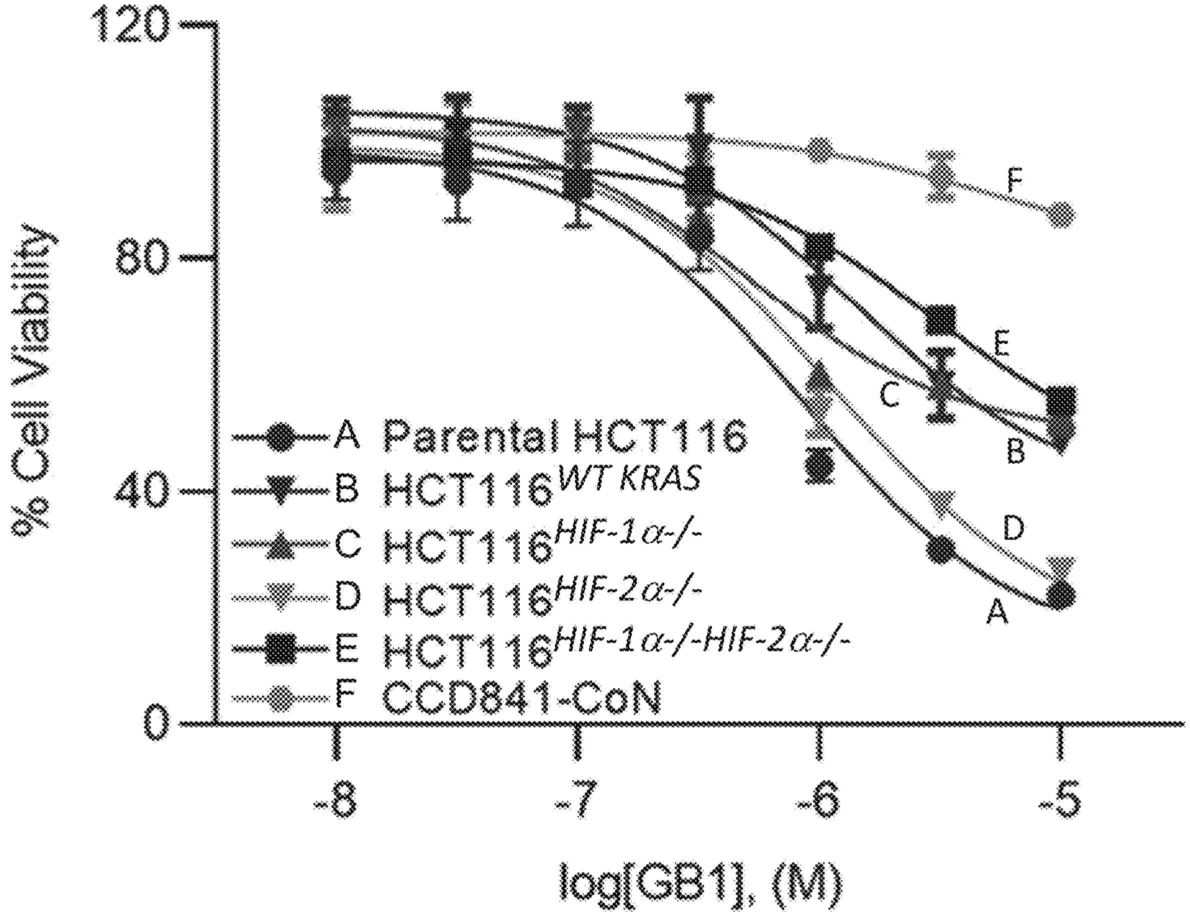
FIG. 24 depicts antiproliferative activity of GB1 in parental HCT116 colon cells, isogenic HCT116 knockout cells, and CCD-841CoN normal epithelial colon cells (48 h treatment). GB1 showed a marginal effect on the viability of CCD-841CoN normal epithelial colon cells (0.5% DMSO vehicle). Parental HCT116 cells and $HCT116^{HIF\text{-}2\alpha-/-}$ were most susceptible, while the potency and efficacy of GB1 were reduced against $HCT116^{HIF\text{-}1\alpha-/-HIF\text{-}2\alpha-/-}$, $HCT116^{HIF\text{-}1\alpha-/-}$, and oncogenic KRAS knockout ($HCT116^{WT\ KRAS}$). Cell viability was measured by MTT assay (n=3). Data are represented as average±SD.
Figure 25:
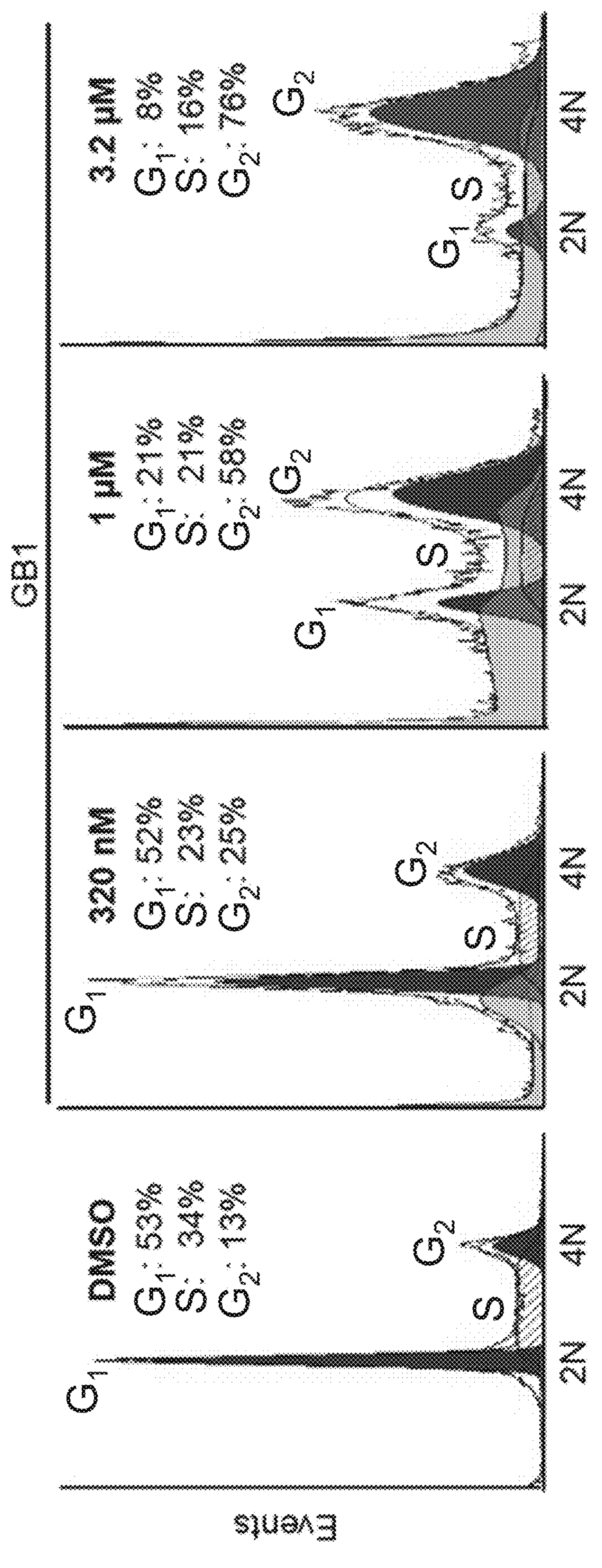
FIG. 25 depicts a cell cycle analysis. HCT116 cells were treated with GB1 (320 nM, 1 μM, 3.2 μM) or vehicle control (0.25% DMSO) for 24 h and DNA content assessed by flow cytometry of propidium iodide stained cells. GB1 induced $G_2$/M accumulation.
Figure 26:
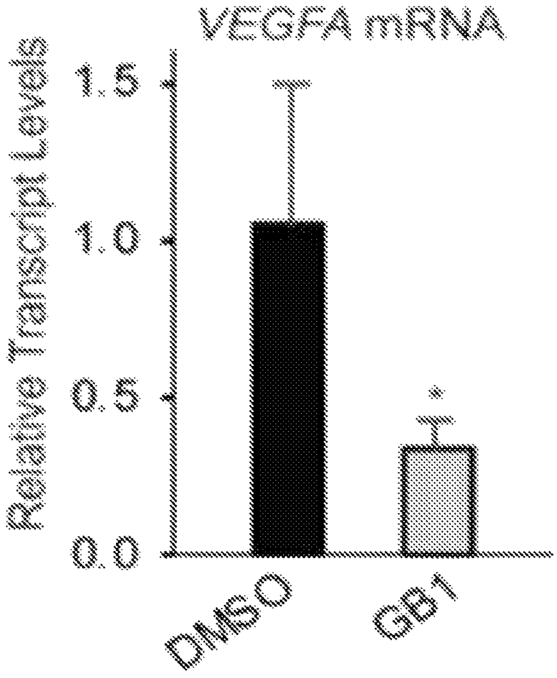
FIG. 26 depicts HIF target gene (VEGFA) expression after 16 h exposure of parental HCT116 cells to GB1 (3.2 μM) or vehicle (0.25% DMSO). RNA was isolated, reverse transcribed and subjected to qPCR using TaqMan analysis. β-actin served as endogenous control. Error bars indicate mean±SD of three replicates (student t test, $*p<0.05$).

HIF-selectivity and cellular profiling identifies the mechanism of action. GB1 (1a) was identified as the extract's active component against colon cancer cells and showed an $IC_{50}$ of 0.80 μM (MTT assay) against HCT116 colorectal cancer cells (FIG. 24, while GB2 (1b) was inactive at the highest concentration tested ($IC_{50}$>10 μM), indicating that the hydroxamate moiety is indispensable to the antiproliferative activity. Isogenic cell line selectivity screening indicated preferential activity against parental HCT116 compared with the oncogenic KRAS knockout or double knockout of both HIF-1α and HIF-2α transcription factors (FIG. 24. Deconvolution using single knockouts of HIF-1α and HIF-2α clearly demonstrated that only cells depleted in HIF-1α had reduced susceptibility to GB1 (1a), which is consistent with HIF-1α being in the same pathway and activated by oncogenic KRAS. Furthermore, normal epithelial colon cells (CCD841CoN), were less inhibited indicating an additional promising level of selectivity (FIG. 24). The preference for HIF-1α expressing cells parallels the selectivity profiles for microtubule agents we previously discovered (dolastatins 10 and 15)[4,7]. DNA content analysis revealed the concentration-dependent G2/M cell cycle accumulation characteristic for antimitotic agents (FIG. 25). A concentration of GB1 (4×$IC_{50}$) that results in a complete antiproliferative response, initiated a concomitant downregulation of the HIF-1α target gene VEGFA in parental HCT116 cells (FIG. 26), even more pronounced than for dolastatin 15[4], which also elevated its potential as antiangiogenic agent. Taken together, this reveals an antiangiogenic role of the compound in inhibiting the formation and stabilization of a three-dimensional vascular network. The additional VEGF downregulation in growth factor secreting cells is expected to more pronounced angiogenic action.

Figure 27:
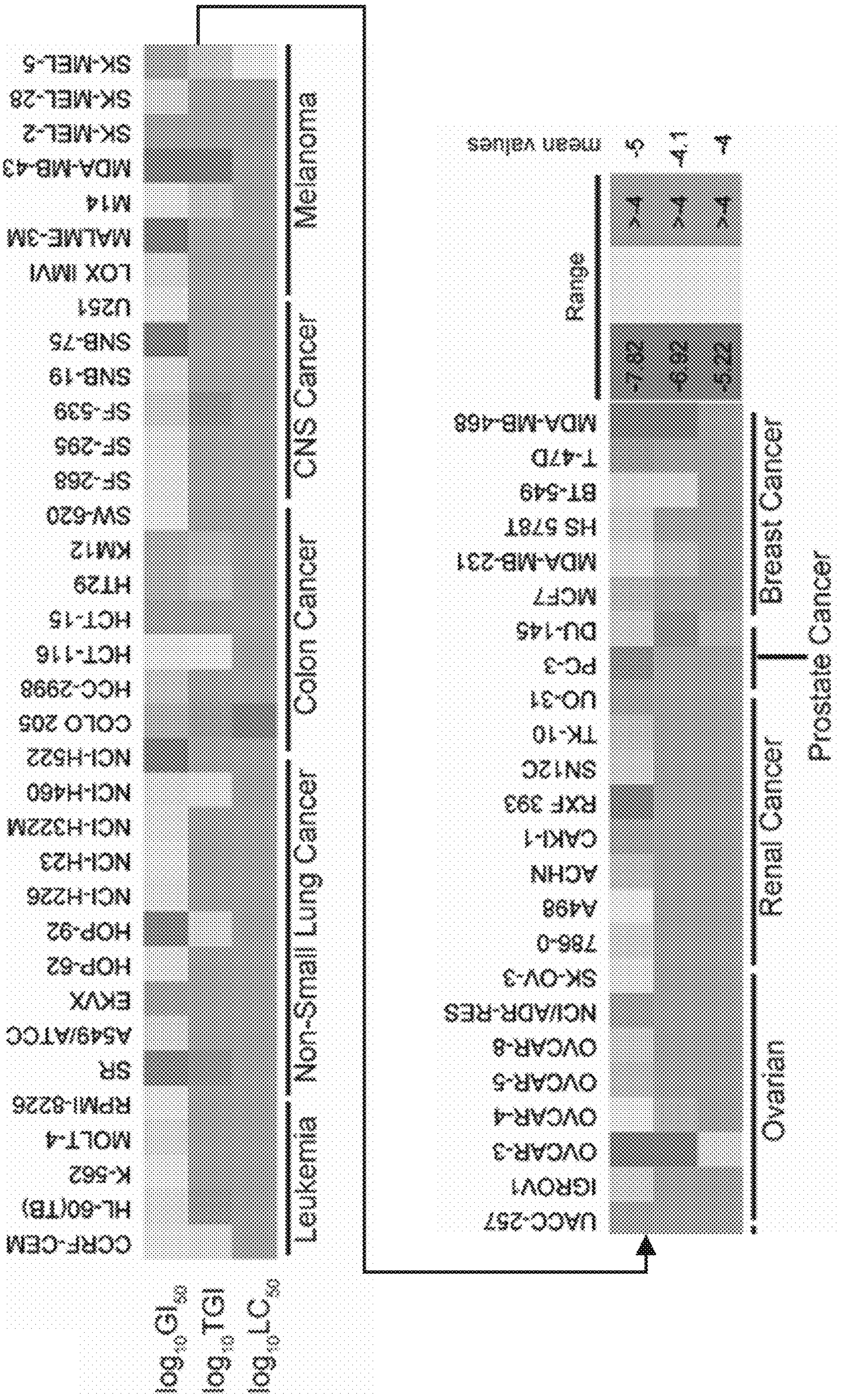
FIG. 27 depicts a heatmap for the performance of GB1 across cell lines in the NCI-60 screen using three different values (growth-inhibitory effect, $GI_{50}$; cytostatic effect, TGI; cytotoxic effect, $LC_{50}$; concentration in M).

The NCI-60 screen data (FIG. 27), analyzed by the COMPARE algorithm[19,34b], were indicative of a cytotoxicity profile most related to antimitotic/tubulin agents, including paclitaxel, eribulin, colchicine and vinca bis-indole alkaloid derivatives (P 0.75-0.85), suggesting that the biochemical mechanisms of action are related. While GB1 displayed an $IC_{50}$>10 μM against normal mucosal colon cells, it had submicromolar activity against HCT116 cells ($GI_{50}$ 306 nM) and was even more potent against COLO205 cells ($GI_{50}$ 92 nM) based on the NCI-60 data (sulforhodamine B assay). Other susceptible cell types included certain melanoma (SK-MEL-5), ovarian (OVCAR-3) and prostate (DU-145) cancer cells, which correspond to certain cancers where microtubule agents have been successful. Furthermore, cervical and breast cancers are relevant indications, prompting additional studies in these cell types[35].

Target Identification and Inhibition of Tubulin Polymerization by Gatorbulin-1

Figure 28:
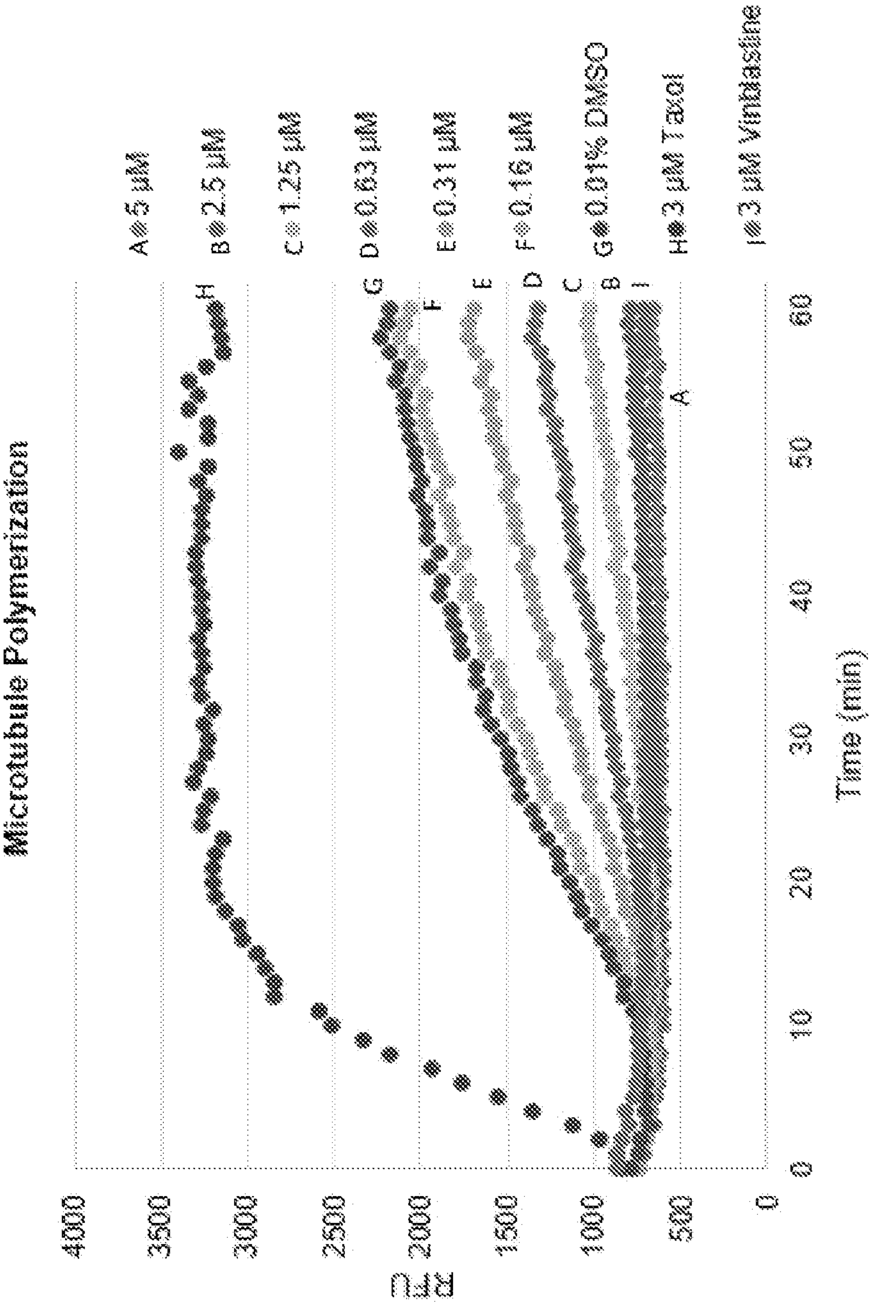
FIG. 28 depicts Target identification and inhibition of tubulin polymerization by gatorbulin-1 (1a).

First, using a biochemical assay, we demonstrated that gatorbulin-1 (1a) directly inhibits tubulin polymerization in vitro (FIG. 28).

Figure 29:
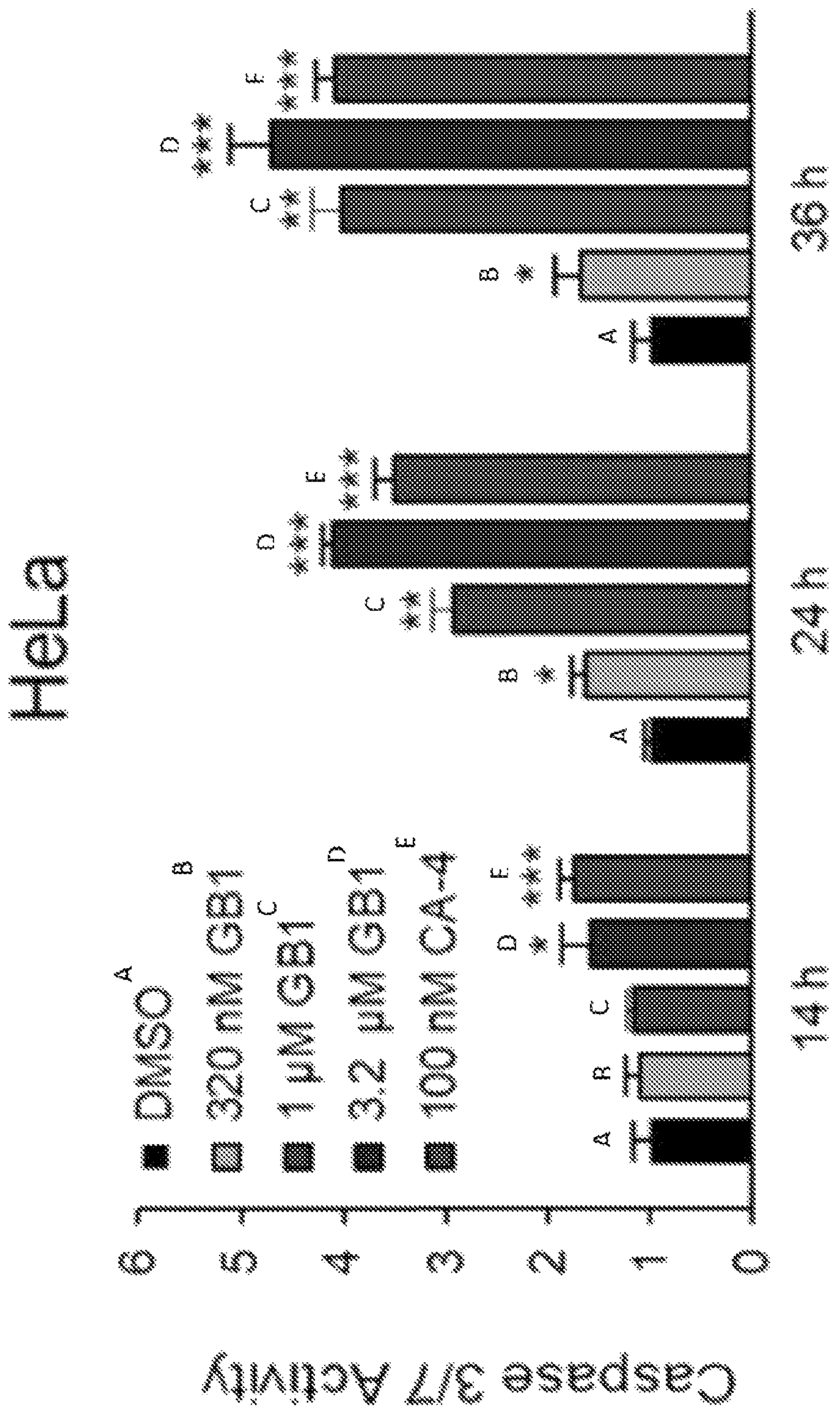
FIG. 29 depicts that GB1 causes apoptosis in HeLa cells with increased caspase activity. HeLa cells were treated with increasing concentrations of GB1 and combretastatin-4 (CA-4) (100 nM) using 0.5% DMSO as solvent control. Caspase-3/7 activity was measured using Caspase-Glo 3/7 reagent kit at 14 h, 24 h and 36 h. Data represents average of three replicates with ±SD. The p-values were calculated using two-tailed Student t-test; $*p<0.05$, $p<0.01$, $*p<0.005$.

We then measured the caspase-3/7 activity in a concentration- and time-dependent manner, validating that treatment with GB1 induces apoptosis at concentrations that affect tubulin dynamics in cells, especially after 24 h and beyond, similar to CA-4 (FIG. 29).

Discussion

We took an integrated approach towards natural products drug discovery by targeting minor, highly bioactive compounds from a chemically prolific cyanobacterium, combining innovative screening and rigorous bioassay-guided isolation and structure determination with chemical synthesis to overcome the supply problem, identified tubulin as direct target and performing achieving in depth-mechanistic studies as well as direct target and binding site identification. We advocated for such an approach to fully exploit the proven potential of natural products and increase the value of bioactive natural products[42]. The ultimate key for a successful natural product drug discovery campaign is the choice of the source organism. We have been focusing on marine cyanobacteria, which are prolific yet underexplored marine prokaryotes with a tremendous biosynthetic potential. The gatorbulin-yielding sample was derived from a blooming "superproducer" of secondary (specialized) metabolites (natural products) that previously yielded lyngbyastatins 4-6, pompanopeptins A and B, tiglicamides, largamides/largamide D oxazolidine, most of which are noncytotoxic serine protease inhibitors[12,13,43-45]. Beyond showcasing the biosynthetic capacity of marine cyanobacteria, our discovery of gatorbulin-1 exemplifies that marine cyanobacterial natural products occupy therapeutically relevant chemical space that could lead to the discovery of new biology, chemical tools or even drug leads.

Gatorbulin-1 is a small (MW<500 g/mol) cyclodepsipeptide, unique from most cyanobacterial modified peptides or peptide-polyketide hybrids, which dominate the landscape of bioactive natural products produced by marine cyanobacteria[49]. GB1 is densely functionalized with all amino acids being modified and the presence of one hydroxy acid.

Natural produces possessing all of these unusual structural features of GB1 (i.e., the hydroxamate, C-hydroxylated and dehydro-amino acids, modified proline) have not been reported. The 4-methylproline residue is a rare feature but has been previously found in cyanobacterial natural products[16]. Interestingly, the hydroxamate group that is typical for metal chelators (especially ion siderophores) and present in other antiproliferative compounds[46], plays an iron-dependent functional role in GB1's binding to tubulin as the major mechanism of antiproliferative action. The additional metal binding ability potentially increases the pharmacological complexity of GB1 and remains to be investigated. However, the iron complexing ability due to the hydroxamate functionality was proven but appeared not to play a predominant role with respect to the antiproliferative activity, based on the NCI-60 profile and cell cycle arrest characteristic for tubulin targeting agents. We neither found the metal was necessary for GB1 binding to tubulin and the inhibition of tubulin assembly into microtubules in our in vitro assays.

We previously reported the discovery of the microtubule-destabilizers dolastatins 10 and 15[2-4], which bind to the vinca domain, as indirect HIF inhibitors in our cell-based phenotypic screens. Dolastatin 10 originated from a new genus of marine cyanobacteria[2,3,47], further validating the unexplored genetic diversity of cyanobacteria that translates into chemical diversity. HIF inhibition likely contributes to the overall anticancer activity of most microtubule binding drugs, including GB1[48].

Gatorbulin-1 is a cyclic depsipeptide that represents a new chemotype that differs from other peptides targeting tubulin such as dolastatin 10 and possesses low toxicity and molecular weight, adding to its promising small-molecule, drug-like properties and translational potential.

REFERENCES FOR DESCRIPTION OF THE EXAMPLES

1. Risinger, A. L. & Du, L. Targeting and extending the eukaryotic druggable genome with natural products: cytoskeletal targets of natural products. *Nat. Prod. Rep.* 37, 634-652 (2020).
2. Luesch, H., Moore, R. E., Paul, V. J., Mooberry, S. L. & Corbett, T. H. Isolation of dolastatin 10 from the marine cyanobacterium Symploca species VP642 and total stereochemistry and biological evaluation of its analogue symplostatin 1. *J. Nat. Prod.* 64, 907-910 (2001).
3. Salvador-Reyes, L. A., Engene, N., Paul, V. J. & Luesch, H. Targeted natural products discovery from marine cyanobacteria using combined phylogenetic and mass spectrometric evaluation. *J. Nat. Prod.* 78, 486-492 (2015).
4. Ratnayake, R. et al. Dolastatin 15 from a Marine Cyanobacterium Suppresses HIF-1α Mediated Cancer Cell Viability and Vascularization. *Chem Bio Chem* (2020) doi:10.1002/cbic.202000180.
5. Bai, R., Pettit, G. R. & Hamel, E. Binding of dolastatin 10 to tubulin at a distinct site for peptide antimitotic agents near the exchangeable nucleotide and vinca alkaloid sites. *J. Biol. Chem.* 265, 17141-17149 (1990).
6. Cruz-Monserrate, Z., Mullaney, J. T., Harran, P. G., Pettit, G. R. & Hamel, E. Dolastatin binds in the vinca domain of tubulin as demonstrated by Hummel-Dreyer chromatography. *Eur. J. Biochem.* 270, 3822-3828 (2003).
7. Bousquet, M. S. et al. Multidimensional screening platform for simultaneously targeting oncogenic KRAS and hypoxia-inducible factors pathways in colorectal cancer. *ACS Chem. Biol.* 11, 1322-1331 (2016).
8. Pouysségur, J., Dayan, F., Mazure, N. M. Hypoxia signalling in cancer and approaches to enforce tumour regressio. *Nature* 441, 437-443 (2006).
9. Semenza, G. L. Targeting HIF-1 for cancer therapy. *Nat. Rev. Cancer* 3, 721-732 (2003).
10. Zhong, H. et al. Overexpression of hypoxia-inducible factor 1a in common human cancers and their metastases. *Cancer Res.* 59, 5830-5835 (1999).
11. Paul, V. J., Thacker, R. W., Banks, K. & Golubic, S. Benthic cyanobacterial bloom impacts the reefs of South Florida (Broward County, USA). *Coral Reefs* 24, 693-697 (2005).
12. Sharp, K. et al. Phylogenetic and chemical diversity of three chemotypes of bloom-forming *Lyngbya* species (cyanobacteria: Oscillatoriales) from reefs of southeastern Florida. *Appl. Environ. Microbiol.* 75, 2879-2888 (2009).
13. Matthew, S. et al. Intramolecular modulation of serine protease inhibitor activity in a marine cyanobacterium with antifeedant properties" *Mar. Drugs* 8, 1803-1816 (2010).
14. Umezawa, K., Ikeda, Y., Kawase, O., Naganawa, H. & Kondo, S. Biosynthesis of polyoxypeptin A: Novel amino acid 3-hydroxy-3-methylproline derived from isoleucine. *J. Chem. Soc. Perkin Trans* 1 13, 1550-1553 (2001).
15. Steele, A. D. et al. Diverted total synthesis of promysalin analogs demonstrates that an iron-binding motif is responsible for its narrow-spectrum antibacterial activity. *J. Am. Chem. Soc.* 138, 5833-5836 (2016).
16. Luesch, H. et al. Biosynthesis of 4-methylproline in cyanobacteria: Cloning of nosE and nosF genes and biochemical characterization of the encoded dehydrogenase and reductase activities. *J. Org. Chem.* 68, 83-91 (2003).
17. Mattingly, P. G. & Miller, M. J. Titanium trichloride reduction of substituted N-hydroxy-2-azetidinones and other hydroxamic acids. *J. Org. Chem.* 45, 410-415 (1980).
18. Schwartz, E. L. Antivascular actions of microtubule-binding drugs. *Clin. Cancer Res.* 15, 2594-2601 (2009).
19. Paul K. D., Hamel E., M. L. *Cancer Chemotherapeutic Agents*. (American Chemical Society Books, Washington, DC, 1995).
20. Kim, B et al. Evaluation of class I HDAC isoform selectivity of largazole analogues. *Bioorganic Med. Chem. Lett.* 24, 3728-3731 (2014).
21. Ley, S. V., Prieur, A. & Heusser, C. Total synthesis of the cyclic heptapeptide Argyrin B: A new potent inhibitor of T-cell independent antibody formation. *Org. Lett.* 4, 711-714 (2002).
22. Sendai, M., Hashiguchi, S., Tomimoto, M., Kishimoto, S., Matsuo, T., Ochiai, M. Synthesis of carumonam (AMA-1080) and a related compound starting from (2R, 3R)-epoxysuccinic acid. *Chem. Pharm. Bull* 33, 3798-3810 (1985).
23. Guzman-Martinez, A., VanNieuwenhze, M. An operationally simple and efficient synthesis of orthogonally protected L-threo-b-hydroxyasparagine. *Synlett* 10, 1513-1516 (2007).
24. Boger, D. L., Lee, R. J., Bounaud, P. Y. & Meier, P. Asymmetric synthesis of orthogonally protected L-threo-β-hydroxyasparagine. *J. Org. Chem.* 65, 6770-6772 (2000).
25. Shustov, G. V., Chandler, M. K & Wolfe, S. Stereoselective synthesis of multiply substituted [1,2]oxazinan-3-ones via ring-closing metathesis. *Can. J. Chem.* 83, 92-103 (2005).

26. Hale K. J., S. M. & George J. Total synthesis of (+)-A83586C, (+)-kettapeptin and (+)-azinothricin: powerful new inhibitors of β-catenin/TCF4- and E2F-mediated genetranscription. *Chem. Commun.* 46, 4021-4042 (2010).

27. Hale, K. J., Manaviazar S., George J., Walters, M. A. & Dalby, S. M. Total synthesis of (+)-azinothricin and (+)-kettapeptin. *Org. Lett.* 11, 733-736 (2009).

28. Ottenheijm, H. C. J. & Herscheid, J. D. M. N-Hydroxy-α-amino Acids in Organic Chemistry. *Chem. Rev.* 86, 697-707 (1986).

29. Li, P. & Xu, J. C. 1-Ethyl 2-halopyridinium salts, highly efficient coupling reagents for hindered peptide synthesis both in solution and the solid-phase. *Tetrahedron* 56, 8119-8131 (2000).

30. Smith, A. B. et al. Design, synthesis, and biological evaluation of EF- and ABEF-analogues of (+)-Spongistatin 1. *Org. Lett.* 12, 1792-1795 (2010).

31. Shute, R. E. & Rich, D. H. Prevention of diketopiperazine formation in peptide synthesis by a simultaneous deprotection-coupling procedure: Entrapment of reactive nucleophilic species by in situ acylation. *J. Chem. Soc. Chem. Commun.* 1155-1156 (1987) doi:10.1039/C39870001155.

32. Kogen, H. et al. Crystal structure and total synthesis of globomycin: Establishment of relative and absolute configurations [5]. *J. Am. Chem. Soc.* 122, 10214-10215 (2000).

33. Bajjuri, K. M., Liu, Y., Liu, C. & Sinha, S. C. The legumain protease-activated auristatin prodrugs suppress tumor growth and metastasis without toxicity. *ChemMedChem* 6, 54-59 (2011).

34. Gaucher-Wieczorek, F. S., Maillard, L. T., Badet, B. & Durand, P. Fluorous tagged N-hydroxy phthalimide for the parallel synthesis of O-aryloxyamines *J. Comb. Chem.* 12, 655-658 (2010).

34b. K. D. Paul, E. Hamel, *Cancer Chemotherapeutic Agents*. (American Chemical Society Books, Washington, DC, 1995).

35. Parker, A. L., Teo, W. S., McCarroll, J. A. & Kavallaris, M. An emerging role for tubulin isotypes in modulating cancer biology and chemotherapy resistance. *Int. J. Mol. Sci.* 18, 1434 (2017).

36. Doodhi, H. et al. Termination of protofilament elongation by eribulin induces lattice defects that promote microtubule catastrophes. *Curr. Biol.* 26, 1713-1721 (2016).

37. Menchon, G. et al. A fluorescence anisotropy assay to discover and characterize ligands targeting the maytansine site of tubulin. *Nat. Commun.* 9, 1-9 (2018).

38. La Regina, G. et al. Arylthioindole inhibitors of tubulin polymerization. 3. Biological evaluation, structure-activity relationships and molecular modeling studies. *J. Med. Chem.* 50, 2865-2874 (2007).

39. Risinger, A. L. et al. The taccalonolides: Microtubule stabilizers that circumvent clinically relevant taxane resistance mechanisms. *Cancer Res.* 68, 8881-8888 (2008).

40. Prota, A. E. et al. Structural basis of tubulin tyrosination by tubulin tyrosine ligase. *J. Cell Biol.* 200, 259-270 (2013).

41. Weinert, T. et al. Serial millisecond crystallography for routine room-temperature structure determination at synchrotrons. *Nat. Commun.* 8, (2017).

42. Luesch, H. & Macmillan, J. B. Targeting and extending the eukaryotic druggable genome with natural products. *Nat. Prod. Rep.* 37, 744-746 (2020).

43. Matthew, S., Ross, C., Paul, V. J. & Luesch, H. Pompanopeptins A and B, new cyclic peptides from the marine cyanobacterium Lyngbya confervoides. *Tetrahedron* 64, 4081-4089 (2008).

44. Matthew, S., Paul, V. J. & Luesch, H. Tiglicamides A-C, cyclodepsipeptides from the marine cyanobacterium Lyngbya confervoides. *Phytochemistry* 70, 2058-2063 (2009).

45. Matthew, S., Paul, V. J. & Luesch, H. Largamides A-C, tiglic acid-containing cyclodepsipeptides with elastase-inhibitory activity from the marine cyanobacterium Lyngbya confervoides. *Planta Med.* 75, 528-533 (2009).

46. Bertrand, S., Helesbeux, J.-J., Larcher G., Duval, O. Hydroxamate, a key pharmacophore exhibiting a wide range of biological activities. *Mini Rev Med Chem* 13, 1311-1326 (2013).

47. Engene, N., Tronholm, A., Salvador-Reyes, L. A., Luesch, H. & Paul, V. J. Caldora penicillata gen. nov., comb. nov. (Cyanobacteria), a pantropical marine species with biomedical relevance. *J. Phycol.* 51, 670-681 (2015).

48. Mabjeesh, N. J. et al. 2ME2 inhibits tumor growth and angiogenesis by disrupting microtubules and dysregulating HIF. *Cancer Cell* 3, 363-375 (2003).

49. L. T. Tan, M. Y. Phyo, Marine cyanobacteria: A source of lead compounds and their clinically-relevant molecular targets. *Molecules* 25, 2197 (2020).

50. A. E. Prota, et al., A new tubulin-binding site and pharmacophore for microtubule-destabilizing anticancer drugs. *Proc. Natl. Acad. Sci. U.S.A.* 111, 13817-13821 (2014).

51. A. E. Prota, et al., Pironetin binds covalently to αCys316 and perturbs a major loop and helix of α-tubulin to inhibit microtubule formation. *J. Mol. Biol.* 428, 2981-2988 (2016).

52. R. B. G. Ravelli, et al., Insight into tubulin regulation from a complex with colchicine and a stathmin-like domain. *Nature* 428, 198-202 (2004).

53. B. Gigant, et al., Structural basis for the regulation of tubulin by vinblastine. *Nature* 435, 519-522 (2005).

54. M. A. Oliva, et al., Structural basis of noscapine activation for tubulin binding. *J. Med. Chem.* 63, 8495-8501 (2020).

55. Y. Wang, et al., Structures of a diverse set of colchicine binding site inhibitors in complex with tubulin provide a rationale for drug discovery. *FEBS J.* 283, 102-111 (2016).

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A compound according to Formula I:

(I)

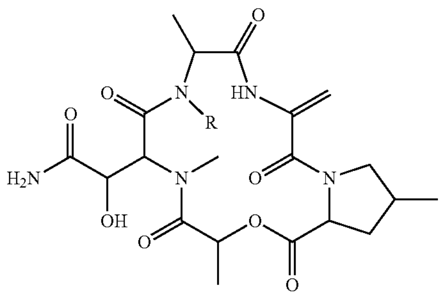

1 GB1 R = OH
2 GB2 R = H or pharmaceutically acceptable salt thereof, wherein;
R is H or OH.

2. The compound of claim 1, or pharmaceutically acceptable salt thereof, wherein R is H.

3. The compound of claim 1, or pharmaceutically acceptable salt thereof, wherein R is OH.

4. A pharmaceutical composition comprising the compound of claim 1, or pharmaceutically acceptable salt thereof, and a pharmaceutically acceptable carrier.

5. The pharmaceutical composition of claim 4 further comprising an additional therapeutic agent.

6. The pharmaceutical composition of claim 5, wherein the additional therapeutic agent is an anti-cancer agent, a chemotherapeutic agent, an anti-angiogenesis agent, a cytotoxic agent, or an anti-proliferation agent.

7. A kit comprising an effective amount of a compound of claim 1, in unit dosage form, together with instructions for administering the compound to a subject suffering from or susceptible to a cell proliferation disorder.

8. A method of reducing and/or halting cell proliferation in a subject, comprising administering to the subject the compound of claim 1 or pharmaceutically acceptable salt thereof.

9. The method of claim 8, wherein the cell is a cancer cell or a tumor cell.

10. The method of claim 8, wherein the cell proliferation is reduced and/or halted by inhibition of tubulin polymerization.

11. A method of treating a subject suffering from a cell proliferation related disorder or disease, comprising administering to the subject an effective amount of the compound of claim 1 or pharmaceutically acceptable salt thereof.

12. The method of claim 11, wherein the disorder or disease is cancer or a solid tumor.

13. The method of claim 11, wherein the effective amount ranges from:

(a) about 0.005 ug/kg to about 200 mg/kg of body weight;
(b) about 0.1 mg/kg to about 200 mg/kg of body weight;
(c) about 10 mg/kg to 100 mg/kg of body weight; or
(d) about 1.0 pM to about 500 nM.

14. The method of claim 11, wherein the compound, or pharmaceutically acceptable salt thereof, is administered intravenously, intramuscularly, subcutaneously, intracerebroventricularly, orally, or topically.

15. The method of claim 11, wherein the compound, or pharmaceutically acceptable salt thereof, is administered alone or in combination with one or more other therapeutics.

16. The method of claim 15, wherein the one or more other therapeutics is selected from the group consisting of an anti-cancer agent, a chemotherapeutic agent, an anti-angiogenesis agent, a cytotoxic agent, and an anti-proliferation agent.

17. A method of treating cancer or tumors, comprising administering to said subject having said cancer or tumors, an effective amount of a compound of claim 1, or a pharmaceutically acceptable salt thereof.

18. The method of claim 17, further comprising further comprising administering to said subject an additional therapeutic agent.

19. The method of claim 18, wherein the additional therapeutic agent is an anti-cancer agent, a chemotherapeutic agent, an anti-angiogenesis agent, a cytotoxic agent, an anti-proliferation agent, or a tubulin-interactive anti-cancer agent.

20. The method of claim 12, wherein the cancer is colon cancer, breast cancer, bone cancer, brain cancer, neuroblastoma, osteosarcoma, or colon adenocarcinoma.

* * * * *